(12) United States Patent
Yamaguchi et al.

(10) Patent No.: US 9,843,002 B2
(45) Date of Patent: Dec. 12, 2017

(54) ORGANOMETALLIC COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Tomoya Yamaguchi, Kanagawa (JP); Hideko Inoue, Kanagawa (JP); Tatsuyoshi Takahashi, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 15/332,309

(22) Filed: Oct. 24, 2016

(65) Prior Publication Data

US 2017/0125707 A1    May 4, 2017

(30) Foreign Application Priority Data

Oct. 29, 2015    (JP) .................................. 2015-212831

(51) Int. Cl.
| | | |
|---|---|---|
| *C07F 15/00* | (2006.01) | |
| *C09K 11/06* | (2006.01) | |
| *H01L 51/00* | (2006.01) | |
| *H01L 51/50* | (2006.01) | |

(52) U.S. Cl.
CPC ...... *H01L 51/0085* (2013.01); *C07F 15/0033* (2013.01); *C09K 11/06* (2013.01); *C09K 2211/1044* (2013.01); *C09K 2211/185* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01)

(58) Field of Classification Search
CPC ...................................................... C07F 15/00
See application file for complete search history.

(56) References Cited

U.S. PATENT DOCUMENTS

| | | |
|---|---|---|
| 8,946,697 B1 | 2/2015 | Ma et al. |
| 2014/0131663 A1 | 5/2014 | Beers et al. |
| 2014/0131676 A1 | 5/2014 | Beers et al. |
| 2016/0093818 A1 | 3/2016 | Inoue et al. |

FOREIGN PATENT DOCUMENTS

| | | |
|---|---|---|
| JP | 2009-013366 A | 1/2009 |
| JP | 2009-023938 A | 2/2009 |
| JP | 2014-094941 A | 5/2014 |
| WO | WO 2009/011447 A2 | 1/2009 |

*Primary Examiner* — Brian McDowell
(74) *Attorney, Agent, or Firm* — Husch Blackwell LLP

(57) ABSTRACT

A novel organometallic complex having high color purity is provided. The organometallic complex includes a structure which includes iridium and a ligand and is represented by a general formula (G1). The ligand includes a pyrido[2,3-b]indole skeleton and a pyrimidine skeleton bonded to the 3-position of the pyrido[2,3-b]indole skeleton. The 2-position of the pyrido[2,3-b]indole skeleton and the pyrimidine skeleton are each bonded to the iridium. In the general formula (G1), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

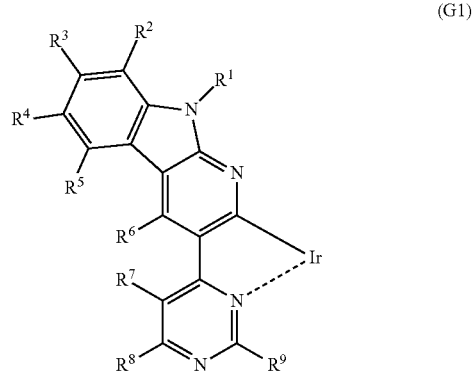

(G1)

25 Claims, 25 Drawing Sheets

ORGANOMETALLIC COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an organometallic complex. In particular, one embodiment of the present invention relates to an organometallic complex that can convert triplet excitation energy into light emission. In addition, one embodiment of the present invention relates to a light-emitting element, a light-emitting device, an electronic device, and a lighting device each including the organometallic complex. Note that one embodiment of the present invention is not limited to the above technical field. The technical field of one embodiment of the invention disclosed in this specification and the like relates to an object, a method, or a manufacturing method. Furthermore, one embodiment of the present invention relates to a process, a machine, manufacture, or a composition of matter. Specific examples of the technical field of one embodiment of the present invention disclosed in this specification include, in addition to the above, a semiconductor device, a display device, a liquid crystal display device, a power storage device, a memory device, a method for driving any of them, and a method for manufacturing any of them.

2. Description of the Related Art

A display including a light-emitting element having a structure in which an organic compound that is a light-emitting substance is provided between a pair of electrodes (also referred to as an organic EL element) has attracted attention as a next-generation flat panel display element in terms of characteristics of the light-emitting element, such as being thin and light in weight, high-speed response, and low voltage driving. When a voltage is applied to this light-emitting element, electrons and holes injected from the electrodes recombine to put the light-emitting substance into an excited state, and then light is emitted in returning from the excited state to the ground state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting element is considered to be S*:T*=1:3.

Among the above light-emitting substances, a compound capable of converting singlet excitation energy into light emission is called a fluorescent compound (fluorescent material), and a compound capable of converting triplet excitation energy into light emission is called a phosphorescent compound (phosphorescent material).

Accordingly, on the basis of the above generation ratio, the internal quantum efficiency (the ratio of the number of generated photons to the number of injected carriers) of a light-emitting element including a fluorescent material is thought to have a theoretical limit of 25%, while the internal quantum efficiency of a light-emitting element including a phosphorescent material is thought to have a theoretical limit of 75%.

In other words, a light-emitting element including a phosphorescent material has higher efficiency than a light-emitting element including a fluorescent material. Thus, various kinds of phosphorescent materials have been actively developed in recent years. An organometallic complex that contains iridium or the like as a central metal is particularly attracting attention because of its high phosphorescence quantum yield (see Patent Document 1, for example).

REFERENCE

Patent Document

[Patent Document 1] Japanese Published Patent Application No. 2009-023938

SUMMARY OF THE INVENTION

Although phosphorescent materials exhibiting excellent characteristics have been actively developed as disclosed in Patent Document 1, development of novel materials with better characteristics has been desired.

In view of the above, according to one embodiment of the present invention, a novel organometallic complex is provided. According to one embodiment of the present invention, a novel organometallic complex having high color purity is provided. According to one embodiment of the present invention, a novel organometallic complex that can be used in a light-emitting element is provided. According to one embodiment of the present invention, a novel organometallic complex that can be used in an EL layer of a light-emitting element is provided. According to one embodiment of the present invention, a novel light-emitting element is provided. In addition, according to one embodiment of the present invention, a novel light-emitting device, a novel electronic device, or a novel lighting device is provided. Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is an organometallic complex including iridium and a ligand. The ligand includes a pyrido[2,3-b]indole skeleton and a pyrimidine skeleton bonded to the 3-position of the pyrido[2,3-b]indole skeleton. The 2-position of the pyrido[2,3-b]indole skeleton and the pyrimidine skeleton are each bonded to the iridium.

Another embodiment of the present invention is an organometallic complex including iridium, and first and second ligands bonded to the iridium. The first ligand includes a pyrido[2,3-b]indole skeleton and a pyrimidine skeleton bonded to the 3-position of the pyrido[2,3-b]indole skeleton. The second ligand is a monoanionic bidentate chelate ligand having a β-diketone structure, a monoanionic bidentate chelate ligand having a carboxyl group, a monoanionic bidentate chelate ligand having a phenolic hydroxyl group, a monoanionic bidentate chelate ligand in which two ligand elements are both nitrogen, or an aromatic heterocyclic bidentate ligand which can form a metal-carbon bonding with iridium by cyclometalation. The 2-position of the pyrido[2,3-b]indole skeleton and the pyrimidine skeleton are each bonded to the iridium.

In each of the above structures, the 3-position of the pyrimidine skeleton is bonded to the iridium.

Another embodiment of the present invention is an organometallic complex having a structure represented by the following general formula (G1).

[Chemical formula 1]

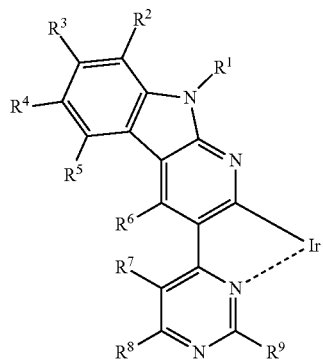
(G1)

Note that in the general formula (G1), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

Another embodiment of the present invention is an organometallic complex represented by the following general formula (G2).

[Chemical formula 2]

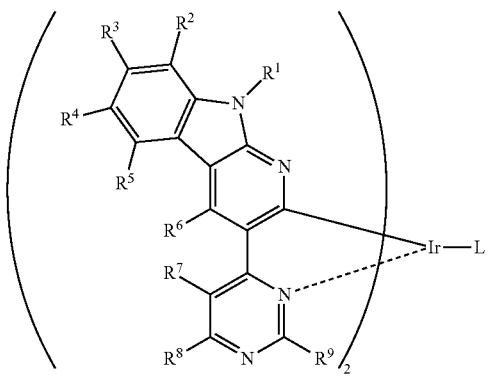
(G2)

Note that in the general formula (G2), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms; and L represents a monoanionic ligand.

In the above structure, the monoanionic ligand is a monoanionic bidentate chelate ligand having a β-diketone structure, a monoanionic bidentate chelate ligand having a carboxyl group, a monoanionic bidentate chelate ligand having a phenolic hydroxyl group, a monoanionic bidentate chelate ligand in which two ligand elements are both nitrogen, or an aromatic heterocyclic bidentate ligand which can form a metal-carbon bonding with iridium by cyclometalation.

In each of the above-described structures, the monoanionic ligand is represented by any one of the following general formulae (L1) to (L7).

[Chemical formulae 3]

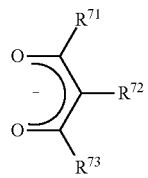
(L1)

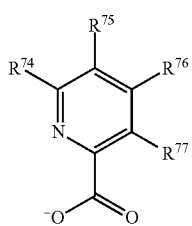
(L2)

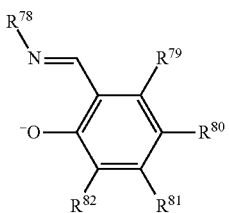
(L3)

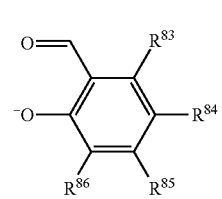
(L4)

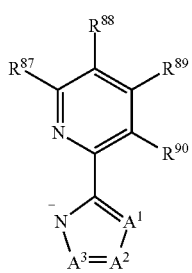
(L5)

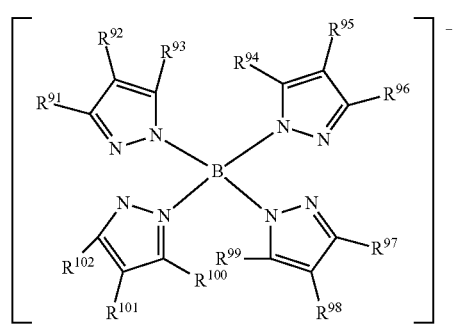
(L6)

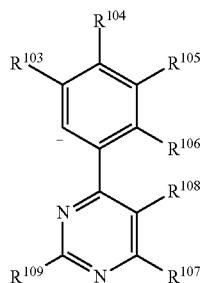

(L7)

In the general formulae (L1) to (L7), $R^{71}$ to $R^{109}$ each independently represent any of hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms. Each of $A^1$ to $A^3$ independently represents nitrogen, $sp^2$ hybridized carbon bonded to hydrogen, or $sp^2$ hybridized carbon having a substituent. The substituent is an alkyl group having 1 to 6 carbon atoms, a halogen group, a haloalkyl group having 1 to 6 carbon atoms, or a phenyl group.

Another embodiment of the present invention is an organometallic complex represented by the following general formula (G3).

[Chemical formula 4]

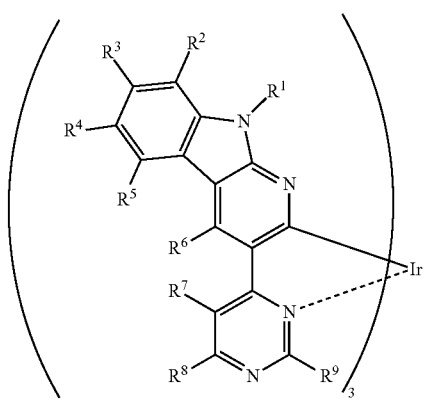

(G3)

Note that in the general formula (G3), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

Another embodiment of the present invention is an organometallic complex represented by the following general formula (G4).

[Chemical formula 5]

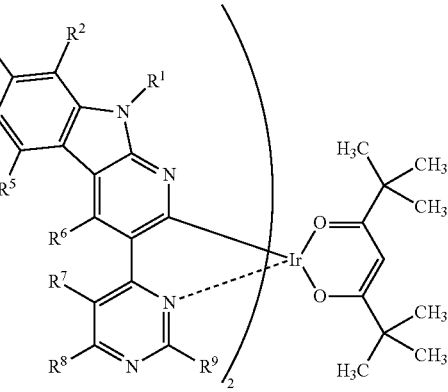

(G4)

Note that in the general formula (G4), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

Any of the above organometallic complexes each of which is one embodiment of the present invention has a structure in which the 3-position of the pyrido[2,3-b]indole skeleton and the pyrimidine skeleton included in the ligand are bonded to each other and the 2-position of the pyrido[2,3-b]indole skeleton and the pyrimidine skeleton are each bonded to the iridium which is the central metal. In the case where a pyridine ring included in the pyrido[2,3-b]indole skeleton is bonded to the iridium which is the central metal, the HOMO level and the LUMO level tend to be low. An organometallic complex with a low HOMO level has a problem of a low hole-injection property when it is used in an EL element, which results in reduction of the light-emitting efficiency of the light-emitting element. However, since the pyrido[2,3-b]indole skeleton of the organometallic complex of one embodiment of the present invention includes a nitrogen atom in a five-membered ring included in the skeleton, the HOMO level which tends to be too low due to the pyridine ring can be high. Accordingly, the hole-injection property can be prevented from decreasing. Furthermore, the high HOMO level of the organometallic complex can narrow the band gap. When the organometallic complex with a narrow band gap is used for an EL layer or the like of a light-emitting element, carriers (electrons or holes) can be easily injected and transported, and the driving voltage can be reduced. In addition, an emission spectrum of the organometallic complex of one embodiment of the present invention is shifted to a short wavelength side owing to the structure in which the 2-position of the pyrido[2,3-b] indole skeleton is bonded to the iridium which is the central metal, and the emission spectrum is comparatively narrowed. This is preferable because highly efficient light emission and green light with high color purity can be achieved.

Another embodiment of the present invention is an organometallic complex represented by the following structural formula (100).

[Chemical formula 6]

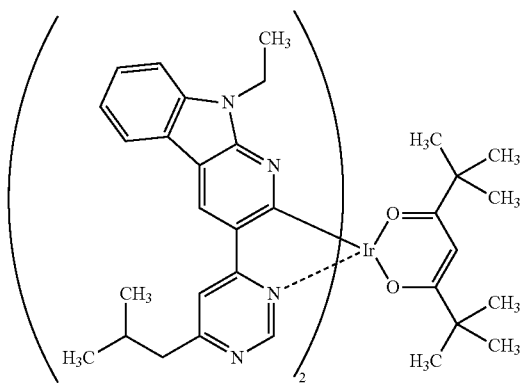
(100)

Another embodiment of the present invention is an organometallic complex represented by the following structural formula (112).

[Chemical formula 7]

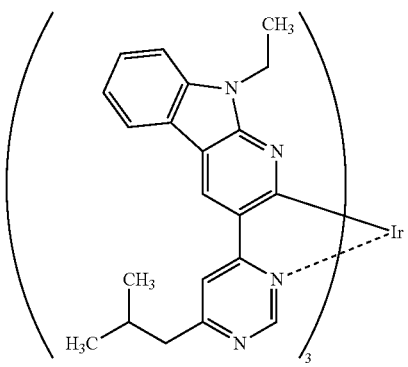
(112)

The organometallic complex which is one embodiment of the present invention is very effective for the following reason: the organometallic complex can emit phosphorescence, that is, it can provide luminescence from a triplet excited state, and can exhibit light emission, and therefore higher efficiency is possible when the organometallic complex is used in a light-emitting element. Thus, one embodiment of the present invention also includes a light-emitting element in which the organometallic complex of one embodiment of the present invention is used.

Another embodiment of the present invention is a light-emitting element including an EL layer between a pair of electrodes. The EL layer includes a light-emitting layer. The light-emitting layer includes any of the above organometallic complexes.

Another embodiment of the present invention is a light-emitting element including an EL layer between a pair of electrodes. The EL layer includes a light-emitting layer. The light-emitting layer includes a plurality of organic compounds. One of the plurality of organic compounds includes any of the above organometallic complexes.

One embodiment of the present invention includes, in its scope, not only a light-emitting device including the light-emitting element but also a lighting device including the light-emitting device. The light-emitting device in this specification refers to an image display device and a light source (e.g., a lighting device). In addition, the light-emitting device includes, in its category, all of a module in which a connector such as a flexible printed circuit (FPC) or a tape carrier package (TCP) is connected to a light-emitting device, a module in which a printed wiring board is provided on the tip of a TCP, and a module in which an integrated circuit (IC) is directly mounted on a light emitting element by a chip on glass (COG) method.

According to one embodiment of the present invention, a novel organometallic complex can be provided. According to one embodiment of the present invention, a novel organometallic complex having high color purity can be provided. According to one embodiment of the present invention, a novel organometallic complex that can be used in a light-emitting element can be provided. According to one embodiment of the present invention, a novel organometallic complex that can be used in an EL layer of a light-emitting element can be provided. According to one embodiment of the present invention, a novel light-emitting element including a novel organometallic complex can be provided. According to one embodiment of the present invention, a novel light-emitting device, a novel electronic device, or a novel lighting device can be provided. Note that the description of these effects does not preclude the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

In the accompanying drawings:
FIGS. 15A, 15B1, and 15B2 illustrate block diagrams of a display device.

DETAILED DESCRIPTION OF THE INVENTION

Figure 1A:
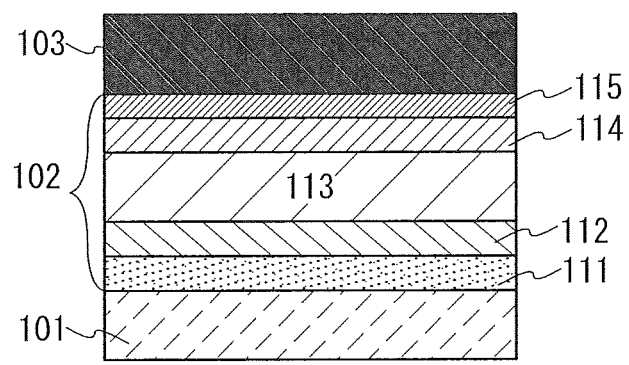
FIGS. 1A and 1B illustrate structures of light-emitting elements.

Embodiments and examples of the present invention will be described below with reference to the drawings. However, the present invention is not limited to the following description, and the mode and details can be variously changed unless departing from the scope and spirit of the present invention. Thus, the present invention should not be construed as being limited to the description in the following embodiments and examples.

Note that the terms "film" and "layer" can be interchanged with each other depending on the case or circumstances. For example, the term "conductive layer" can be changed into the term "conductive film" in some cases. Also, the term "insulating film" can be changed into the term "insulating layer" in some cases.

Embodiment 1

In this embodiment, organometallic complexes, each of which is one embodiment of the present invention, will be described.

An organometallic complex described in this embodiment includes iridium which is a central metal and a ligand. The ligand includes a pyrido[2,3-b]indole skeleton and a pyrimidine skeleton bonded to the 3-position of the pyrido[2,3-b]indole skeleton. The 2-position of the pyrido[2,3-b]indole skeleton and the pyrimidine skeleton are each bonded to the iridium.

An organometallic complex described in this embodiment includes iridium which is a central metal, and first and second ligands bonded to the iridium. The first ligand includes a pyrido[2,3-b]indole skeleton and a pyrimidine skeleton bonded to the 3-position of the pyrido[2,3-b]indole skeleton. The second ligand is a monoanionic bidentate chelate ligand having a β-diketone structure, a monoanionic bidentate chelate ligand having a carboxyl group, a monoanionic bidentate chelate ligand having a phenolic hydroxyl group, a monoanionic bidentate chelate ligand in which two ligand elements are both nitrogen, or an aromatic heterocyclic bidentate ligand which can form a metal-carbon bonding with iridium by cyclometalation. The 2-position of the pyrido[2,3-b]indole skeleton and the pyrimidine skeleton are each bonded to the iridium.

In each of the above structures, the 3-position of the pyrimidine skeleton is bonded to the iridium.

An organometallic complex described in this embodiment includes a structure represented by the following general formula (G1).

[Chemical formula 8]

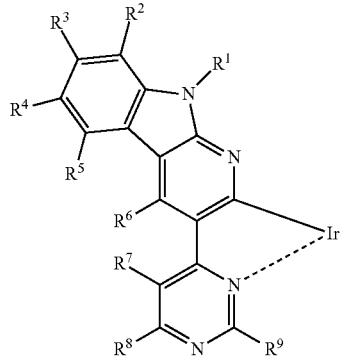

(G1)

Note that in the general formula (G1), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

An organometallic complex described in this embodiment is represented by following general formula (G2).

[Chemical formula 9]

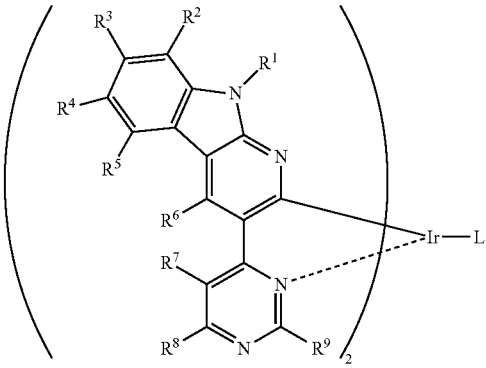

(G2)

Note that in the general formula (G2), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms; and L represents a monoanionic ligand.

In the above structure, the monoanionic ligand is a monoanionic bidentate chelate ligand having a β-diketone structure, a monoanionic bidentate chelate ligand having a carboxyl group, a monoanionic bidentate chelate ligand having a phenolic hydroxyl group, a monoanionic bidentate chelate ligand in which two ligand elements are both nitrogen, or an aromatic heterocyclic bidentate ligand which can form a metal-carbon bonding with iridium by cyclometalation.

In each of the above-described structures, the monoanionic ligand is represented by any one of the following general formulae (L1) to (L7).

[Chemical formulae 10]

(L1)
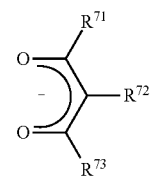

(L2)
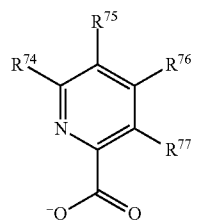

(L3)
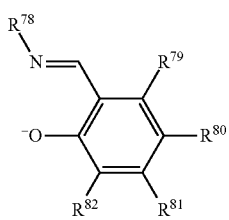

(L4)
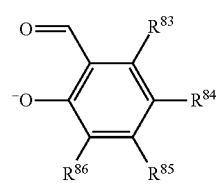

(L5)
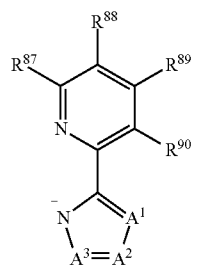

(L6)
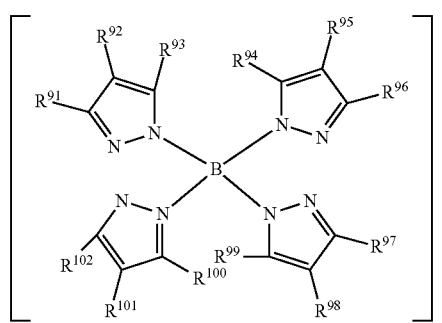

(L7)
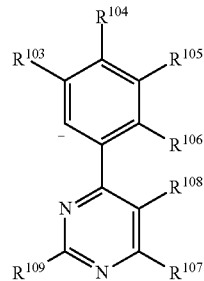

In the general formulae (L1) to (L7), $R^{71}$ to $R^{109}$ each independently represent any of hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms. Each of $A^1$ to $A^3$ independently represents nitrogen, $sp^2$ hybridized carbon bonded to hydrogen, or $sp^2$ hybridized carbon having a substituent. The substituent is an alkyl group having 1 to 6 carbon atoms, a halogen group, a haloalkyl group having 1 to 6 carbon atoms, or a phenyl group.

An organometallic complex described in this embodiment is represented by the following general formula (G3).

[Chemical formula 11]

(G3)
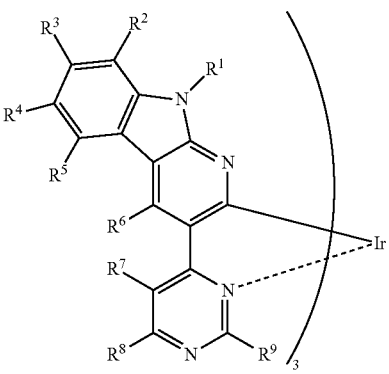

Note that in the general formula (G3), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

An organometallic complex described in this embodiment is represented by the following general formula (G4).

[Chemical formula 12]

(G4)

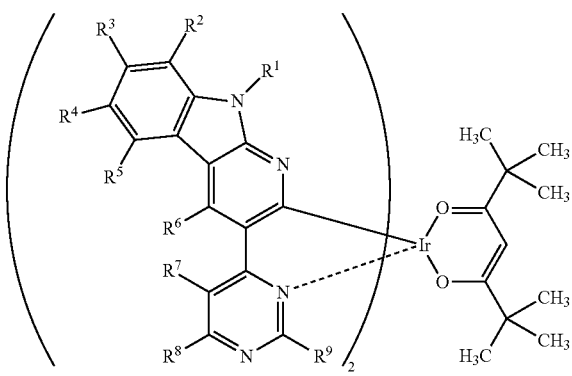

Note that in the general formula (G4), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

Note that in the case where the substituted or unsubstituted alkyl group having 1 to 6 carbon atoms, the substituted or unsubstituted aryl group having 6 to 13 carbon atoms, or the substituted or unsubstituted heteroaryl group having 3 to 12 carbon atoms in any of the above general formulae (G1) to (G4) has a substituent, examples of the substituent include an alkyl group having 1 to 6 carbon atoms, such as a methyl group, an ethyl group, a propyl group, an isopropyl group, a butyl group, an isobutyl group, a sec-butyl group, a tert-butyl group, a pentyl group, or a hexyl group; a cycloalkyl group having 5 to 7 carbon atoms, such as a cyclopentyl group, a cyclohexyl group, a cycloheptyl group, a 1-norbornyl group, or a 2-norbornyl group; and an aryl group having 6 to 12 carbon atoms, such as a phenyl group or a biphenyl group.

Specific examples of the alkyl group having 1 to 6 carbon atoms in $R^1$ to $R^9$ in each of the general formulae (G1) to (G4) include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, a 2,3-dimethylbutyl group, and a trifluoromethyl group.

Specific examples of the aryl group having 6 to 13 carbon atoms in $R^1$ to $R^9$ in each of the general formulae (G1) to (G4) include a phenyl group, a tolyl group (an o-tolyl group, an m-tolyl group, and a p-tolyl group), a naphthyl group (a 1-naphthyl group and a 2-naphthyl group), a biphenyl group (a biphenyl-2-yl group, a biphenyl-3-yl group, and a biphenyl-4-yl group), a xylyl group, a pentalenyl group, an indenyl group, a fluorenyl group, and a phenanthryl group. Note that the above substituents may be bonded to each other and form a ring. In such a case, for example, a spirofluorene skeleton is formed in such a manner that carbon at the 9-position of a fluorenyl group has two phenyl groups as substituents and these phenyl groups are bonded to each other.

Specific examples of the heteroaryl group having 3 to 12 carbon atoms in $R^1$ to $R^9$ in each of the general formulae (G1) to (G4) include an imidazolyl group, a pyrazolyl group, a pyridyl group, a pyridazyl group, a triazyl group, a benzimidazolyl group, and a quinolyl group.

Any of the organometallic complexes represented by the general formulae (G1) to (G4), each of which is one embodiment of the present invention, has a structure in which the 3-position of the pyrido[2,3-b]indole skeleton and the pyrimidine skeleton included in the ligand are bonded to each other and the 2-position of the pyrido[2,3-b]indole skeleton and the pyrimidine skeleton are each bonded to the iridium which is the central metal. In the case where a pyridine ring included in the pyrido[2,3-b]indole skeleton is bonded to the iridium which is the central metal, the HOMO level and the LUMO level tend to be low. An organometallic complex with a low HOMO level has a problem of a low hole-injection property when it is used in an EL element, which results in reduction of the light-emitting efficiency of the light-emitting element. However, since the pyrido[2,3-b]indole skeleton of the organometallic complex of one embodiment of the present invention includes a nitrogen atom in a five-membered ring included in the skeleton, the HOMO level which tends to be too low due to the pyridine ring can be high. Accordingly, the hole-injection property can be prevented from decreasing. Furthermore, the high HOMO level of the organometallic complex can narrow the band gap. When the organometallic complex with a narrow band gap is used for an EL layer or the like of a light-emitting element, carriers (electrons or holes) can be easily injected and transported, and the driving voltage can be reduced. In addition, an emission spectrum of the organometallic complex of one embodiment of the present invention is shifted to a short wavelength side owing to the structure in which the 2-position of the pyrido[2,3-b]indole skeleton is bonded to the iridium which is the central metal, and the emission spectrum is comparatively narrowed. This is preferable because highly efficient light emission and green light with high color purity can be achieved.

Next, specific structural formulae of the above-described organometallic complexes, each of which is one embodiment of the present invention, are shown below. Note that the present invention is not limited to these formulae.

[Chemical formulae 13]

(100)

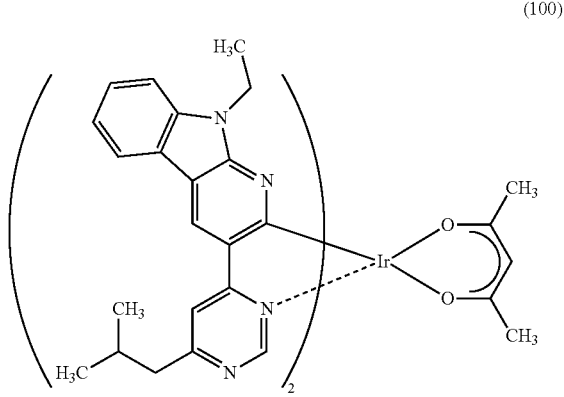

(101)
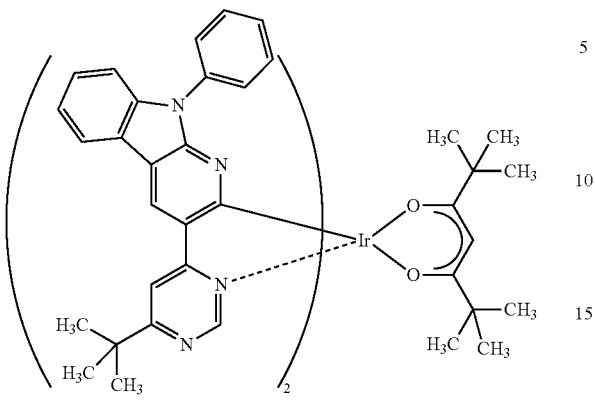
(104)
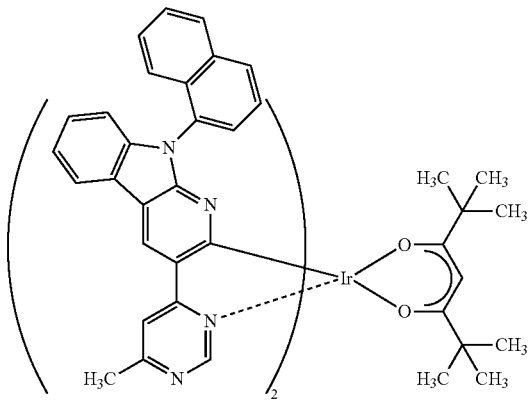
(102)
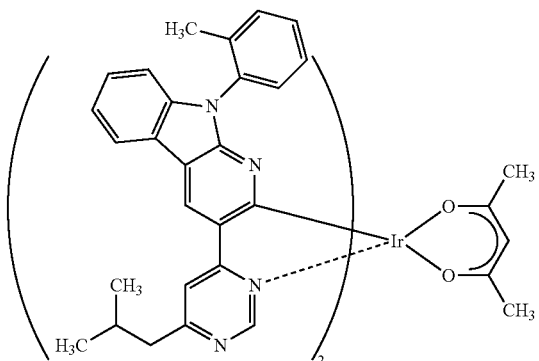
(105)
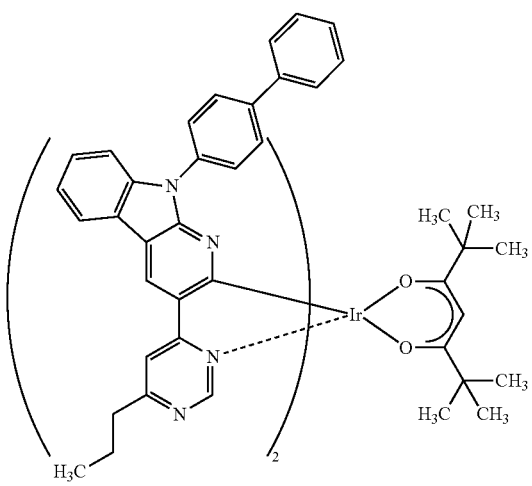
(103)
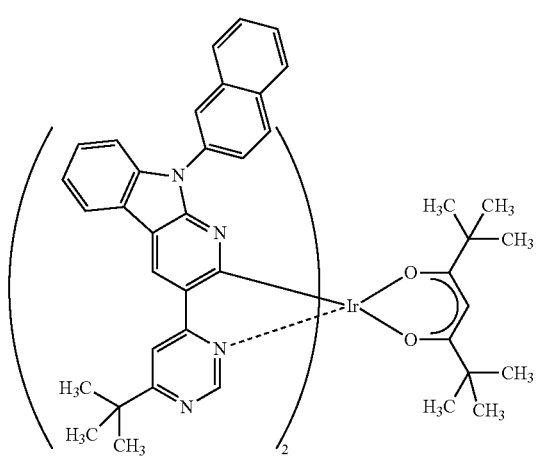
[Chemical formulae 14]
(106)
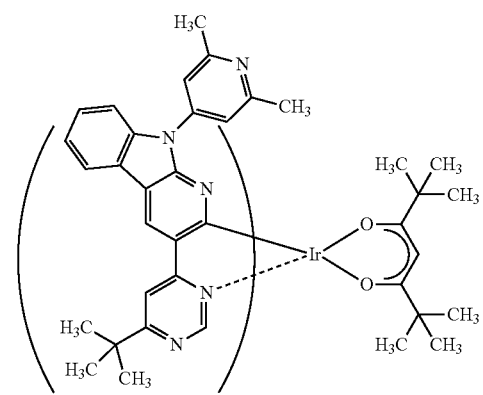

(107)
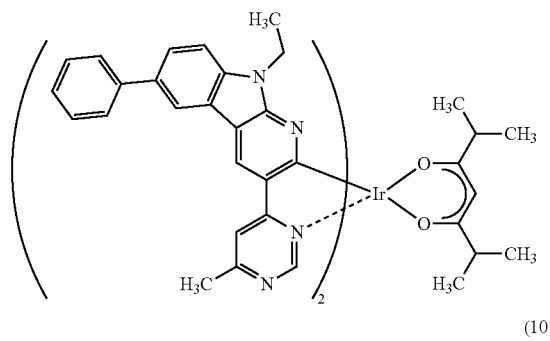
(108)
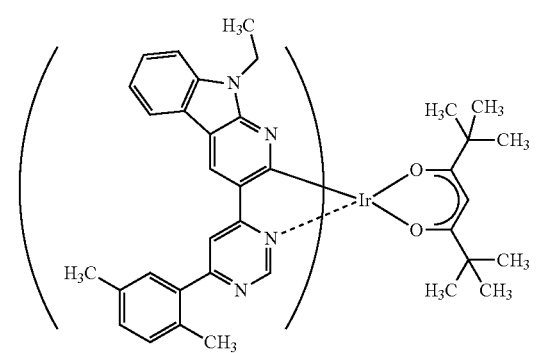
(109)
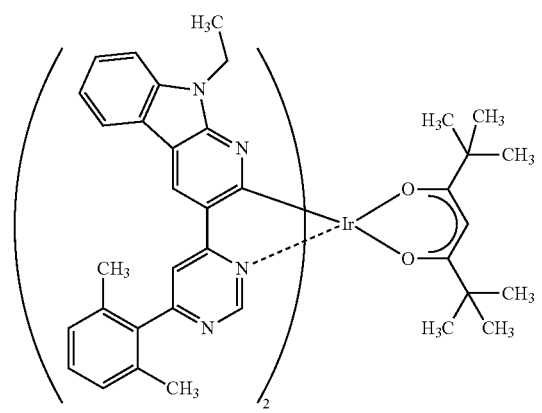
(110)
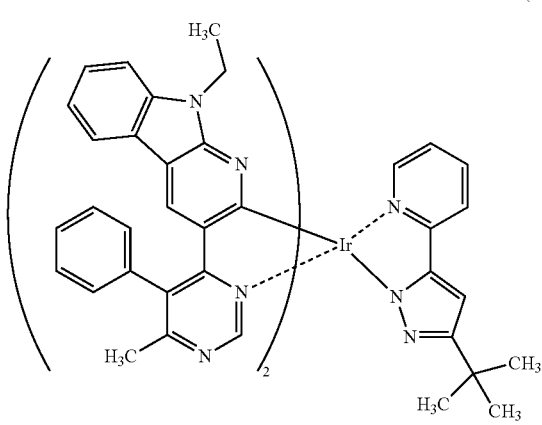
(111)
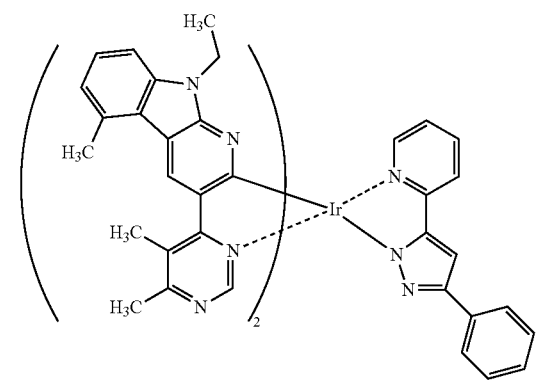
[Chemical formulae 15]
(112)
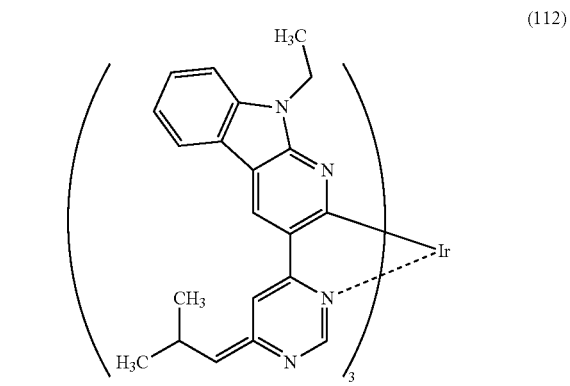
(113)
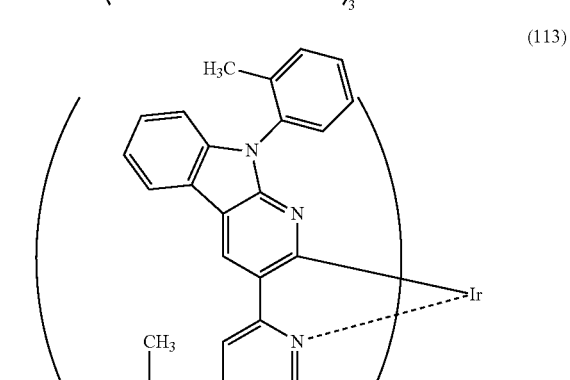
(114)
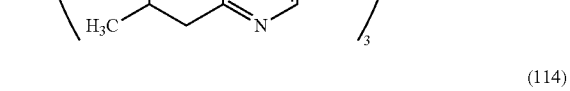

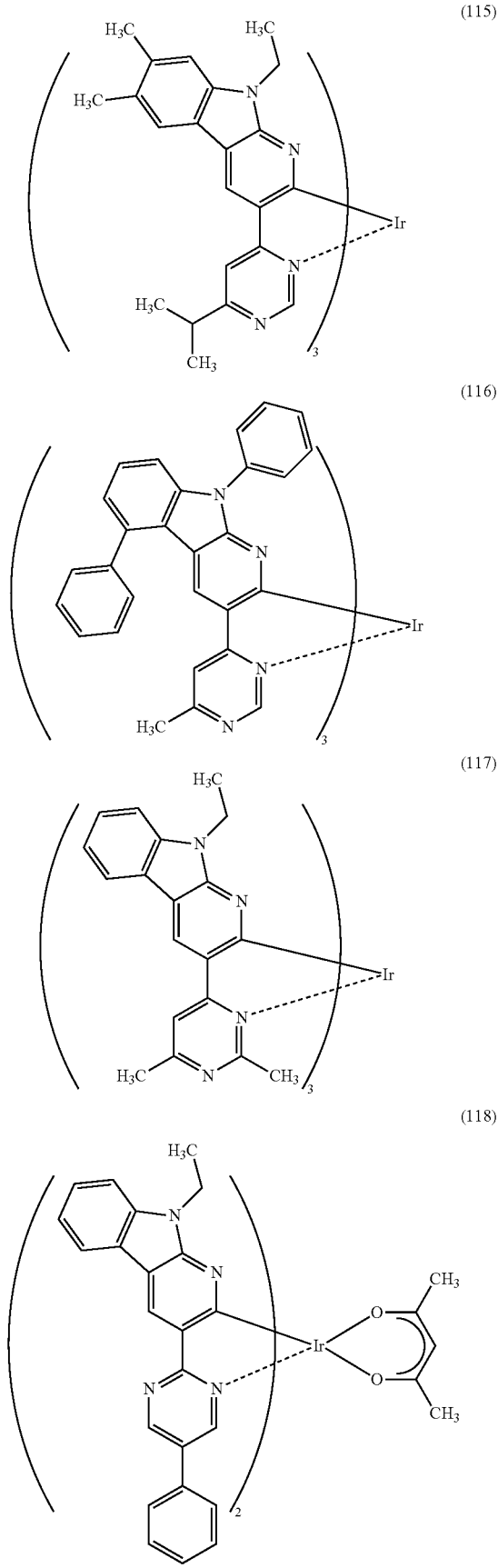
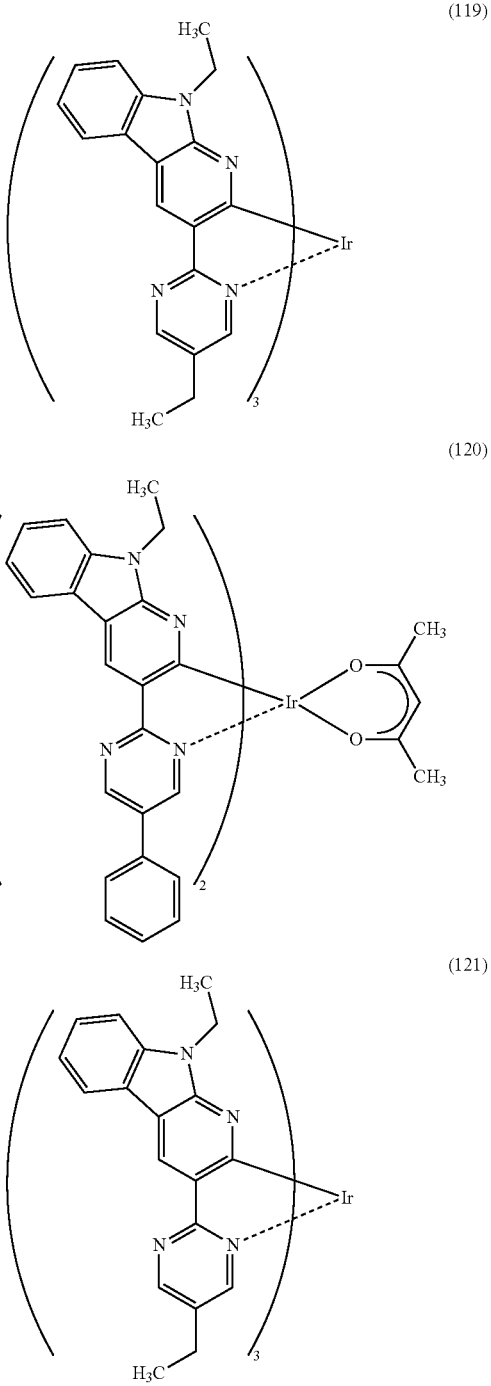

The organometallic complexes represented by the structural formulae (100) to (121) are novel substances capable of emitting phosphorescence. There can be geometrical isomers and stereoisomers of these substances depending on the type of the ligand. Each of the organometallic complexes which are embodiments of the present invention includes all of these isomers.

Next, an example of a method for synthesizing the organometallic complex which is one embodiment of the present invention and represented by the general formula (G1) is described.

<<Synthesis Method of Pyrimidine Derivative Represented by General Formula (G0)>>

A pyrimidine derivative represented by the following general formula (G0) can be synthesized by a simple synthesis scheme (A) or (A') as follows. In the synthesis scheme (A), Q represents halogen; $R^{31}$ represents a single bond, a methylene group, an ethylidene group, a propylidene group, an isopropylidene group, or the like; each of $R^{32}$ to $R^{35}$ is the same or different from one another and represents a hydrogen atom or an alkyl group having 1 to 3 carbon atoms; and $R^{33}$ and $R^{35}$ may be bonded to each other through a carbon chain to form a ring.

[Chemical formula 16]

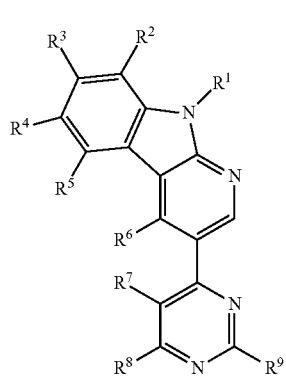

(G0)

In the general formula (G0), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

For example, as illustrated in the scheme (A), the pyrimidine derivative represented by the general formula (G0) can be obtained by coupling a boronic acid, a boronate ester, or a cyclic-triolborate salt (A1) with a halogenated pyrimidine compound (A2) and then coupling the obtained product with an organic halide (A3). As the cyclic-triolborate salt, a potassium salt, a lithium salt, a sodium salt, or the like can be used.

[Chemical formula 17]

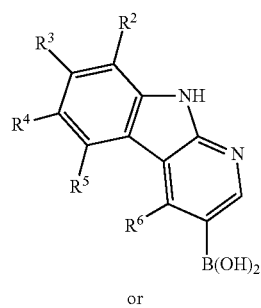

(A)

or

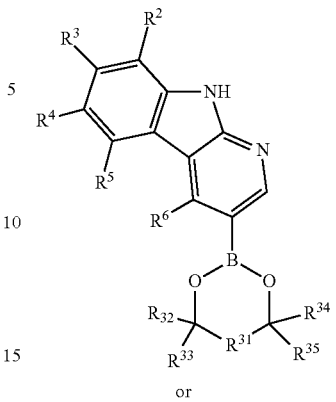

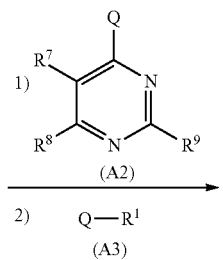

(A2)

2)  Q—$R^1$ (A3)

or

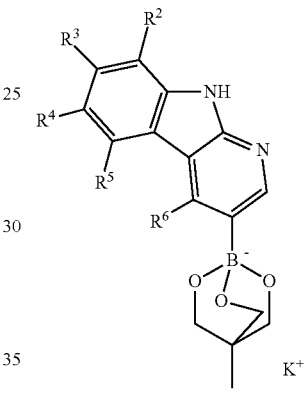

(A1)

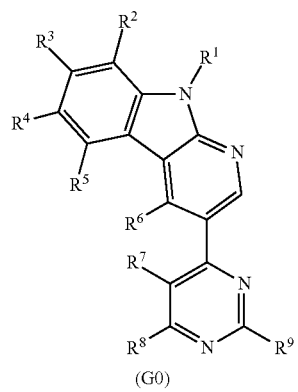

(G0)

Alternatively, as illustrated in the scheme (A'), the pyrimidine derivative represented by the general formula (G0) can be obtained by reacting a 1,3-diketone (A1') which is a pyrido[2,3-b]indole derivative with amidine (A2').

[Chemical formula 18]

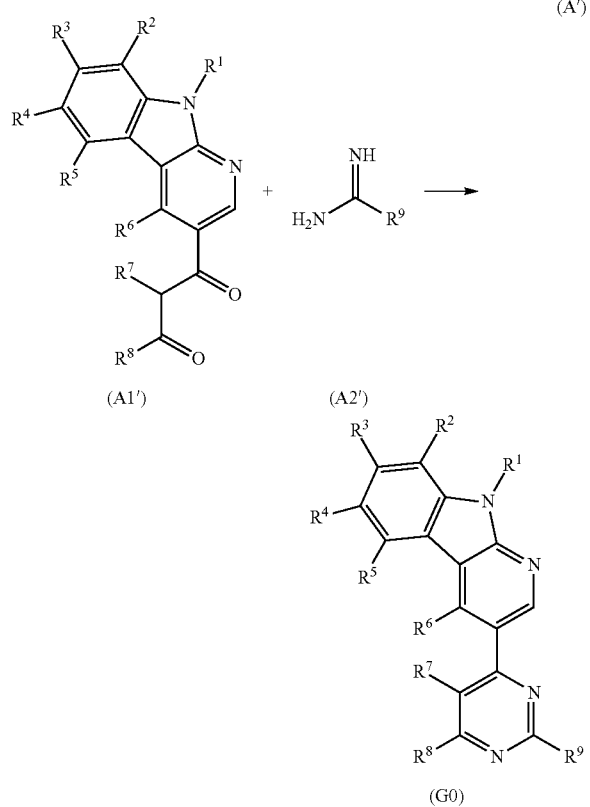

Since a wide variety of the compounds (A1), (A2), (A1'), and (A2') are commercially available or their synthesis is feasible, a great variety of the pyrimidine derivative represented by the general formula (G0) can be synthesized. Accordingly, the organometallic complexes described in this embodiment have wider variations of ligands.

<<Synthesis Method of Organometallic Complex Represented by General Formula (G2)>>

Next, a method for synthesizing the organometallic complex which is one embodiment of the present invention and represented by the general formula (G2) is described. First, as shown in the following synthesis scheme (B-1), the pyrimidine derivative represented by the general formula (G0) and an iridium metal compound containing halogen (e.g., iridium chloride, iridium bromide, iridium iodide, iridium acetate, or ammonium hexachloroiridate) are heated in an inert gas atmosphere by using no solvent, an alcohol-based solvent (e.g., glycerol, ethylene glycol, 2-methoxyethanol, or 2-ethoxyethanol) alone, or a mixed solvent of water and one or more kinds of such alcohol-based solvents, whereby a novel dinuclear complex (P), which is one type of organometallic complex having a halogen-bridged structure, can be obtained. There is no particular limitation on a heating means, and an oil bath, a sand bath, an aluminum block, or the like can be used. Alternatively, microwaves can be used as the heating means.

[Chemical formula 19]

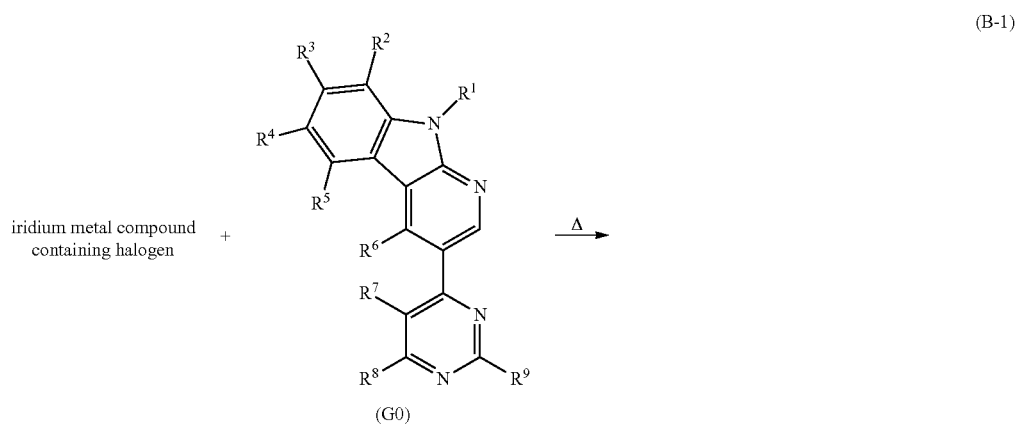

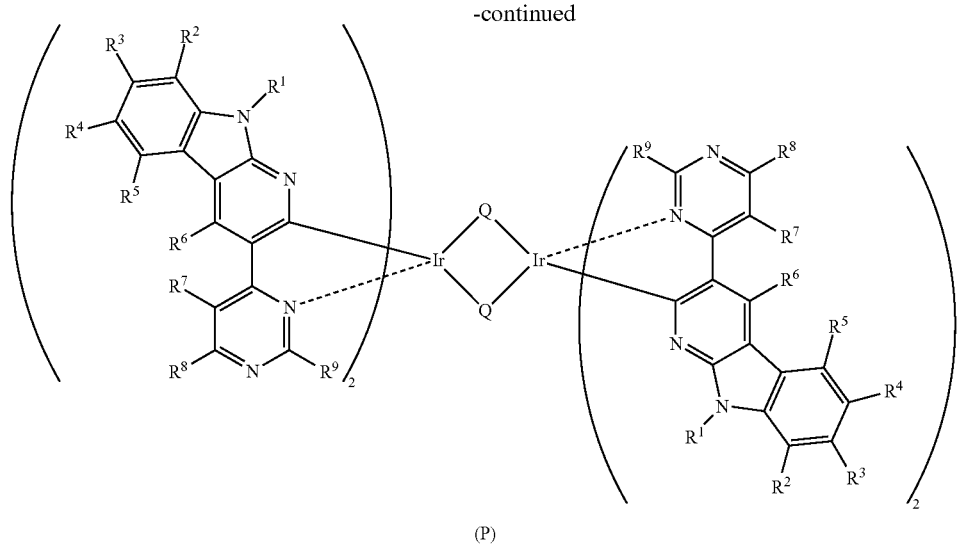

(P)

In the synthesis scheme (B-1), Q represents halogen, and $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

Then, as shown in the following synthesis scheme (B-2), the dinuclear complex (P) obtained in the synthesis scheme (B-1) is reacted with HL which is a material of a monoanionic ligand in an inert gas atmosphere, whereby a proton of HL is separated and L coordinates to the central metal, iridium. Thus, the organometallic complex represented by the general formula (G2) can be obtained.

[Chemical formula 20]

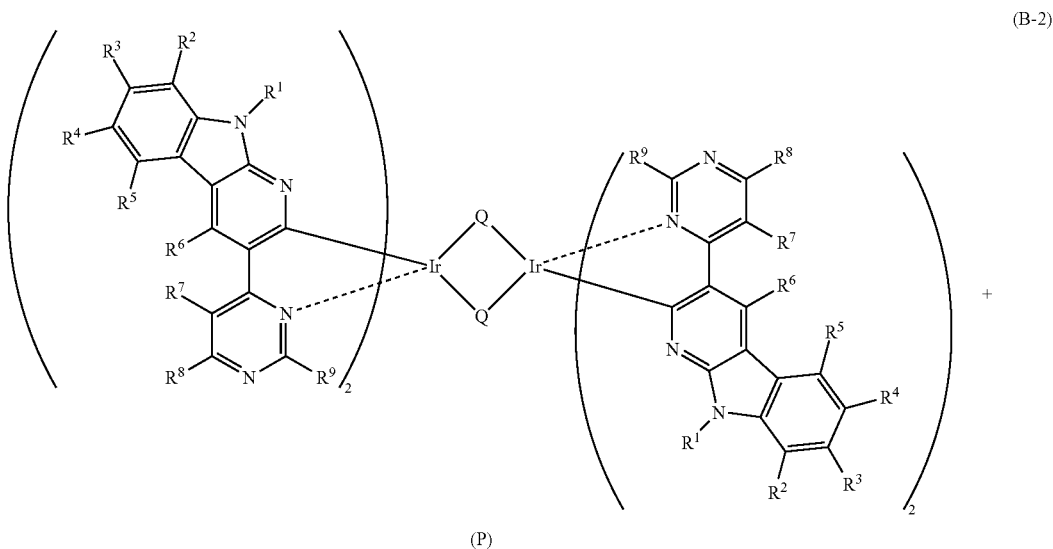

(B-2)

(P)

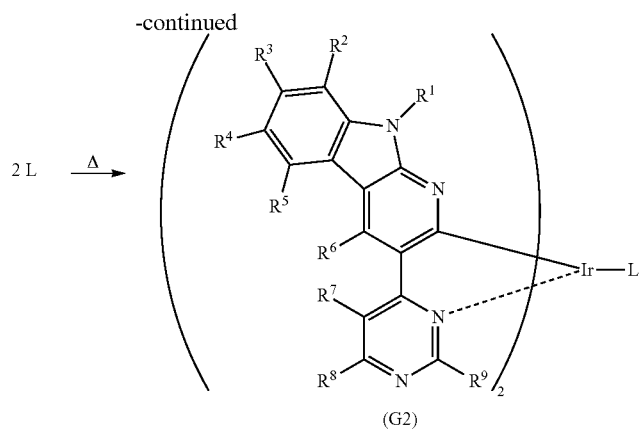

(G2)

In the synthesis scheme (B-2), L represents a monoanionic ligand, Q represents halogen, and $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms. In the above structure, the monoanionic ligand is a monoanionic bidentate chelate ligand having a β-diketone structure, a monoanionic bidentate chelate ligand having a carboxyl group, a monoanionic bidentate chelate ligand having a phenolic hydroxyl group, a monoanionic bidentate chelate ligand in which two ligand elements are both nitrogen, or an aromatic heterocyclic bidentate ligand which can form a metal-carbon bonding with iridium by cyclometalation.

<<Synthesis Method of Organometallic Complex Represented by General Formula (G3)>>

Next, a method for synthesizing the organometallic complex which is one embodiment of the present invention and represented by the general formula (G3) is described. As shown in a synthesis scheme (C), an iridium compound containing halogen (e.g., iridium chloride hydrate, iridium bromide, iridium iodide, iridium acetate, or ammonium hexachloroiridate) or an organoiridium complex compound (e.g., an acetylacetonato complex, a diethylsulfide complex, a di-µ-chloro bridged dinuclear complex, or a di-µ-hydroxo bridged dinuclear complex) is mixed with the pyrimidine derivative represented by the general formula (G0), the mixture is dissolved in an alcohol-based solvent (e.g., glycerol, ethylene glycol, 2-methoxyethanol, or 2-ethoxyethanol) or not dissolved in any solvent, and heating is performed. Thus, the organometallic complex represented by the general formula (G3) can be obtained.

[Chemical formula 21]

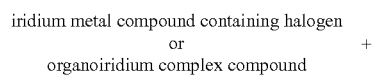

(C)

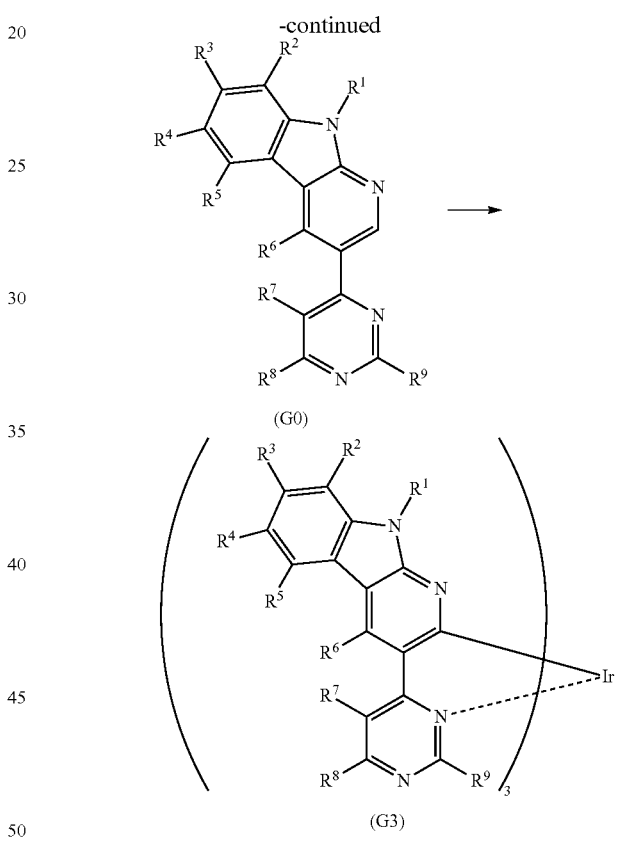

In the synthesis scheme (C), $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

The above is the description on the examples of methods for synthesizing the organometallic complexes of embodiments of the present invention; however, the present invention is not limited thereto and any other synthesis method may be employed.

The above-described organometallic complexes each of which is one embodiment of the present invention can emit phosphorescence and thus can be used as a light-emitting material or a light-emitting substance of a light-emitting element.

With the use of any of the organometallic complexes each of which is one embodiment of the present invention, a light-emitting element, a light-emitting device, an electronic device, or a lighting device with high emission efficiency can be obtained. Alternatively, it is possible to obtain a light-emitting element, a light-emitting device, an electronic device, or a lighting device with low power consumption.

In Embodiment 1, one embodiment of the present invention has been described. Other embodiments of the present invention are described in Embodiments 2 to 9. Note that one embodiment of the present invention is not limited to the above examples. In other words, various embodiments of the invention are described in this embodiment and the other embodiments, and one embodiment of the present invention is not limited to a particular embodiment. The example in which one embodiment of the present invention is used in a light-emitting element is described; however, one embodiment of the present invention is not limited thereto. Depending on circumstances or conditions, one embodiment of the present invention may be used in objects other than a light-emitting element.

The structures described in this embodiment can be used in appropriate combination with any of the structures described in the other embodiments.

Embodiment 2

In this embodiment, a light-emitting element which is one embodiment of the present invention will be described with reference to FIGS. 1A and 1B.

In the light-emitting element described in this embodiment, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

When a voltage is applied to the light-emitting element, holes injected from the first electrode 101 side and electrons injected from the second electrode 103 side recombine in the light-emitting layer 113; with energy generated by the recombination, a light-emitting substance such as the organometallic complex that is contained in the light-emitting layer 113 emits light.

The hole-injection layer 111 in the EL layer 102 can inject holes into the hole-transport layer 112 or the light-emitting layer 113 and can be formed of, for example, a substance having a high hole-transport property and a substance having an acceptor property, in which case electrons are extracted from the substance having a high hole-transport property by the substance having an acceptor property to generate holes. Thus, holes are injected from the hole-injection layer 111 into the light-emitting layer 113 through the hole-transport layer 112. For the hole-injection layer 111, a substance having a high hole-injection property can also be used. For example, molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: H$_2$Pc) and copper phthalocyanine (CuPc), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS).

A preferred specific example in which the light-emitting element described in this embodiment is fabricated is described below.

For the first electrode (anode) 101 and the second electrode (cathode) 103, a metal, an alloy, an electrically conductive compound, a mixture thereof, and the like can be used. Specific examples are indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg or AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method or an evaporation method (including a vacuum evaporation method).

As the substance having a high hole-transport property which is used for the hole-injection layer 111 and the hole-transport layer 112, any of a variety of organic compounds such as aromatic amine compounds, carbazole derivatives, aromatic hydrocarbons, and high molecular compounds (e.g., oligomers, dendrimers, or polymers) can be used. Specifically, a substance having a hole mobility of $1 \times 10^{-6}$ cm$^2$/Vs or more is preferably used. The layer formed using the substance having a high hole-transport property is not limited to a single layer and may be formed by stacking two or more layers. Organic compounds that can be used as the substance having a hole-transport property are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), DNTPD, 1,3,5-tris[N-(4-diphenylaminophenyl)-N-phenylamino]benzene (abbreviation: DPA3B), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like.

Specific examples of the carbazole derivatives are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like. Other examples are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbons are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon which has a hole mobility of $1\times10^{-6}$ cm$^2$/Vs or more and which has 14 to 42 carbon atoms is particularly preferable. The aromatic hydrocarbons may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl)phenyl]anthracene (abbreviation: DPVPA).

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Examples of the substance having an acceptor property which is used for the hole-injection layer 111 and the hole-transport layer 112 are compounds having an electron-withdrawing group (a halogen group or a cyano group) such as 7,7,8,8-tetracyano-2,3,5,6-tetrafluoroquinodimethane (abbreviation: F$_4$-TCNQ), chloranil, and 2,3,6,7,10,11-hexacyano-1,4,5,8,9,12-hexaazatriphenylene (HAT-CN). In particular, a compound in which electron-withdrawing groups are bonded to a condensed aromatic ring having a plurality of hetero atoms, like HAT-CN, is thermally stable and preferable. Oxides of metals belonging to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable since it is stable in the air, has a low hygroscopic property, and is easy to handle.

The light-emitting layer 113 contains a light-emitting substance, which may be a fluorescent substance or a phosphorescent substance. In the light-emitting element which is one embodiment of the present invention, the organometallic complex described in Embodiment 1 is preferably used as the light-emitting substance in the light-emitting layer 113. The light-emitting layer 113 preferably contains, as a host material, a substance having higher triplet excitation energy than this organometallic complex (guest material). Alternatively, the light-emitting layer 113 may contain, in addition to the light-emitting substance, two kinds of organic compounds that can form an excited complex (also called an exciplex) at the time of recombination of carriers (electrons and holes) in the light-emitting layer 113 (the two kinds of organic compounds may be any of the host materials as described above). In order to form an exciplex efficiently, it is particularly preferable to combine a compound which easily accepts electrons (a material having an electron-transport property) and a compound which easily accepts holes (a material having a hole-transport property). In the case where the combination of a material having an electron-transport property and a material having a hole-transport property which form an exciplex is used as a host material as described above, the carrier balance between holes and electrons in the light-emitting layer can be easily optimized by adjustment of the mixture ratio of the material having an electron-transport property and the material having a hole-transport property. The optimization of the carrier balance between holes and electrons in the light-emitting layer can prevent a region in which electrons and holes are recombined from existing on one side in the light-emitting layer. By preventing the region in which electrons and holes are recombined from existing on one side, the reliability of the light-emitting element can be improved.

As the compound that is preferably used to form the above exciplex and easily accepts electrons (the material having an electron-transport property), a π-electron deficient heteroaromatic compound such as a nitrogen-containing heteroaromatic compound, a metal complex, or the like can be used. Specific examples include metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)-phenyl]pyrimidine (abbreviation: 4,6mCzP2Pm); a heterocyclic compound having a triazine skeleton, such as 2-{4-[3-(N-phenyl-9H-carbazol-3-yl)-9H-carbazol-9-yl]phenyl}-4,6-diphenyl-1,3,5-triazine (abbreviation: PCCzPTzn); and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compounds having diazine skeletons, those having triazine skeletons, and those having pyridine skeletons are highly reliable and preferred. In particular, the heterocyclic compounds having diazine (pyrimidine or pyrazine) skeletons and those having triazine skeletons have a high electron-transport property and contribute to a decrease in drive voltage.

As the compound that is preferably used to form the above exciplex and easily accepts holes (the material having a hole-transport property), a π-electron rich heteroaromatic compound (e.g., a carbazole derivative or an indole derivative), an aromatic amine compound, or the like can be favorably used. Specific examples include compounds having aromatic amine skeletons, such as 2-[N-(9-phenylcarbazol-3-yl)-N-phenylamino]spiro-9,9'-bifluorene (abbreviation: PCASF), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), NPB, N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), BSPB, 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), PCzPCA1, 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), DNTPD, 3,6-bis[N-(4-diphenylaminophenyl)-N-(1-naphthyflamino]-9-phenylcarbazole (abbreviation: PCzTPN2), PCzPCA2, 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), N-(4-biphenyl)-N-(9,9-dimethyl-9H-fluoren-2-yl)-9-phenyl-9H-carbazol-3-amine (abbreviation: PCBiF), and N-(1,1'-biphenyl-4-yl)-N-[4-(9-phenyl-9H-carbazol-3-yl)phenyl]-9,9-dimethyl-9H-fluoren-2-amine (abbreviation: PCBBiF); compounds having carbazole skeletons, such as 1,3-bis(N-carbazolyl)benzene (abbreviation: mCP), CBP, 3,6-bis(3,5-diphenylphenyl)-9-phenylcarbazole (abbreviation: CzTP), and 9-phenyl-9H-3-(9-phenyl-9H-carbazol-3-yl)carbazole (abbreviation: PCCP); compounds having thiophene skeletons, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compounds having aromatic amine skeletons and the compounds having carbazole skeletons are preferred because these compounds are highly reliable, have a high hole-transport property, and contribute to a reduction in drive voltage.

Note that in the case where the light-emitting layer 113 contains the above-described organometallic complex (guest material) and the host material, phosphorescence with high emission efficiency can be obtained from the light-emitting layer 113.

Figure 1B:
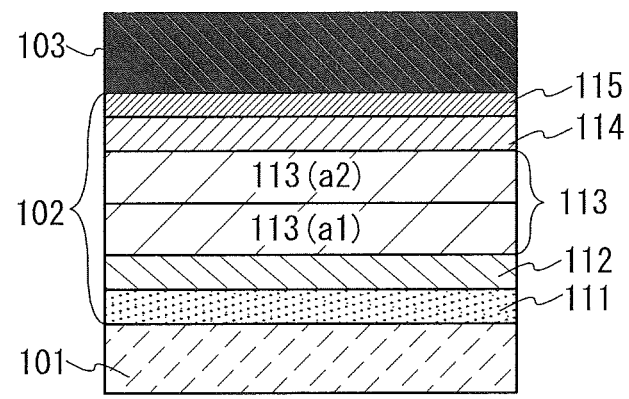

In the light-emitting element, the light-emitting layer 113 does not necessarily have the single-layer structure shown in FIG. 1A and may have a stacked-layer structure including two or more layers as shown in FIG. 1B. In that case, each layer in the stacked-layer structure emits light. For example, fluorescence is obtained from a first light-emitting layer 113($a$1), and phosphorescence is obtained from a second light-emitting layer 113($a$2) stacked over the first light-emitting layer. Note that the stacking order may be reversed. It is preferable that light emission due to energy transfer from an exciplex to a dopant be obtained from the layer that emits phosphorescence. The emission color of one layer and that of the other layer may be the same or different. In the case where the emission colors are different, a structure in which, for example, blue light from one layer and orange or yellow light or the like from the other layer can be obtained can be formed. Each layer may contain various kinds of dopants.

Note that in the case where the light-emitting layer 113 has a stacked-layer structure, for example, the organometallic complex described in Embodiment 1, a light-emitting substance converting singlet excitation energy into light emission, and a light-emitting substance converting triplet excitation energy into light emission can be used alone or in combination. In that case, the following substances can be used.

As an example of the light-emitting substance converting singlet excitation energy into light emission, a substance which emits fluorescence (a fluorescent compound) can be given.

Examples of the substance which emits fluorescence are N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation:

DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), {2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like.

Examples of the light-emitting substance converting triplet excitation energy into light emission are a substance which emits phosphorescence (a phosphorescent compound) and a thermally activated delayed fluorescent (TADF) material which emits thermally activated delayed fluorescence. Note that "delayed fluorescence" exhibited by the TADF material refers to light emission having the same spectrum as normal fluorescence and an extremely long lifetime. The lifetime is $1\times10^{-6}$ seconds or longer, preferably $1\times10^{-3}$ seconds or longer.

Examples of the substance which emits phosphorescence are bis{2-[3',5'-bis(trifluoromethyl)phenyl]pyridinato-N,C$^{2'}$}iridium(III) picolinate (abbreviation: [Ir(CF$_3$ppy)$_2$(pic)]), bis[2-(4',6'-difluorophenyl)pyridinato-N,C$^{2'}$]iridium (III) acetylacetonate (abbreviation: FIracac), tris(2-phenylpyridinato)iridium(III) (abbreviation: [Ir(ppy)$_3$]), bis(2-phenylpyridinato)iridium(III) acetylacetonate (abbreviation: [Ir(ppy)$_2$(acac)]), tris(acetylacetonato)(monophenanthroline)terbium(III) (abbreviation: [Tb(acac)$_3$(Phen)]), bis(benzo[h]quinolinato)iridium(III) acetylacetonate (abbreviation: [Ir(bzq)$_2$(acac)]), bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyephenyl]pyridinato-N,C$^{2'}$}iridium(III) acetylacetonate (abbreviation: [Ir(p-PF-ph)$_2$(acac)]), bis(2-phenylbenzothiazolato-N,C$^{2'}$)iridium(III) acetylacetonate (abbreviation: [Ir(bt)$_2$(acac)]), bis[2-(2'-benzo[4,5-a]thienyl)pyridinato-N,C$^{3'}$]iridium(III) acetylacetonate (abbreviation: [Ir(btp)$_2$(acac)]), bis(1-phenylisoquinolinato-N,C$^{2'}$)iridium(III) acetylacetonate (abbreviation: [Ir(piq)$_2$(acac)]), (acetylacetonato)bis[2,3-bis(4-fluorophenyl)quinoxalinato]iridium (III) (abbreviation: [Ir(Fdpq)$_2$(acac)]), (acetylacetonato)bis(3,5-dimethyl-2-phenylpyrazinato)iridium (III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato)(monophenanthroline)europium(III) (abbreviation: [Eu(DBM)$_3$(Phen)]), tris[1-(2-thenoyl)-3,3,3-trifluoroacetonato](monophenanthroline)europium(III) (abbreviation: [Eu(TTA)$_3$(Phen)]), and the like.

Examples of the TADF material are fullerene, a derivative thereof, an acridine derivative such as proflavine, eosin, and the like. Other examples are a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin are a protoporphyrin-tin fluoride complex (abbreviation: SnF$_2$(Proto IX)), a mesoporphyrin-tin fluoride complex (abbreviation: SnF$_2$(Meso IX)), a hematoporphyrin-tin fluoride complex (abbreviation: SnF$_2$(Hemato IX)), a coproporphyrin tetramethyl ester-tin fluoride complex (abbreviation: SnF$_2$(Copro III-4Me)), an octaethylporphyrin-tin fluoride complex (abbreviation: SnF$_2$(OEP)), an etioporphyrin-tin fluoride complex (abbreviation: SnF$_2$(Etio I)), an octaethylporphyrin-platinum chloride complex (abbreviation: PtCl$_2$OEP), and the like. Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (abbreviation: PIC-TRZ). Note that a material in which the π-electron rich heteroaromatic ring is directly bonded to the π-electron deficient heteroaromatic ring is particularly preferably used because both the donor property of the π-electron rich heteroaromatic ring and the acceptor property of the π-electron deficient heteroaromatic ring are increased and the energy difference between the S1 level and the T1 level becomes small.

The light-emitting layer 113 can be formed using a quantum dot (QD) having unique optical characteristics. Note that QD means a nanoscale semiconductor crystal. Specifically, the nanoscale semiconductor crystal has a diameter of several nanometers to several tens of nanometers. Furthermore, by using a crystal having a different size, the optical characteristics and the electronic characteristics can be changed, and thus an emission color or the like can be adjusted easily. A quantum dot has an emission spectrum with a narrow peak, and thus emission of light with high color purity can be obtained.

Examples of a material forming a quantum dot include a Group 14 element in the periodic table, a Group 15 element in the periodic table, a Group 16 element in the periodic table, a compound of a plurality of Group 14 elements in the periodic table, a compound of an element belonging to any of Groups 4 to 14 in the periodic table and a Group 16 element in the periodic table, a compound of a Group 2 element in the periodic table and a Group 16 element in the periodic table, a compound of a Group 13 element in the periodic table and a Group 15 element in the periodic table, a compound of a Group 13 element in the periodic table and a Group 17 element in the periodic table, a compound of a Group 14 element in the periodic table and a Group 15 element in the periodic table, a compound of a Group 11 element in the periodic table and a Group 17 element in the periodic table, iron oxides, titanium oxides, spinel chalcogenides, and semiconductor clusters.

Specific examples include, but are not limited to, cadmium selenide; cadmium sulfide; cadmium telluride; zinc selenide; zinc oxide; zinc sulfide; zinc telluride; mercury sulfide; mercury selenide; mercury telluride; indium arsenide; indium phosphide; gallium arsenide; gallium phosphide; indium nitride; gallium nitride; indium antimonide; gallium antimonide; aluminum phosphide; aluminum arsenide; aluminum antimonide; lead selenide; lead telluride; lead sulfide; indium selenide; indium telluride; indium sulfide; gallium selenide; arsenic sulfide; arsenic selenide; arsenic telluride; antimony sulfide; antimony selenide; antimony telluride; bismuth sulfide; bismuth selenide; bismuth telluride; silicon; silicon carbide; germanium; tin; selenium; tellurium; boron; carbon; phosphorus; boron nitride; boron phosphide; boron arsenide; aluminum nitride; aluminum sulfide; barium sulfide; barium selenide; barium telluride; calcium sulfide; calcium selenide; calcium telluride; beryllium sulfide; beryllium selenide; beryllium telluride; magnesium sulfide; magnesium selenide; germanium sulfide; germanium selenide; germanium telluride; tin sulfide; tin selenide; tin telluride; lead oxide; copper fluoride; copper chloride; copper bromide; copper iodide; copper oxide; copper selenide; nickel oxide; cobalt oxide; cobalt sulfide; iron oxide; iron sulfide; manganese oxide; molybdenum sulfide; vanadium oxide; tungsten oxide; tantalum oxide; titanium oxide; zirconium oxide; silicon nitride; germanium nitride; aluminum oxide; barium titanate; a compound of selenium, zinc, and cadmium; a compound of indium, arsenic, and phosphorus; a compound of cadmium, selenium, and sulfur; a compound of cadmium, selenium, and tellurium; a compound of indium, gallium, and arsenic; a compound of indium, gallium, and selenium; a compound of indium, selenium, and sulfur; a compound of copper, indium, and sulfur; and combinations thereof. What is called an alloyed quantum dot, whose composition is represented by a given ratio, may be used. For example, an alloyed quantum dot of cadmium, selenium, and sulfur is an effective material to obtain blue light because the emission wavelength can be changed by changing the percentages of the elements.

As a structure of a quantum dot, a core structure, a core-shell structure, a core-multishell structure, or the like can be given, and any of the structures may be used. Note that a core-shell quantum dot or a core-multishell quantum dot where a shell covers a core is preferable because a shell formed of an inorganic material having a wider band gap than an inorganic material used as the core can reduce the influence of defects and dangling bonds existing at the surface of the nanocrystal and significantly improve the quantum efficiency of light emission.

Moreover, QD can be dispersed into a solution, and thus the light-emitting layer 113 can be formed by a coating method, an inkjet method, a printing method, or the like. Note that QD can emit not only light with bright and vivid color but also light with a wide range of wavelengths and has high efficiency and long lifetime. Thus, when QD is included in the light-emitting layer 113, the element characteristics can be improved.

The electron-transport layer 114 is a layer containing a substance having a high electron-transport property (also referred to as an electron-transport compound). For the electron-transport layer 114, a metal complex such as tris (8-quinolinolato)aluminum (abbreviation: $Alq_3$), tris(4-methyl-8-quinolinolato)aluminum (abbreviation: $Almq_3$), $BeBq_2$, BAlq, bis[2-(2-hydroxyphenyl)benzoxazolato]zinc (abbreviation: $Zn(BOX)_2$), or bis[2-(2-hydroxyphenyl)benzothiazolato]zinc (abbreviation: $Zn(BTZ)_2$) can be used. Alternatively, a heteroaromatic compound such as PBD, OXD-7, TAZ, 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl) stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used. The substances listed here are mainly ones that have an electron mobility of $1 \times 10^{-6}$ cm$^2$/Vs or higher. Note that any substance other than the substances listed here may be used for the electron-transport layer 114 as long as the electron-transport property is higher than the hole-transport property.

The electron-transport layer 114 is not limited to a single layer, and may be a stack of two or more layers each containing any of the substances listed above.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride ($CaF_2$), or lithium oxide ($LiO_x$) can be used. A rare earth metal compound like erbium fluoride ($ErF_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that each of the hole-injection layer 111, the hole-transport layer 112, the light-emitting layer 113, the electron-transport layer 114, and the electron-injection layer 115 can be formed by any one or any combination of the following methods: an evaporation method (including a vacuum evaporation method), a printing method (such as relief printing, intaglio printing, gravure printing, planography printing, and stencil printing), an ink jet method, a coating method, and the like. Besides the above-mentioned materials, an inorganic compound such as a quantum dot or a high molecular compound (e.g., an oligomer, a dendrimer, or a polymer) may be used for the hole-injection layer 111, the hole-transport layer 112, the light-emitting layer 113, the electron-transport layer 114, and the electron-injection layer 115, which are described above.

In the above-described light-emitting element, current flows due to a potential difference applied between the first electrode 101 and the second electrode 103 and holes and electrons recombine in the EL layer 102, whereby light is emitted. Then, the emitted light is extracted outside through one or both of the first electrode 101 and the second electrode 103. Thus, one or both of the first electrode 101 and the second electrode 103 are electrodes having light-transmitting properties.

The above-described light-emitting element can emit phosphorescence originating from the organometallic complex and thus can have higher efficiency than a light-emitting element using only a fluorescent compound.

The structure described in this embodiment can be used in appropriate combination with any of the structures described in the other embodiments.

Embodiment 3

In this embodiment, a light-emitting element (hereinafter referred to as a tandem light-emitting element) which is one embodiment of the present invention and includes a plurality of EL layers is described.

Figure 2A:
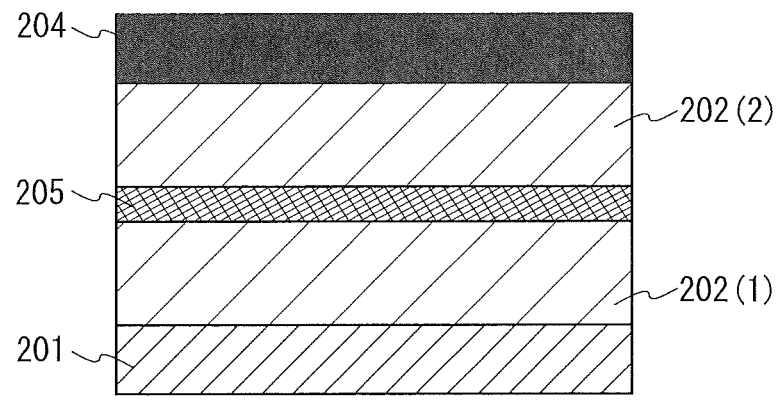
FIGS. 2A and 2B illustrate structures of light-emitting elements.

A light-emitting element described in this embodiment is a tandem light-emitting element including, between a pair of electrodes (a first electrode 201 and a second electrode 204), a plurality of EL layers (a first EL layer 202(1) and a second EL layer 202(2)) and a charge-generation layer 205 provided therebetween, as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, either or both of the EL layers (the first EL layer 202(1) and the second EL layer 202(2)) may have structures similar to those described in Embodiment 2. In other words, the structures of the first EL layer 202(1) and the second EL layer 202(2) may be the same or different from each other. When the structures are the same, Embodiment 2 can be referred to.

The charge-generation layer 205 provided between the plurality of EL layers (the first EL layer 202(1) and the second EL layer 202(2)) has a function of injecting electrons into one of the EL layers and injecting holes into the other of the EL layers when a voltage is applied between the first electrode 201 and the second electrode 204. In this embodiment, when a voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, the substances having a high hole-transport property which are given in Embodiment 2 as the substances used for the hole-injection layer 111 and the hole-transport layer 112 can be used. For example, an aromatic amine compound such as NPB, TPD, TDATA, MTDATA, or BSPB, or the like can be used. The substances listed here are mainly ones that have a hole mobility of $1 \times 10^4$ cm$^2$Ns or higher. Note that any organic compound other than the compounds listed here may be used as long as the hole-transport property is higher than the electron-transport property.

As the electron acceptor, 7,7,8,8-tetracyano-2,3,5,6-tetrafluoroquinodimethane (abbreviation: F$_4$-TCNQ), chloranil, and the like can be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable since it is stable in the air, has a low hygroscopic property, and is easy to handle.

In the case of the structure in which an electron donor is added to an organic compound having a high electron-transport property, as the organic compound having a high electron-transport property, the substances having a high electron-transport property which are given in Embodiment 2 as the substances used for the electron-transport layer 114 can be used. For example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, Bphen, BCP, or the like can be used. The substances listed here are mainly ones that have an electron mobility of $1 \times 10^{-6}$ cm$^2$/Vs or higher. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 205 by using any of the above materials can suppress a drive voltage increase caused by the stack of the EL layers. The charge-generation layer 205 can be formed by any one or any combination of the following methods: an evaporation method (including a vacuum evaporation method), a printing method (such as relief printing, intaglio printing, gravure printing, planography printing, and stencil printing), an ink-jet method, a coating method, and the like.

Figure 2B:
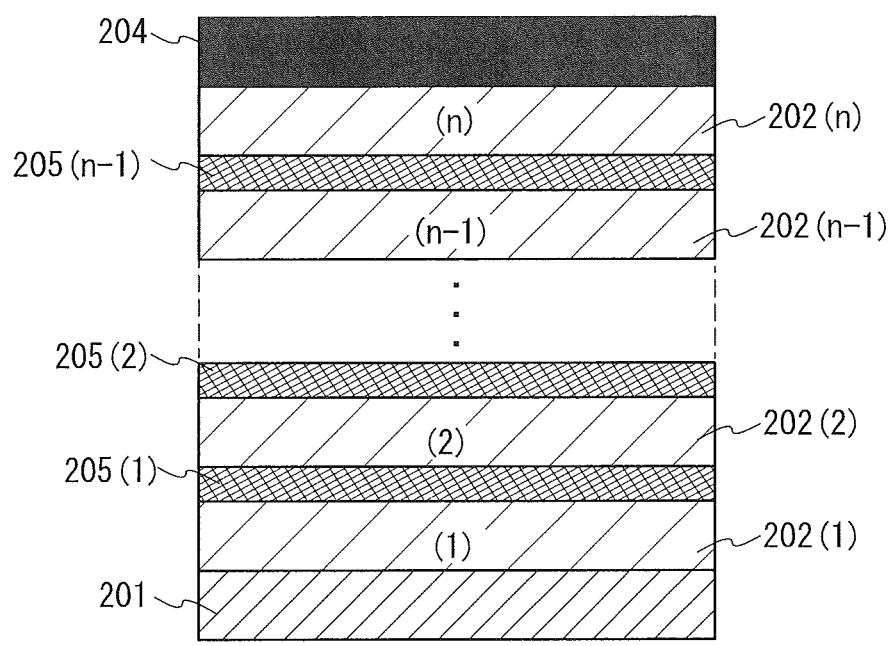

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are included between a pair of electrodes as in the light-emitting element according to this embodiment, by providing charge-generation layers (205(1) to 205(n−1)) between the EL layers, light emission in a high luminance region can be obtained with current density kept low. Since the current density can be kept low, the element can have a long lifetime.

When the EL layers have different emission colors, a desired emission color can be obtained from the whole light-emitting element. For example, in a light-emitting element having two EL layers, when an emission color of the first EL layer and an emission color of the second EL layer are complementary colors, the light-emitting element can emit white light as a whole. Note that "complementary colors" refer to colors that can produce an achromatic color when mixed. In other words, mixing light of complementary colors allows white light emission to be obtained. Specifically, a combination in which blue light emission is obtained from the first EL layer and yellow or orange light emission is obtained from the second EL layer is given as an example. In that case, it is not necessary that both of blue light emission and yellow (or orange) light emission are fluorescence, and the both are not necessarily phosphorescence. For example, a combination in which blue light emission is fluorescence and yellow (or orange) light emission is phosphorescence or a combination in which blue light emission is phosphorescence and yellow (or orange) light emission is fluorescence may be employed.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 4

In this embodiment, a light-emitting device which is one embodiment of the present invention is described.

The light-emitting device may be either a passive matrix light-emitting device or an active matrix light-emitting device. Any of the light-emitting elements described in other embodiments can be used for the light-emitting device described in this embodiment.

In this embodiment, first, an active matrix light-emitting device is described with reference to FIGS. 3A to 3C.

Figure 3A:
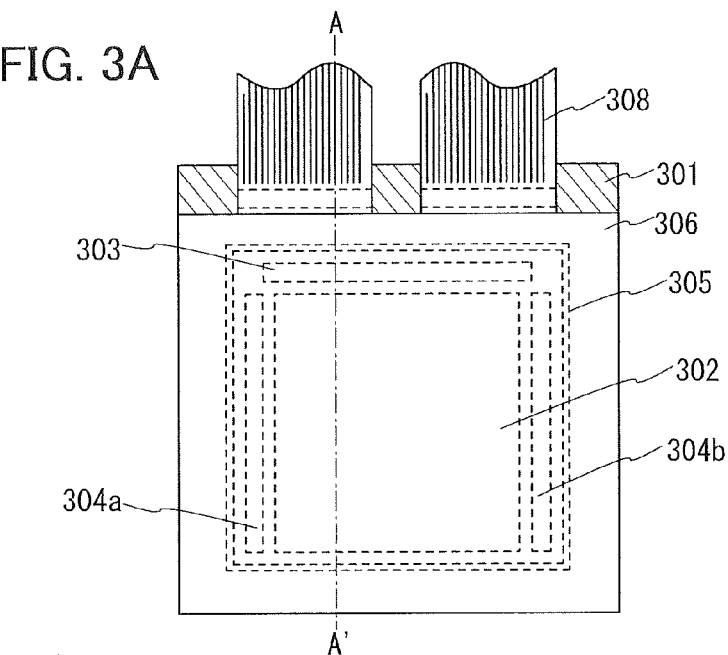
FIGS. 3A to 3C illustrate light-emitting devices.
Figure 3B:
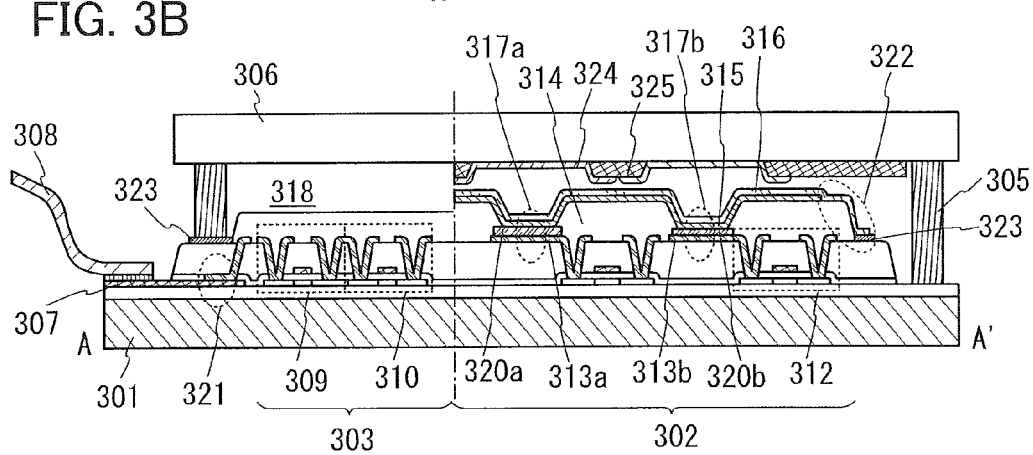

Note that FIG. 3A is a top view illustrating a light-emitting device and FIG. 3B is a cross-sectional view taken along the chain line A-A' in FIG. 3A. The light-emitting device according to this embodiment includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, or a reset signal) or a potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portions and the pixel portion are formed over the element substrate 301; the driver circuit portion 303 that is the source line driver circuit and the pixel portion 302 are illustrated here.

The driver circuit portion 303 is an example in which an FET 309 and an FET 310 are combined. Note that the driver circuit portion 303 may be formed with a circuit including transistors having the same conductivity type (either n-channel transistors or p-channel transistors) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a switching FET (not shown) and a current control FET 312, and a wiring of the current control FET 312 (a source electrode or a drain electrode) is electrically connected to first electrodes (anodes) (313a and 313b) of light-emitting elements 317a and 317b. Although the pixel portion 302 includes two FETs (the switching FET and the current control FET 312) in this embodiment, one embodiment of the present invention is not limited thereto. The pixel portion 302 may include, for example, three or more FETs and a capacitor in combination.

As the FETs 309, 310, and 312, for example, a staggered transistor or an inverted staggered transistor can be used. Examples of a semiconductor material that can be used for the FETs 309, 310, and 312 include Group 13 semiconductors, Group 14 semiconductors (e.g., silicon), compound semiconductors, oxide semiconductors, and organic semiconductors. In addition, there is no particular limitation on the crystallinity of the semiconductor, and an amorphous semiconductor or a crystalline semiconductor can be used. In particular, an oxide semiconductor is preferably used for the FETs 309, 310, and 312. Examples of the oxide semiconductor are In—Ga oxides, In-M-Zn oxides (M is Al, Ga, Y, Zr, La, Ce, Hf, or Nd), and the like. For example, an oxide semiconductor that has an energy gap of 2 eV or more, preferably 2.5 eV or more, further preferably 3 eV or more is used for the FETs 309, 310, and 312, so that the off-state current of the transistors can be reduced.

In addition, conductive films (320a and 320b) for optical adjustment are stacked over the first electrodes 313a and 313b. For example, as illustrated in FIG. 3B, in the case where the wavelengths of light extracted from the light-emitting elements 317a and 317b are different from each other, the thicknesses of the conductive films 320a and 320b are different from each other. In addition, an insulator 314 is formed to cover end portions of the first electrodes (313a and 313b). In this embodiment, the insulator 314 is formed using a positive photosensitive acrylic resin. The first electrodes (313a and 313b) are used as anodes in this embodiment.

The insulator 314 preferably has a surface with curvature at an upper end portion or a lower end portion thereof. This enables the coverage with a film to be formed over the insulator 314 to be favorable. The insulator 314 can be formed using, for example, either a negative photosensitive resin or a positive photosensitive resin. The material for the insulator 314 is not limited to an organic compound and an inorganic compound such as silicon oxide, silicon oxynitride, or silicon nitride can also be used.

An EL layer 315 and a second electrode 316 are stacked over the first electrodes (313a and 313b). In the EL layer 315, at least a light-emitting layer is provided. In the light-emitting elements (317a and 317b) including the first electrodes (313a and 313b), the EL layer 315, and the second electrode 316, an end portion of the EL layer 315 is covered with the second electrode 316. The structure of the EL layer 315 may be the same as or different from the single-layer structure and the stacked layer structure described in Embodiments 2 and 3. Furthermore, the structure may differ between the light-emitting elements.

For the first electrodes (313a and 313b), the EL layer 315, and the second electrode 316, any of the materials given in Embodiment 2 can be used. The first electrodes (313a and 313b) of the light-emitting elements (317a and 317b) are electrically connected to the lead wiring 307 in a region 321, so that an external signal is input through the FPC 308. The second electrode 316 in the light-emitting elements (317a and 317b) is electrically connected to a lead wiring 323 in a region 322, so that an external signal is input through the FPC 308 that is not illustrated in the figure.

Although the cross-sectional view in FIG. 3B illustrates only the two light-emitting elements (317a and 317b), a plurality of light-emitting elements are arranged in a matrix in the pixel portion 302. Specifically, in the pixel portion 302, light-emitting elements that emit light of two kinds of colors (e.g., B and Y), light-emitting elements that emit light of three kinds of colors (e.g., R, G, and B), light-emitting elements that emit light of four kinds of colors (e.g., (R, G, B, and Y) or (R, G, B, and W)), or the like are formed so that a light-emitting device capable of full color display can be obtained. In such cases, full color display may be achieved as follows: materials different according to the emission colors or the like of the light-emitting elements are used to form light-emitting layers (so-called separate coloring formation); alternatively, the plurality of light-emitting elements share one light-emitting layer formed using the same material and further include color filters. Thus, the light-emitting elements that emit light of a plurality of kinds of colors are used in combination, so that effects such as an improvement in color purity and a reduction in power consumption can be achieved. Furthermore, the light-emitting device may have improved emission efficiency and reduced power consumption by combination with quantum dots.

The sealing substrate 306 is attached to the element substrate 301 with the sealant 305, whereby the light-emitting elements 317a and 317b are provided in a space 318 surrounded by the element substrate 301, the sealing substrate 306, and the sealant 305.

The sealing substrate 306 is provided with coloring layers (color filters) 324, and a black layer (black matrix) 325 is provided between adjacent coloring layers. Note that one or both of the adjacent coloring layers (color filters) 324 may be provided so as to partly overlap with the black layer (black matrix) 325. Light emission obtained from the light-emitting elements 317a and 317b is extracted through the coloring layers (color filters) 324.

Note that the space 318 may be filled with an inert gas (such as nitrogen or argon) or the sealant 305. In the case where the sealant is applied for attachment of the substrates, one or more of UV treatment, heat treatment, and the like are preferably performed.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), poly(vinyl fluoride) (PVF), polyester, an acrylic resin, or the like can be used. In the case where glass frit is used as the sealant, the element substrate 301 and the sealing substrate 306 are preferably glass substrates for high adhesion.

Figure 3C:
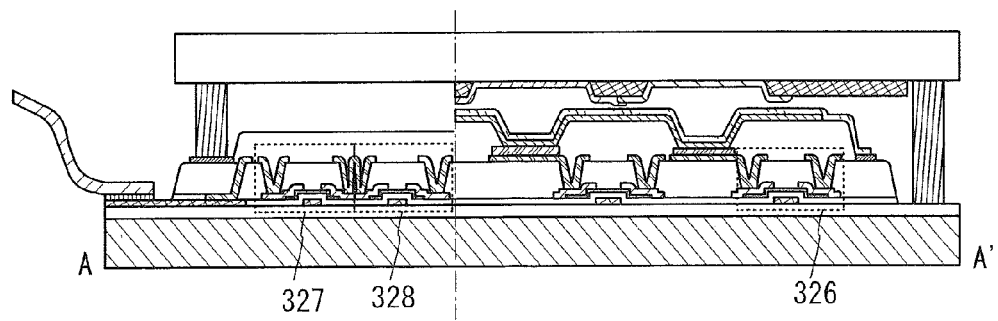

Structures of the FETs electrically connected to the light-emitting elements may be different from those in FIG. 3B in the position of a gate electrode; that is, the structures may be the same as those of an FET 326, an FET 327, and an FET 328, as illustrated in FIG. 3C. The coloring layer (color filter) 324 with which the sealing substrate 306 is provided may be provided as illustrated in FIG. 3C such that, at a position where the coloring layer (color filter) 324 overlaps with the black layer (black matrix) 325, the coloring layer (color filter) 324 further overlaps with an adjacent coloring layer (color filter) 324.

As described above, the active matrix light-emitting device can be obtained.

The light-emitting device which is one embodiment of the present invention may be of the passive matrix type, instead of the active matrix type described above.

Figure 4A:
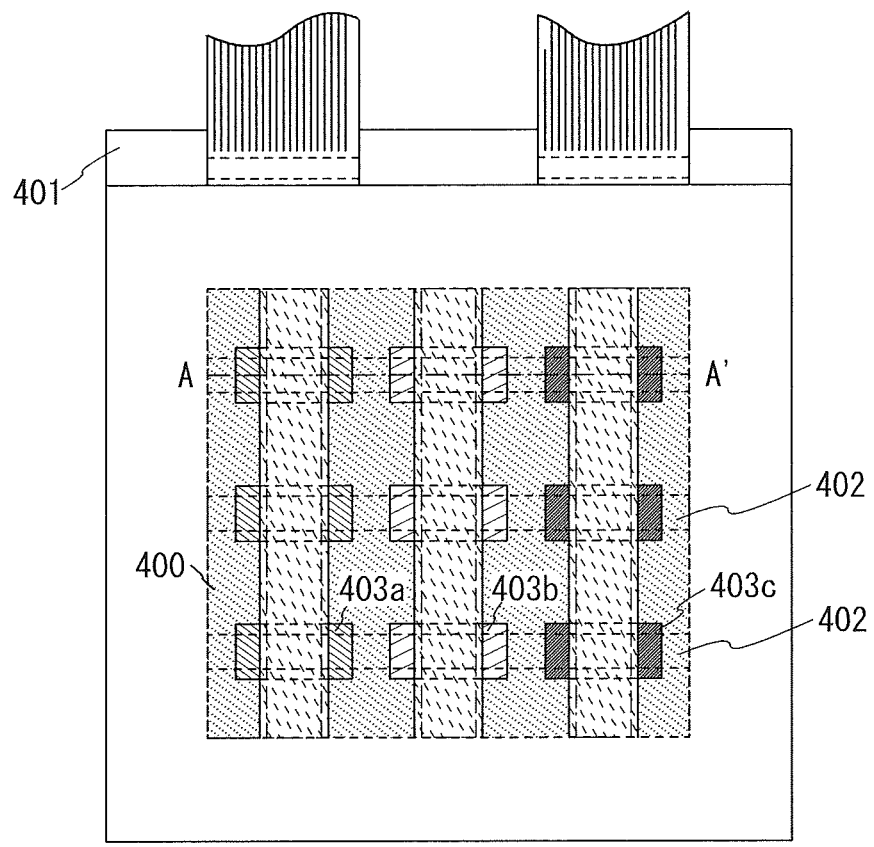
FIGS. 4A and 4B illustrate a light-emitting device.
Figure 4B:
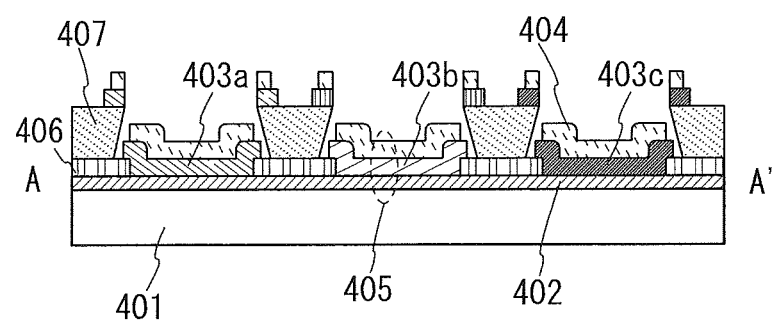

FIGS. 4A and 4B illustrate a passive matrix light-emitting device. FIG. 4A is a top view of the passive matrix light-emitting device, and FIG. 4B is a cross-sectional view thereof.

As illustrated in FIGS. 4A and 4B, light-emitting elements 405 including a first electrode 402, EL layers (403a, 403b, and 403c), and second electrodes 404 are formed over a substrate 401. Note that the first electrode 402 has an island-like shape, and a plurality of the first electrodes 402 are formed in one direction (the lateral direction in FIG. 4A) to form a striped pattern. An insulating film 406 is formed over part of the first electrode 402. A partition 407 formed using an insulating material is provided over the insulating film 406. The sidewalls of the partition 407 slope so that the distance between one sidewall and the other sidewall gradually decreases toward the surface of the substrate as illustrated in FIG. 4B.

Since the insulating film 406 includes openings over the part of the first electrode 402, the EL layers (403a, 403b, and 403c) and second electrodes 404 which are divided as desired can be formed over the first electrode 402. In the example in FIGS. 4A and 4B, a mask such as a metal mask and the partition 407 over the insulating film 406 are employed to form the EL layers (403a, 403b, and 403c) and the second electrodes 404. In this example, the EL layer 403a, the EL layer 403b, and the EL layer 403c emit light of different colors (e.g., red, green, blue, yellow, orange, and white).

After the formation of the EL layers (403a, 403b, and 403c), the second electrodes 404 are formed. Thus, the second electrodes 404 are formed over the EL layers (403a, 403b, and 403c) without contact with the first electrode 402.

Note that sealing can be performed by a method similar to that used for the active matrix light-emitting device, and description thereof is not made.

As described above, the passive matrix light-emitting device can be obtained.

Note that in this specification and the like, a transistor or a light-emitting element can be formed using any of a variety of substrates, for example. The type of substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As an example of a glass substrate, a barium borosilicate glass substrate, an aluminoborosilicate glass substrate, a soda lime glass substrate, or the like can be given. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a synthetic resin such as acrylic. Alternatively, polypropylene, polyester, polyvinyl fluoride, polyvinyl chloride, or the like can be used. Alternatively, polyamide, polyimide, aramid, epoxy, an inorganic vapor deposition film, paper, or the like can be used. Specifically, the use of semiconductor substrates, single crystal substrates, SOI substrates, or the like enables the manufacture of small-sized transistors with a small variation in characteristics, size, shape, or the like and with high current supply capability. A circuit using such transistors achieves lower power consumption of the circuit or higher integration of the circuit.

Alternatively, a flexible substrate may be used as the substrate, and a transistor or a light-emitting element may be provided directly on the flexible substrate. Still alternatively, a separation layer may be provided between the substrate and the transistor or the light-emitting element. The separation layer can be used when part or the whole of a semiconductor device formed over the separation layer is separated from the substrate and transferred onto another substrate. In such a case, the transistor or the light-emitting element can be transferred to a substrate having low heat resistance or a flexible substrate. For the separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of a substrate to which a transistor or a light-emitting element is transferred are, in addition to the above-described substrates over which a transistor or a light-emitting element can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, a rubber substrate, and the like. When such a substrate is used, a transistor with excellent characteristics or a transistor with low power consumption can be formed, a device with high durability or high heat resistance can be provided, or a reduction in weight or thickness can be achieved.

Note that the structure described in this embodiment can be combined as appropriate with any of the structures described in other embodiments.

Embodiment 5

In this embodiment, examples of a variety of electronic devices and an automobile manufactured using a light-emitting device which is one embodiment of the present invention are described.

Examples of the electronic device including the light-emitting device are television devices (also referred to as TV or television receivers), monitors for computers and the like, cameras such as digital cameras and digital video cameras, digital photo frames, cellular phones (also referred to as mobile phones or portable telephone devices), portable game consoles, portable information terminals, audio playback devices, large game machines such as pachinko machines, and the like. Specific examples of the electronic devices are illustrated in FIGS. 5A, 5B, 5C, 5D, 5D'-1, and 5D'-2 and FIGS. 6A to 6C.

Figure 5A:
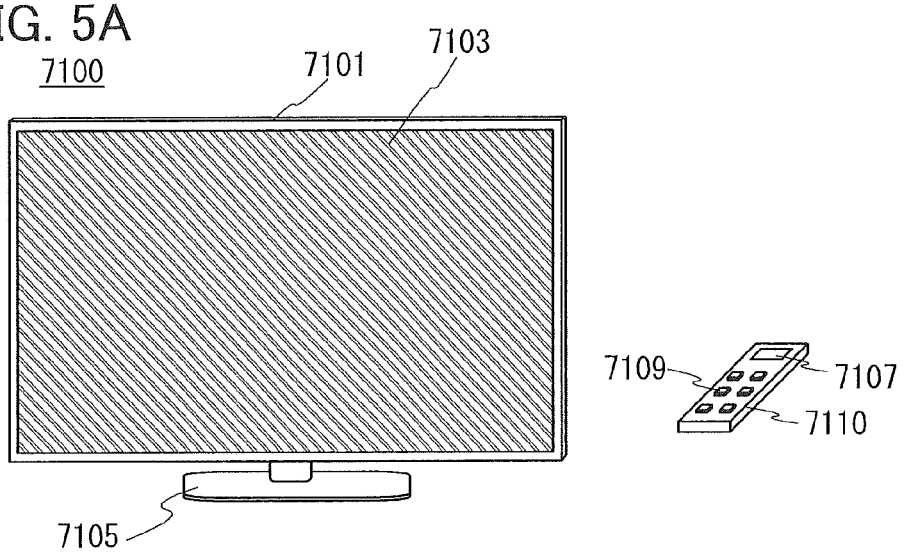
FIGS. 5A, 5B, 5C, 5D, 5D'-1, and 5D'-2 illustrate electronic devices.

FIG. 5A illustrates an example of a television device. In the television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 5B:
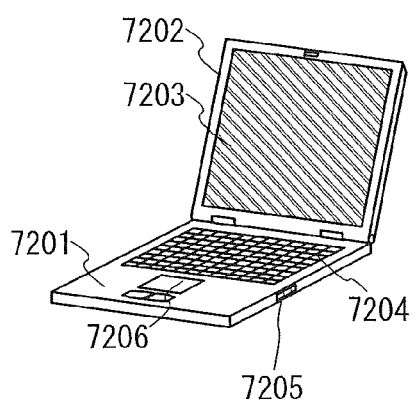

FIG. 5B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

Figure 5C:
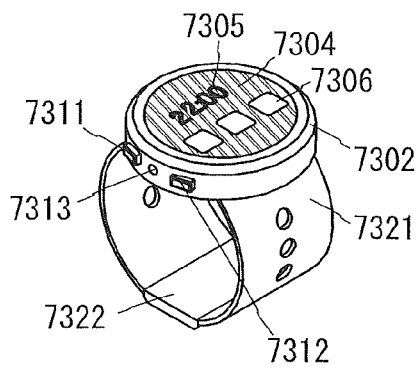

FIG. 5C illustrates a smart watch, which includes a housing 7302, a display portion 7304, operation buttons 7311 and 7312, a connection terminal 7313, a band 7321, a clasp 7322, and the like.

The display portion 7304 mounted in the housing 7302 serving as a bezel includes a non-rectangular display region. The display portion 7304 can display an icon 7305 indicating time, another icon 7306, and the like. The display portion 7304 may be a touch panel (an input/output device) including a touch sensor (an input device).

The smart watch illustrated in FIG. 5C can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display portion 7304.

Figure 5D:
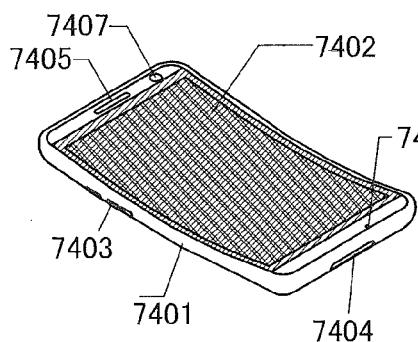
Figure 5D:
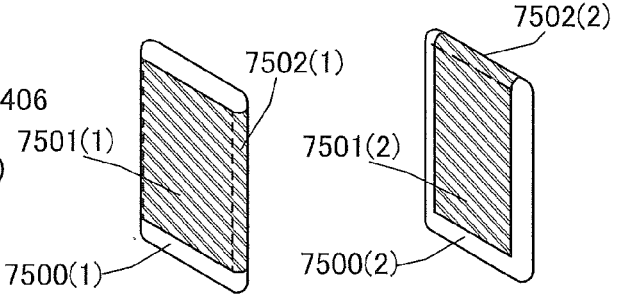

FIGS. 5D, 5D'-1, and 5D'-2 illustrate an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming the light-emitting element of one embodiment of the present invention over a flexible substrate, the light-emitting device can be used for the display portion 7402 having a curved surface as illustrated in FIG. 5D.

When the display portion 7402 of the cellular phone 7400 illustrated in FIG. 5D is touched with a finger or the like, data can be input to the cellular phone 7400. In addition, operations such as making a call and composing e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or composing e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 5D'-1 or FIG. 5D'-2, which is another structure of the cellular phone (e.g., a smartphone).

Note that in the case of the structure illustrated in FIG. 5D'-1 or FIG. 5D'-2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the cellular phone is placed in user's breast pocket.

Figure 6A:
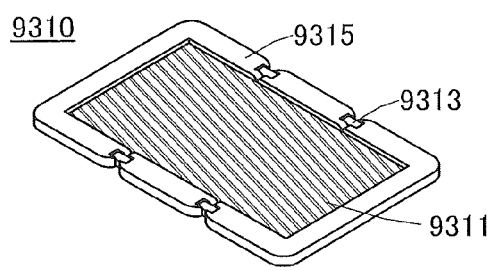
FIGS. 6A to 6C illustrate an electronic device.
Figure 6B:
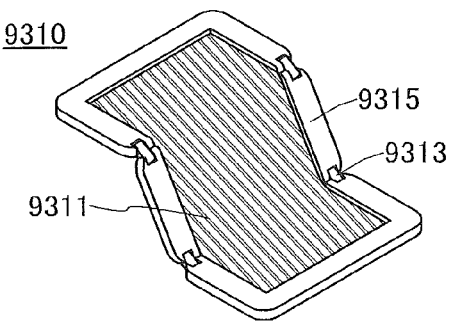
Figure 6C:
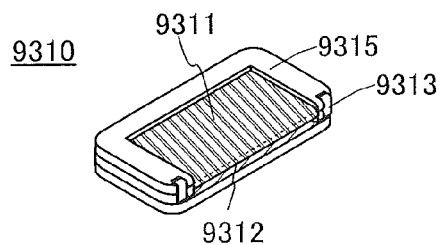

Another electronic device including a light-emitting device is a foldable portable information terminal illustrated in FIGS. 6A to 6C. FIG. 6A illustrates a portable information terminal 9310 which is opened. FIG. 6B illustrates the portable information terminal 9310 which is being opened or being folded. FIG. 6C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. The light-emitting device of one embodiment of the present invention can be used for the display portion 9311. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application can be smoothly performed.

Figure 7A:
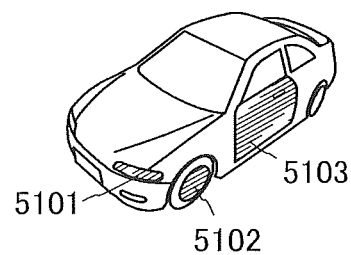
FIGS. 7A and 7B illustrate an automobile.
Figure 7B:
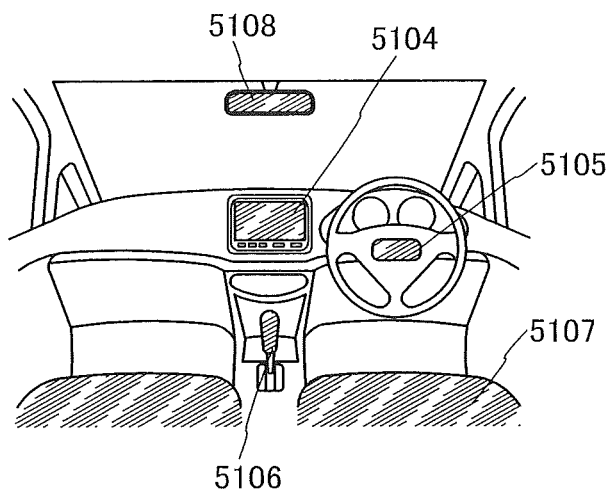

FIGS. 7A and 7B illustrate an automobile including a light-emitting device. The light-emitting device can be incorporated in the automobile, and specifically, can be included in lights 5101 (including lights of the rear part of the car), a wheel 5102 of a tire, a part or whole of a door 5103, or the like on the outer side of the automobile which is illustrated in FIG. 7A. The light-emitting device can also be included in a display portion 5104, a steering wheel 5105, a gear lever 5106, a sheet 5107, an inner rearview mirror 5108, or the like on the inner side of the automobile which is illustrated in FIG. 7B, or in a part of a glass window.

As described above, the electronic devices and automobiles can be obtained using the light-emitting device which is one embodiment of the present invention. Note that the light-emitting device can be used for electronic devices and automobiles in a variety of fields without being limited to the electronic devices described in this embodiment.

Note that the structure described in this embodiment can be combined as appropriate with any of the structures described in other embodiments.

Embodiment 6

In this embodiment, a structure of a lighting device fabricated using the light-emitting element which is one embodiment of the present invention is described with reference to FIGS. 8A to 8D.

Figure 8A:
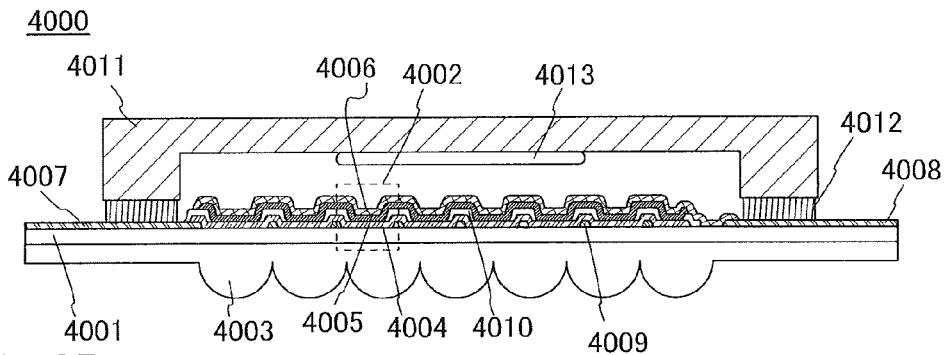
FIGS. 8A to 8D illustrate lighting devices.
Figure 8B:
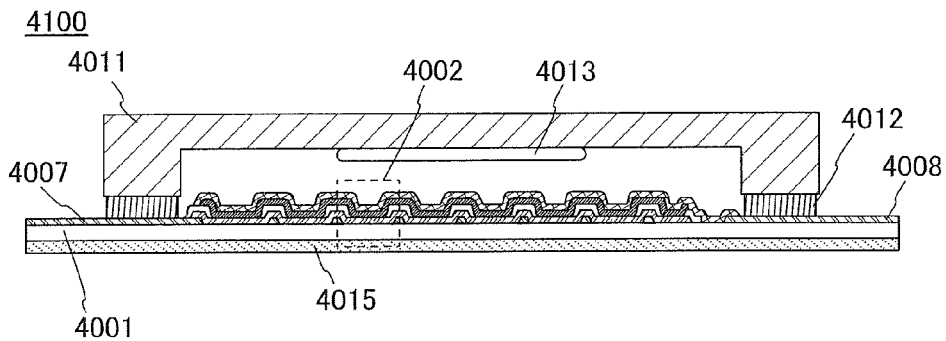
Figure 8C:
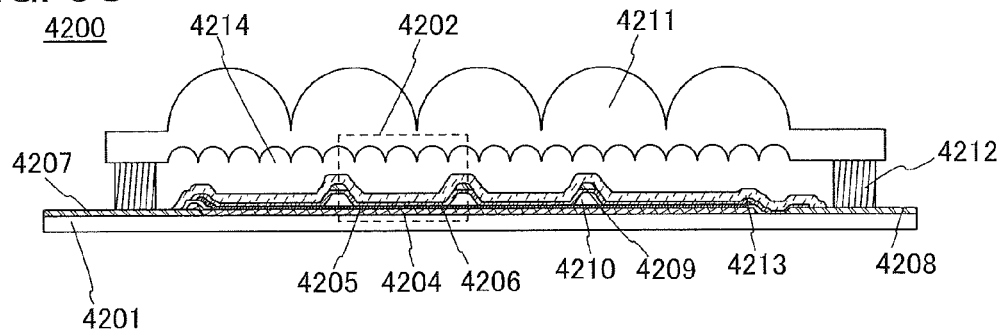
Figure 8D:
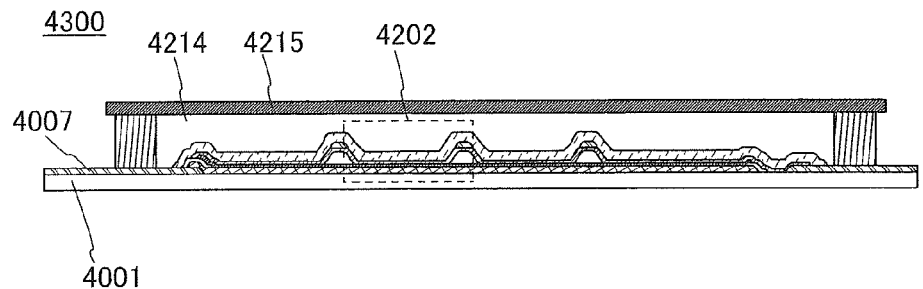

FIGS. 8A to 8D are examples of cross-sectional views of lighting devices. FIGS. 8A and 8B illustrate bottom-emission lighting devices in which light is extracted from the substrate side, and FIGS. 8C and 8D illustrate top-emission lighting devices in which light is extracted from the sealing substrate side.

A lighting device 4000 illustrated in FIG. 8A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other by a sealant 4012. A desiccant 4013 is preferably provided between the sealing substrate 4011 and the light-emitting element 4002. The substrate 4003 has the unevenness illustrated in FIG. 8A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 8B.

A lighting device 4200 illustrated in FIG. 8C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other by a sealant 4212. A barrier film 4213 and a planarization film 4214 may be provided between the sealing substrate 4211 and the light-emitting element 4202. The sealing substrate 4211 has the unevenness illustrated in FIG. 8C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 8D.

The EL layers 4005 and 4205 in this embodiment can each include any of the organometallic complexes which are embodiments of the present invention. In that case, a lighting device with low power consumption can be provided.

Note that the structure described in this embodiment can be combined as appropriate with any of the structures described in other embodiments.

Embodiment 7

In this embodiment, examples of a lighting device to which the light-emitting device of one embodiment of the present invention is applied are described with reference to FIG. 9.

Figure 9:
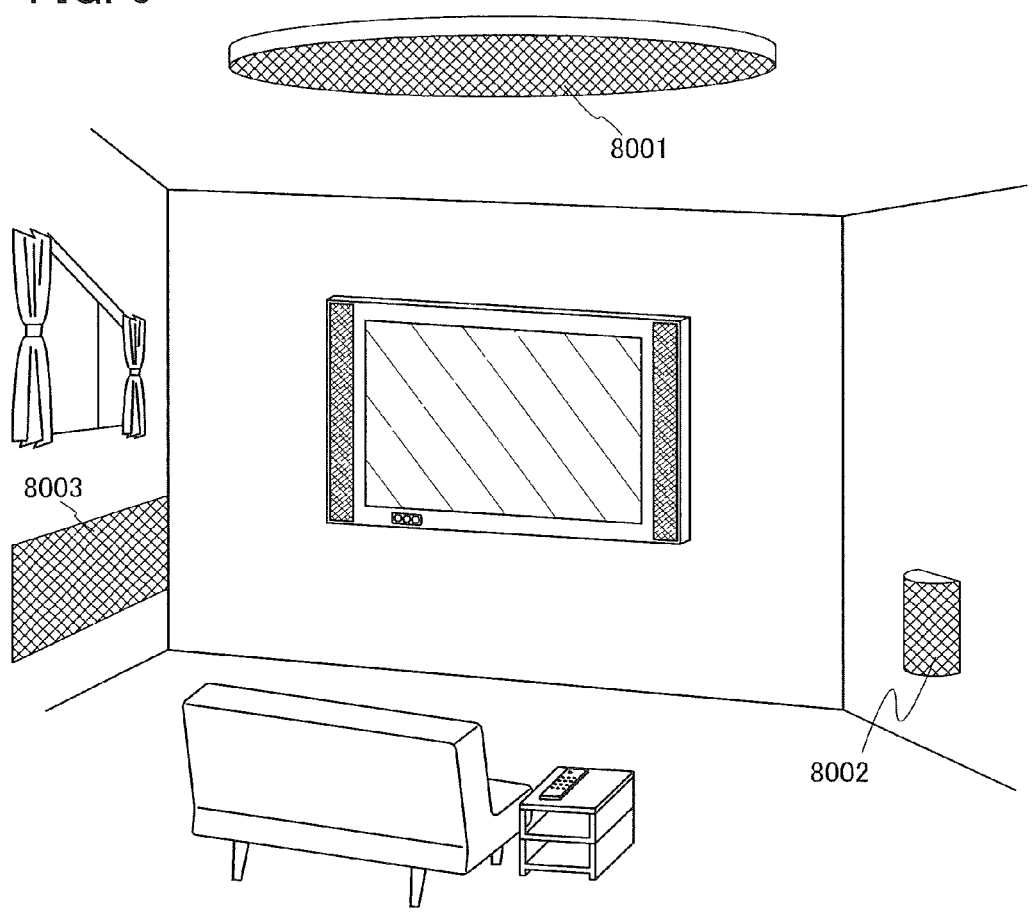
FIG. 9 illustrates lighting devices.

FIG. 9 illustrates an example in which the light-emitting device is used as an indoor lighting device 8001. Since the light-emitting device can have a large area, it can be used for a lighting device having a large area. In addition, with the use of a housing with a curved surface, a lighting device 8002 in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a lighting device 8003.

Besides the above examples, when the light-emitting device is used as part of furniture in a room, a lighting device that functions as the furniture can be obtained.

As described above, a variety of lighting devices that include the light-emitting device can be obtained. Note that these lighting devices are also embodiments of the present invention.

Note that the structure described in this embodiment can be combined as appropriate with any of the structures described in other embodiments.

Embodiment 8

In this embodiment, touch panels including the light-emitting element of one embodiment of the present invention or the light-emitting device of one embodiment of the present invention will be described with reference to FIGS. 10A and 10B, FIGS. 11A and 11B, FIGS. 12A and 12B, FIGS. 13A and 13B, and FIG. 14.

Figure 10A:
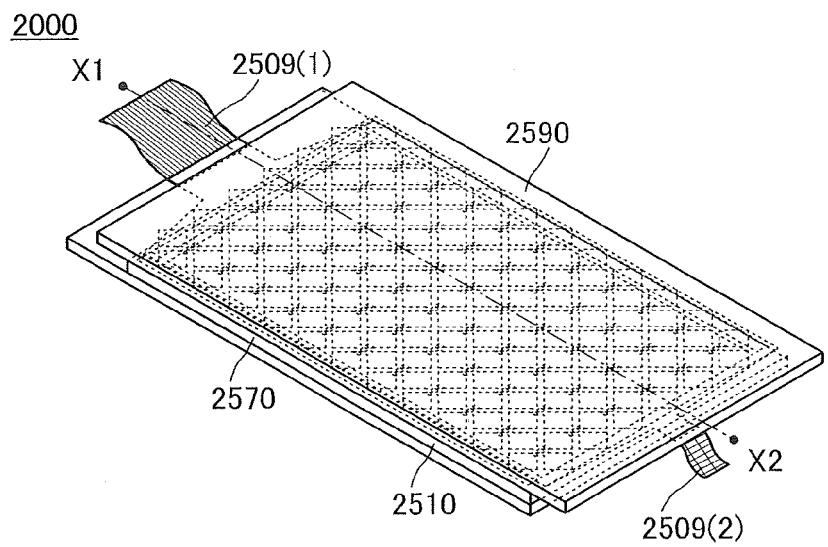
FIGS. 10A and 10B illustrate an example of a touch panel.
Figure 10B:
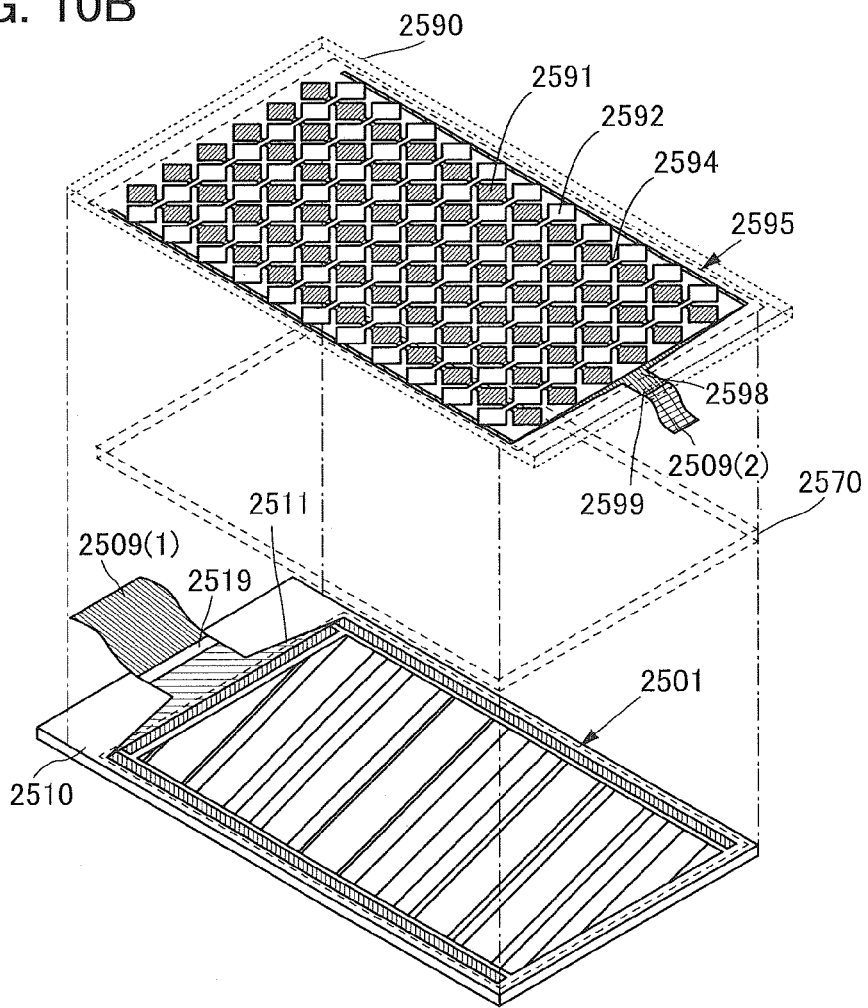

FIGS. 10A and 10B are perspective views of a touch panel 2000. Note that FIGS. 10A and 10B illustrate typical components of the touch panel 2000 for simplicity.

The touch panel 2000 includes a display panel 2501 and a touch sensor 2595 (see FIG. 10B). Furthermore, the touch panel 2000 includes substrates 2510, 2570, and 2590.

The display panel 2501 includes a plurality of pixels over the substrate 2510, and a plurality of wirings 2511 through which signals are supplied to the pixels. The plurality of wirings 2511 are led to a peripheral portion of the substrate 2510, and part of the plurality of wirings 2511 forms a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and part of the plurality of wirings 2598 forms a terminal 2599. The terminal 2599 is electrically connected to an FPC 2509(2). Note that in FIG. 10B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used, for example. Examples of the capacitive touch sensor are a surface capacitive touch sensor, a projected capacitive touch sensor, and the like.

Examples of the projected capacitive touch sensor are a self-capacitive touch sensor, a mutual capacitive touch sensor, and the like, which differ mainly in the driving method. The use of a mutual capacitive touch sensor is preferable because multiple points can be sensed simultaneously.

First, an example of using a projected capacitive touch sensor is described with reference to FIG. 10B. Note that in the case of a projected capacitive touch sensor, a variety of sensors that can sense the approach or contact of an object such as a finger can be used.

The projected capacitive touch sensor 2595 includes electrodes 2591 and 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594 in one direction, as illustrated in FIGS. 10A and 10B. In the same manner, the electrodes 2591 each have a shape of a plurality of quadrangles arranged with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle greater than 0° and less than 90°.

The intersecting area of the wiring 2594 and one of the electrodes 2592 is preferably as small as possible. Such a structure allows a reduction in the area of a region where the electrodes are not provided, reducing unevenness in transmittance. As a result, unevenness in the luminance of light passing through the touch sensor 2595 can be reduced.

Note that the shapes of the electrodes 2591 and 2592 are not limited to the above-described shapes and can be any of a variety of shapes. For example, the plurality of electrodes 2591 may be provided so that a space between the electrodes 2591 are reduced as much as possible, and the plurality of electrodes 2592 may be provided with an insulating layer sandwiched between the electrodes 2591 and 2592. In that case, it is preferable to provide, between two adjacent electrodes 2592, a dummy electrode which is electrically insulated from these electrodes because the area of a region having a different transmittance can be reduced.

Figure 11A:
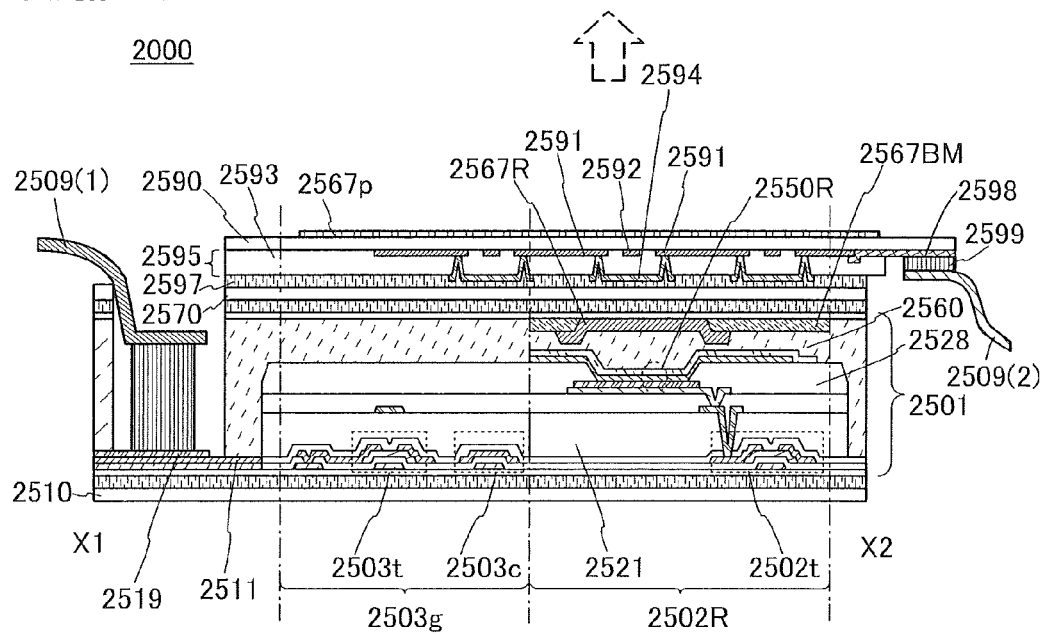
FIGS. 11A and 11B illustrate an example of a touch panel.
Figure 11B:
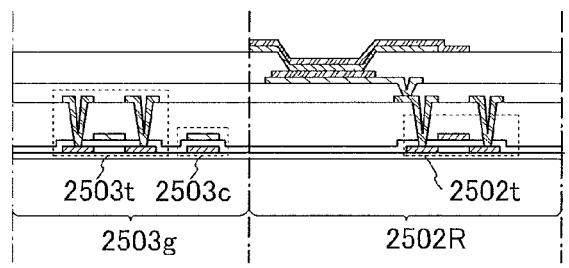

Next, the touch panel 2000 is described in detail with reference to FIGS. 11A and 11B. FIGS. 11A and 11B are cross-sectional views taken along the dashed-dotted line X1-X2 in FIG. 10A.

The touch panel 2000 includes the touch sensor 2595 and the display panel 2501.

The touch sensor 2595 includes the electrodes 2591 and 2592 that are provided in a staggered arrangement and in contact with the substrate 2590, an insulating layer 2593 covering the electrodes 2591 and 2592, and the wiring 2594 that electrically connects the adjacent electrodes 2591 to each other. Between the adjacent electrodes 2591, the electrode 2592 is provided.

The electrodes 2591 and 2592 can be formed using a light-transmitting conductive material. As a light-transmitting conductive material, a conductive oxide such as indium oxide, indium tin oxide, indium zinc oxide, zinc oxide, or zinc oxide to which gallium is added can be used. A graphene compound may be used as well. When a graphene compound is used, it can be formed, for example, by reducing a graphene oxide film. As a reducing method, a method with application of heat, a method with laser irradiation, or the like can be employed.

For example, the electrodes 2591 and 2592 can be formed by depositing a light-transmitting conductive material on the substrate 2590 by a sputtering method and then removing an unneeded portion by any of various patterning techniques such as photolithography.

Examples of a material for the insulating layer 2593 are a resin such as an acrylic resin or an epoxy resin, a resin having a siloxane bond, and an inorganic insulating material such as silicon oxide, silicon oxynitride, or aluminum oxide.

The adjacent electrodes 2591 are electrically connected to each other with the wiring 2594 formed in part of the insulating layer 2593. Note that a material for the wiring 2594 preferably has higher conductivity than materials for the electrodes 2591 and 2592 to reduce electrical resistance.

One wiring 2598 is electrically connected to any of the electrodes 2591 and 2592. Part of the wiring 2598 serves as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

An adhesive layer 2597 is provided in contact with the wiring 2594. That is, the touch sensor 2595 is attached to the display panel 2501 so that they overlap with each other with the adhesive layer 2597 provided therebetween. Note that the substrate 2570 as illustrated in FIG. 11A may be provided over the surface of the display panel 2501 that is in contact with the adhesive layer 2597; however, the substrate 2570 is not always needed.

The adhesive layer 2597 has a light-transmitting property. For example, a thermosetting resin or an ultraviolet curable resin can be used; specifically, a resin such as an acrylic-based resin, a urethane-based resin, an epoxy-based resin, or a siloxane-based resin can be used.

The display panel 2501 in FIG. 11A includes, between the substrate 2510 and the substrate 2570, a plurality of pixels arranged in a matrix and a driver circuit. Each pixel includes a light-emitting element and a pixel circuit driving the light-emitting element.

In FIG. 11A, a pixel 2502R is shown as an example of the pixel of the display panel 2501, and a scan line driver circuit 2503g is shown as an example of the driver circuit.

The pixel 2502R includes a light-emitting element 2550R and a transistor 2502t that can supply electric power to the light-emitting element 2550R.

The transistor 2502t is covered with an insulating layer 2521. The insulating layer 2521 covers unevenness caused by the transistor and the like that have been already formed to provide a flat surface. The insulating layer 2521 may serve also as a layer for preventing diffusion of impurities. That is preferable because a reduction in the reliability of the transistor or the like due to diffusion of impurities can be prevented.

The light-emitting element 2550R is electrically connected to the transistor 2502t through a wiring. It is one electrode of the light-emitting element 2550R that is directly connected to the wiring. An end portion of the one electrode of the light-emitting element 2550R is covered with an insulator 2528.

The light-emitting element 2550R includes an EL layer between a pair of electrodes. A coloring layer 2567R is provided to overlap with the light-emitting element 2550R, and part of light emitted from the light-emitting element 2550R is transmitted through the coloring layer 2567R and extracted in the direction indicated by an arrow in the drawing. A light-blocking layer 2567BM is provided at an end portion of the coloring layer, and a sealing layer 2560 is provided between the light-emitting element 2550R and the coloring layer 2567R.

Note that when the sealing layer 2560 is provided on the side from which light from the light-emitting element 2550R is extracted, the sealing layer 2560 preferably has a light-transmitting property. The sealing layer 2560 preferably has a higher refractive index than the air.

The scan line driver circuit 2503g includes a transistor 2503t and a capacitor 2503c. Note that the driver circuit and the pixel circuits can be formed in the same process over the same substrate. Thus, in a manner similar to that of the transistor 2502t in the pixel circuit, the transistor 2503t in the driver circuit (scan line driver circuit 2503g) is also covered with the insulating layer 2521.

The wirings 2511 through which a signal can be supplied to the transistor 2503t are provided. The terminal 2519 is provided in contact with the wiring 2511. The terminal 2519 is electrically connected to the FPC 2509(1), and the FPC 2509(1) has a function of supplying signals such as an image signal and a synchronization signal. Note that a printed wiring board (PWB) may be attached to the FPC 2509(1).

Although the case where the display panel 2501 illustrated in FIG. 11A includes a bottom-gate transistor is described, the structure of the transistor is not limited thereto, and any of transistors with various structures can be used. In each of the transistors 2502t and 2503t illustrated in FIG. 11A, a semiconductor layer containing an oxide semiconductor can be used for a channel region. Alternatively, a semiconductor layer containing amorphous silicon or a semiconductor layer containing polycrystalline silicon that is obtained by crystallization process such as laser annealing can be used for a channel region.

FIG. 11B illustrates the structure of the display panel 2501 that includes a top-gate transistor instead of the bottom-gate transistor illustrated in FIG. 11A. The kind of the semiconductor layer that can be used for the channel region does not depend on the structure of the transistor.

In the touch panel 2000 illustrated in FIG. 11A, an anti-reflection layer 2567p overlapping with at least the pixel is preferably provided on a surface of the touch panel on the side from which light from the pixel is extracted, as illustrated in FIG. 11A. As the anti-reflection layer 2567p, a circular polarizing plate or the like can be used.

For the substrates 2510, 2570, and 2590 in FIG. 11A, for example, a flexible material having a vapor permeability of $1\times10^{-5}$ g/(m²·day) or lower, preferably $1\times10^{-6}$ g/(m²·day) or lower, can be favorably used. Alternatively, it is preferable to use the materials that make these substrates have substantially the same coefficient of thermal expansion. For example, the coefficients of linear expansion of the materials are $1\times10^{-3}$/K or lower, preferably $5\times10^{-5}$/K or lower, and further preferably $1\times10^{-5}$/K or lower.

Next, a touch panel 2000' having a structure different from that of the touch panel 2000 illustrated in FIGS. 11A and 11B is described with reference to FIGS. 12A and 12B. It can be used as a touch panel as well as the touch panel 2000.

Figure 12A:
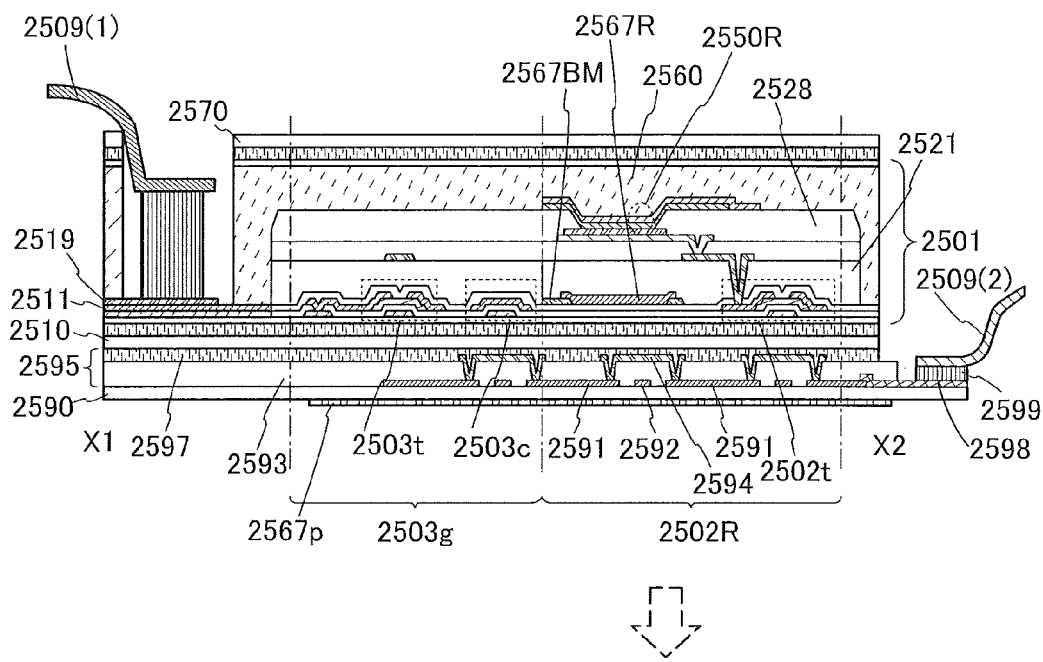
FIGS. 12A and 12B illustrate an example of a touch panel.
Figure 12B:
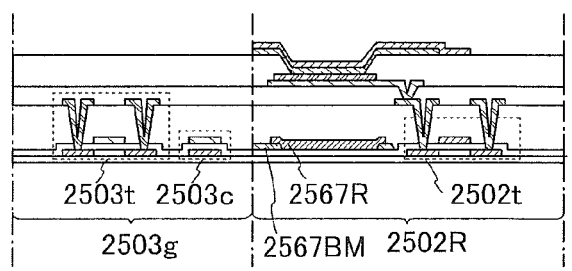

FIGS. 12A and 12B are cross-sectional views of the touch panel 2000'. In the touch panel 2000' illustrated in FIGS. 12A and 12B, the position of the touch sensor 2595 relative to the display panel 2501 is different from that in the touch panel 2000 illustrated in FIGS. 11A and 11B. Only different structures are described below, and the above description of the touch panel 2000 can be referred to for the other similar structures.

The coloring layer 2567R overlaps with the light-emitting element 2550R. Light from the light-emitting element 2550R illustrated in FIG. 12A is emitted to the side where the transistor 2502t is provided. That is, (part of) light emitted from the light-emitting element 2550R passes through the coloring layer 2567R and is extracted in the direction indicated by an arrow in FIG. 12A. Note that the light-blocking layer 2567BM is provided at an end portion of the coloring layer 2567R.

The touch sensor 2595 is provided on the transistor 2502t side (the far side from the light-emitting element 2550R) of the display panel 2501 (see FIG. 12A).

The adhesive layer 2597 is in contact with the substrate 2510 of the display panel 2501 and attaches the display panel 2501 and the touch sensor 2595 to each other in the structure illustrated in FIG. 12A. The substrate 2510 is not necessarily provided between the display panel 2501 and the touch sensor 2595 that are attached to each other by the adhesive layer 2597.

As in the touch panel 2000, transistors with a variety of structures can be used for the display panel 2501 in the touch panel 2000'. Although a bottom-gate transistor is used in FIG. 12A, a top-gate transistor may be used as illustrated in FIG. 12B.

An example of a driving method of the touch panel is described with reference to FIGS. 13A and 13B.

Figure 13A:
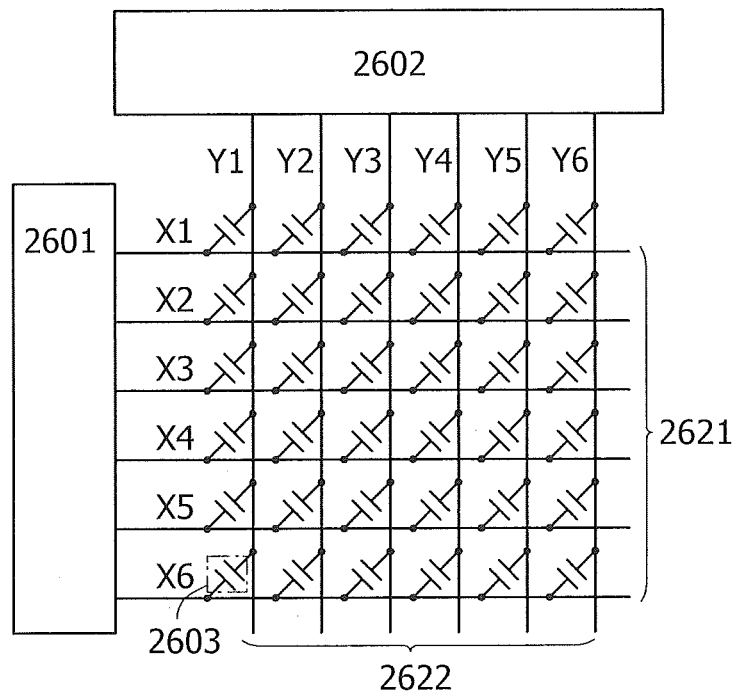
FIGS. 13A and 13B are a block diagram and a timing chart of a touch sensor.

FIG. 13A is a block diagram illustrating the structure of a mutual capacitive touch sensor. FIG. 13A illustrates a pulse voltage output circuit 2601 and a current sensing circuit 2602. Note that in the example of FIG. 13A, six wirings X1-X6 represent electrodes 2621 to which a pulse voltage is supplied, and six wirings Y1-Y6 represent electrodes 2622 that sense a change in current. FIG. 13A also illustrates a capacitor 2603 which is formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for sensing changes in current flowing through the wirings Y1 to Y6 that are caused by the change in mutual capacitance in the capacitor 2603. No change in current value is sensed in the wirings Y1 to Y6 when there is no approach or contact of a sensing target, whereas a decrease in current value is sensed when mutual capacitance is decreased owing to the approach or contact of a sensing target. Note that an integrator circuit or the like is used for sensing of current.

Figure 13B:
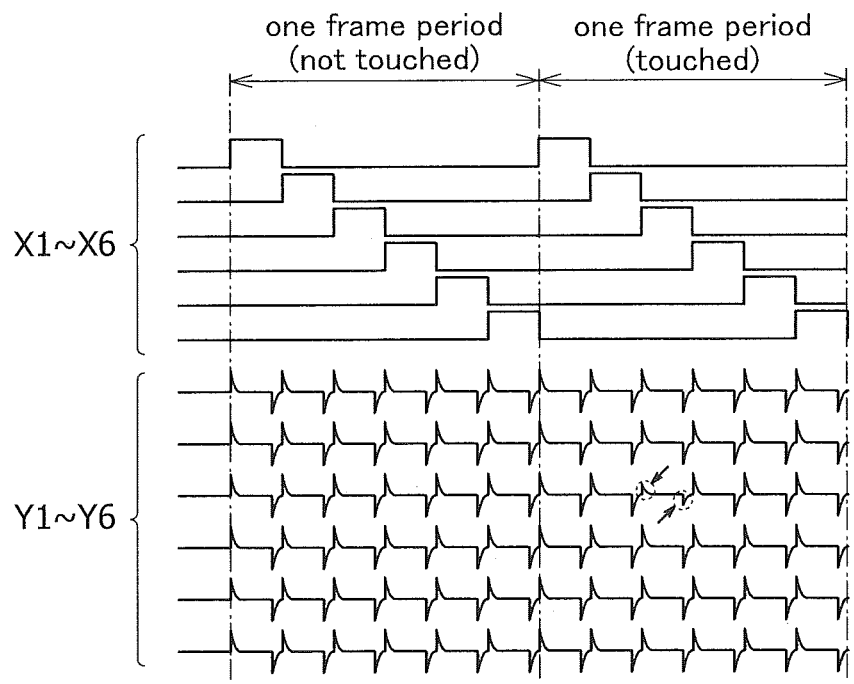

FIG. 13B is a timing chart showing input and output waveforms in the mutual capacitive touch sensor illustrated in FIG. 13A. In FIG. 13B, sensing of a sensing target is performed in all the rows and columns in one frame period. FIG. 13B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change uniformly in accordance with changes in the voltages of the wirings X1 to X6. The current value is decreased at the point of approach or contact of a sensing target and accordingly the waveform of the voltage value changes. By sensing a change in mutual capacitance in this manner, the approach or contact of a sensing target can be sensed.

Figure 14:
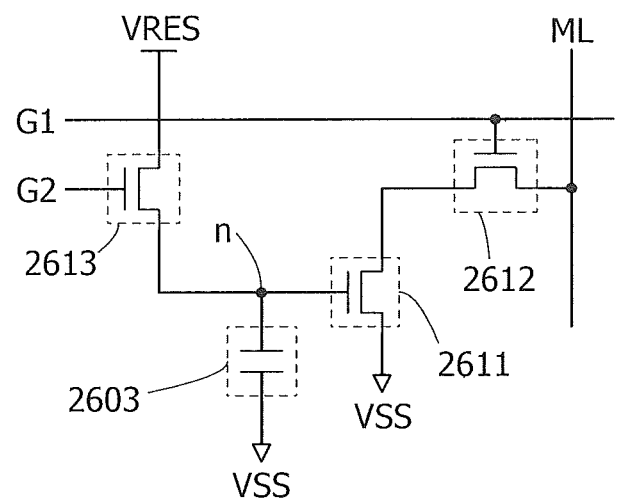
FIG. 14 is a circuit diagram of a touch sensor.

Although FIG. 13A illustrates a passive touch sensor in which only the capacitor 2603 is provided at the intersection of wirings as a touch sensor, an active touch sensor including a transistor and a capacitor may be used. FIG. 14 is a sensor circuit included in an active touch sensor.

The sensor circuit illustrated in FIG. 14 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit illustrated in FIG. 14 is described. First, a potential for turning on the transistor 2613 is supplied as the signal G2, and a potential with respect to the voltage VRES is thus applied to a node n connected to the gate of the transistor 2611. Then, a potential for turning off the transistor 2613 is applied as the signal G2, whereby the potential of the node n is maintained. Then, mutual capacitance of the capacitor 2603 changes owing to the approach or contact of a sensing target such as a finger; accordingly, the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613, so that the potential of the node n can be held for a long time and the frequency of operation of resupplying VRES to the node n (refresh operation) can be reduced.

Note that the structure described in this embodiment can be used in appropriate combination with any of the structures described in other embodiments.

Embodiment 9

In this embodiment, as a display device including any of the light-emitting elements which are embodiments of the present invention, a display device which includes a reflective liquid crystal element and a light-emitting element and is capable of performing display both in a transmissive mode and a reflective mode is described with reference to FIGS. 15A, 15B1, and 15B2, FIG. 16, and FIG. 17. Such a display device can also be referred to as an emissive OLED and reflective LC hybrid display (ER-hybrid display).

The display device described in this embodiment can be driven with extremely low power consumption for display using the reflective mode in a bright place such as outdoors. Meanwhile, in a dark place such as indoors or at night, image can be displayed at an optimal luminance with the use of the transmissive mode. Thus, by combination of these modes, the display device can display an image with lower power consumption and a higher contrast compared to a conventional display panel.

As an example of the display device of this embodiment, description is made on a display device in which a liquid crystal element provided with a reflective electrode and a light-emitting element are stacked and an opening of the reflective electrode is provided in a position overlapping with the light-emitting element. Visible light is reflected by the reflective electrode in the reflective mode and light emitted from the light-emitting element is emitted through the opening of the reflective electrode in the transmissive mode. Note that transistors used for driving these elements (the liquid crystal element and the light-emitting element) are preferably formed on the same plane. It is preferable that the liquid crystal element and the light-emitting element be stacked through an insulating layer.

Figure 15A:
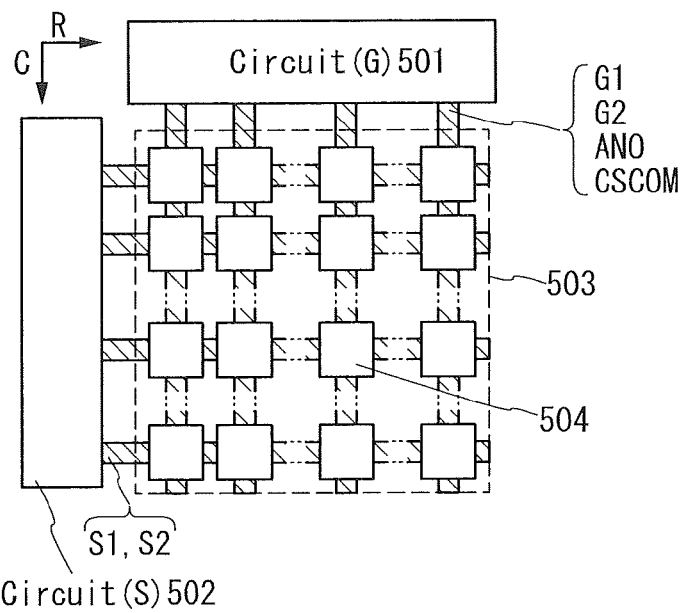
Figure 15A:
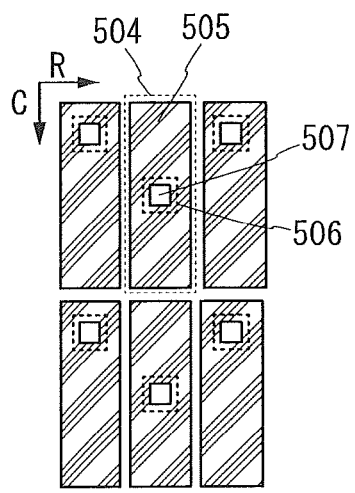
Figure 15A:
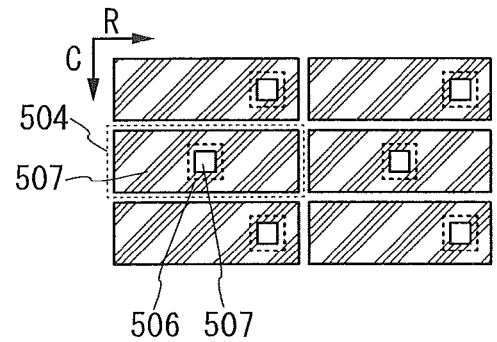

FIG. 15A is a block diagram illustrating a display device described in this embodiment. A display device 500 includes a circuit (G) 501, a circuit (S) 502, and a display portion 503. In the display portion 503, a plurality of pixels 504 are arranged in an R direction and a C direction in a matrix. A plurality of wirings G1, wirings G2, wirings ANO, and wirings CSCOM are electrically connected to the circuit (G) 501. These wirings are also electrically connected to the plurality of pixels 504 arranged in the R direction. A plurality of wirings S1 and wirings S2 are electrically connected to the circuit (S) 502, and these wirings are also electrically connected to the plurality of pixels 504 arranged in the C direction.

Each of the plurality of pixels 504 includes a liquid crystal element and a light-emitting element. The liquid crystal element and the light-emitting element include portions overlapping with each other.

FIG. 15B1 shows the shape of a conductive film 505 serving as a reflective electrode of the liquid crystal element included in the pixel 504. Note that an opening 507 is provided in a position 506 which is part of the conductive film 505 and which overlaps with the light-emitting element. That is, light emitted from the light-emitting element is emitted through the opening 507.

The pixels 504 in FIG. 15B1 are arranged such that adjacent pixels 504 in the R direction exhibit different colors. Furthermore, the openings 507 are provided so as not to be arranged in a line in the R direction. Such arrangement has an effect of suppressing crosstalk between the light-emitting elements of adjacent pixels 504.

The opening 507 can have a polygonal shape, a quadrangular shape, an elliptical shape, a circular shape, a cross shape, a stripe shape, or a slit-like shape, for example.

FIG. 15B2 illustrates another example of the arrangement of the conductive films 505.

The ratio of the opening 507 to the total area of the conductive film 505 (excluding the opening 507) affects the display of the display device. That is, a problem is caused in that as the area of the opening 507 is larger, the display using the liquid crystal element becomes darker; in contrast, as the area of the opening 507 is smaller, the display using the light-emitting element becomes darker. Furthermore, in addition to the problem of the ratio of the opening, a small area of the opening 507 itself also causes a problem in that extraction efficiency of light emitted from the light-emitting element is decreased. The ratio of opening 507 to the total area of the conductive film 505 (other than the opening 507) is preferably 5% or more and 60% or less for maintaining display quality at the time of combination of the liquid crystal element and the light-emitting element.

Figure 16:
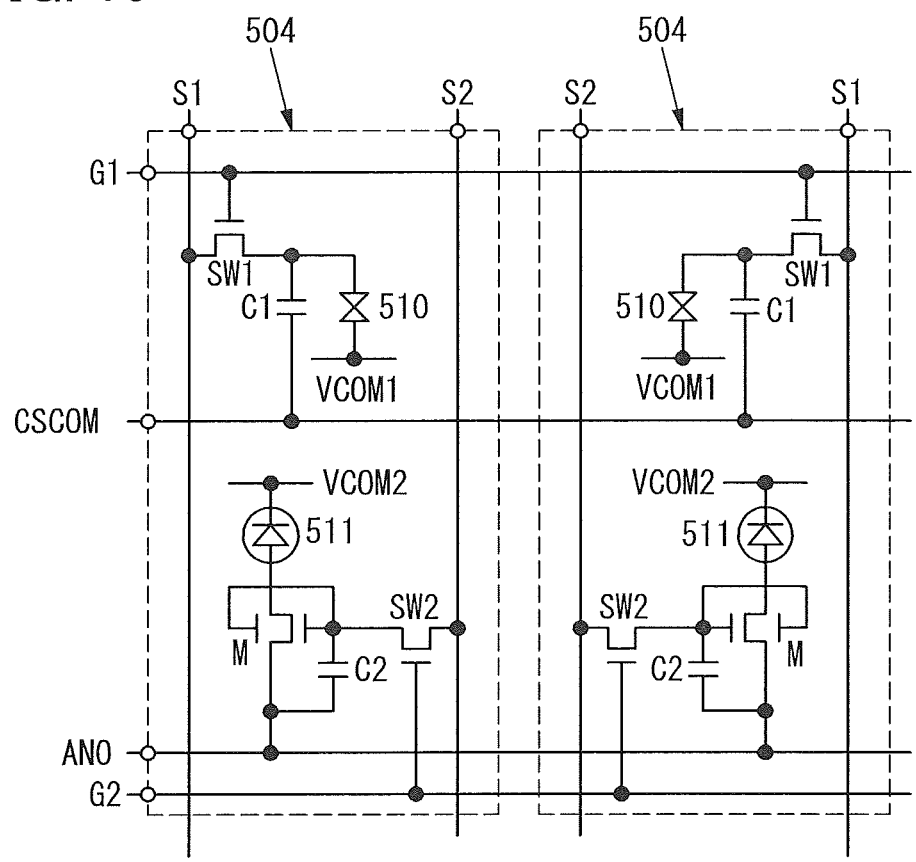
FIG. 16 illustrates a circuit configuration of a display device.

Next, an example of a circuit configuration of the pixel 504 is described with reference to FIG. 16. FIG. 16 shows two adjacent pixels 504.

The pixel 504 includes a transistor SW1, a capacitor C1, a liquid crystal element 510, a transistor SW2, a transistor M, a capacitor C2, a light-emitting element 511, and the like. Note that these components are electrically connected to any of the wiring G1, the wiring G2, the wiring ANO, the wiring CSCOM, the wiring S1, and the wiring S2 in the pixel 504.

The liquid crystal element 510 and the light-emitting element 511 are electrically connected to a wiring VCOM1 and a wiring VCOM2, respectively.

A gate of the transistor SW1 is connected to the wiring G1. One of a source and a drain of the transistor SW1 is connected to the wiring S1, and the other of the source and the drain is connected to one electrode of the capacitor C1 and one electrode of the liquid crystal element 510. The other electrode of the capacitor C1 is connected to the wiring CSCOM. The other electrode of the liquid crystal element 510 is connected to the wiring VCOM1.

A gate of the transistor SW2 is connected to the wiring G2. One of a source and a drain of the transistor SW2 is connected to the wiring S2, and the other of the source and the drain is connected to one electrode of the capacitor C2 and a gate of the transistor M. The other electrode of the capacitor C2 is connected to one of a source and a drain of the transistor M and the wiring ANO. The other of the source and the drain of the transistor M is connected to one electrode of the light-emitting element 511. Furthermore, the other electrode of the light-emitting element 511 is connected to the wiring VCOM2.

Note that the transistor M includes two gates between which a semiconductor is provided and which are electrically connected to each other. With such a structure, the amount of current flowing through the transistor M can be increased.

The on/off state of the transistor SW1 is controlled by a signal from the wiring G1. A predetermined potential is supplied from the wiring VCOM1. Furthermore, orientation of liquid crystals of the liquid crystal element 510 can be controlled by a signal from the wiring S1. A predetermined potential is supplied from the wiring CSCOM.

The on/off state of the transistor SW2 is controlled by a signal from the wiring G2. By the difference between the potentials applied from the wiring VCOM2 and the wiring ANO, the light-emitting element 511 can emit light. Furthermore, the on/off state of the transistor M is controlled by a signal from the wiring S2.

Accordingly, in the structure of this embodiment, in the case of the reflective mode, the liquid crystal element 510 is controlled by the signals supplied from the wiring G1 and the wiring S1 and optical modulation is utilized, whereby display can be performed. In the case of the transmissive mode, the light-emitting element 511 can emit light when the signals are supplied from the wiring G2 and the wiring S2. In the case where both modes are performed at the same time, desired driving can be performed on the basis of the signals from the wiring G1, the wiring G2, the wiring S1, and the wiring S2.

Figure 17:
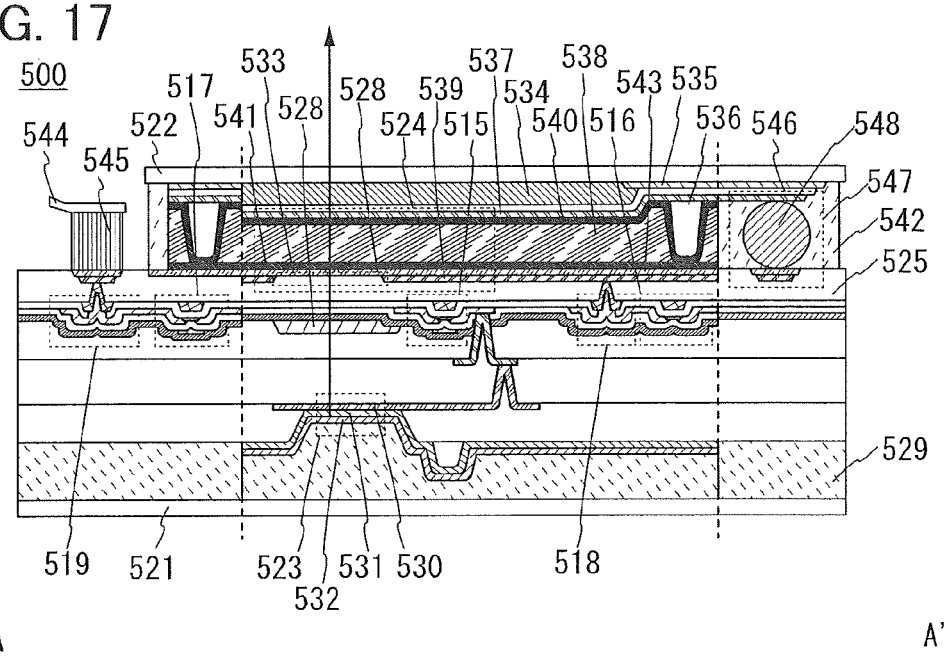
FIG. 17 illustrates a cross-sectional structure of a display device.

Next, specific description will be given with reference to FIG. 17, a schematic cross-sectional view of the display device 500 described in this embodiment.

The display device 500 includes a light-emitting element 523 and a liquid crystal element 524 between substrates 521 and 522. Note that the light-emitting element 523 and the liquid crystal element 524 are formed with an insulating layer 525 positioned therebetween. That is, the light-emitting element 523 is positioned between the substrate 521 and the insulating layer 525, and the liquid crystal element 524 is positioned between the substrate 522 and the insulating layer 525.

A transistor 515, a transistor 516, a transistor 517, a coloring layer 528, and the like are provided between the insulating layer 525 and the light-emitting element 523.

A bonding layer 529 is provided between the substrate 521 and the light-emitting element 523. The light-emitting element 523 includes a conductive layer 530 serving as one electrode, an EL layer 531, and a conductive layer 532 serving as the other electrode which are stacked in this order over the insulating layer 525. In the light-emitting element 523 that is a bottom emission light-emitting element, the conductive layer 532 and the conductive layer 530 contain a material that reflects visible light and a material that transmits visible light, respectively. Light emitted from the light-emitting element 523 is transmitted through the coloring layer 528 and the insulating layer 525 and then transmitted through the liquid crystal element 524 via an opening 533, thereby being emitted to the outside of the substrate 522.

In addition to the liquid crystal element 524, a coloring layer 534, a light-blocking layer 535, an insulating layer 546, a structure 536, and the like are provided between the insulating layer 525 and the substrate 522. The liquid crystal element 524 includes a conductive layer 537 serving as one electrode, a liquid crystal 538, a conductive layer 539 serving as the other electrode, alignment films 540 and 541, and the like. Note that the liquid crystal element 524 is a reflective liquid crystal element and the conductive layer 539 serves as a reflective electrode; thus, the conductive layer 539 is formed using a material with high reflectivity. Furthermore, the conductive layer 537 serves as a transparent electrode, and thus is formed using a material that transmits visible light. Alignment films 540 and 541 may be provided on the conductive layers 537 and 539 and in contact with the liquid crystal 538. The insulating layer 546 is provided so as to cover the coloring layer 534 and the light-blocking layer 535 and serves as an overcoat layer. Note that the alignment films 540 and 541 are not necessarily provided.

The opening 533 is provided in part of the conductive layer 539. A conductive layer 543 is provided in contact with the conductive layer 539. Since the conductive layer 543 has a light-transmitting property, a material transmitting visible light is used for the conductive layer 543.

The structure 536 serves as a spacer that prevents the substrate 522 from coming closer to the insulating layer 525 than required. The structure 536 is not necessarily provided.

One of a source and a drain of the transistor 515 is electrically connected to the conductive layer 530 in the light-emitting element 523. For example, the transistor 515 corresponds to the transistor M in FIG. 16.

One of a source and a drain of the transistor 516 is electrically connected to the conductive layer 539 and the conductive layer 543 in the liquid crystal element 524 through a terminal portion 518. That is, the terminal portion 518 electrically connects the conductive layers provided on both surfaces of the insulating layer 525. The transistor 516 corresponds to the transistor SW1 in FIG. 16.

A terminal portion 519 is provided in a region where the substrates 521 and 522 do not overlap with each other. Similarly to the terminal portion 518, the terminal portion 519 electrically connects the conductive layers provided on both surfaces of the insulating layer 525. The terminal portion 519 is electrically connected to a conductive layer obtained by processing the same conductive film as the conductive layer 543. Thus, the terminal portion 519 and the FPC 544 can be electrically connected to each other through a conductive layer 545.

A connection portion 547 is provided in part of a region where a bonding layer 542 is provided. In the connection portion 547, the conductive layer obtained by processing the same conductive film as the conductive layer 543 and part of the conductive layer 537 are electrically connected with a connector 548. Accordingly, a signal or a potential input from the FPC 544 can be supplied to the conductive layer 537 through the connector 548.

The structure 536 is provided between the conductive layer 537 and the conductive layer 543. The structure 536 maintains a cell gap of the liquid crystal element 524.

As the conductive layer 543, a metal oxide, a metal nitride, or an oxide such as an oxide semiconductor whose resistance is reduced is preferably used. In the case of using an oxide semiconductor, a material in which at least one of the concentrations of hydrogen, boron, phosphorus, nitrogen, and other impurities and the number of oxygen vacancies is made to be higher than those in a semiconductor layer of a transistor is used for the conductive layer 543.

Note that the structure described in this embodiment can be combined as appropriate with any of the structures described in other embodiments.

Example 1

Synthesis Example 1

This example shows a method for synthesizing an organometallic complex bis{9-ethyl-3-[6-(2-methylpropyl)-4-pyrimidinyl-κN3]-9H-pyrido[2,3-b]indol-2-yl-κC}(2,4-pentanedionato-κ$^2$O,O')iridium(III) (abbreviation: [Ir(iBuidrpypm)$_2$(acac)]), which is one embodiment of the present invention and represented by the structural formula (100) in Embodiment 1. A structure of [Ir(iBuidrpypm)$_2$(acac)] is shown below.

[Chemical formula 22]

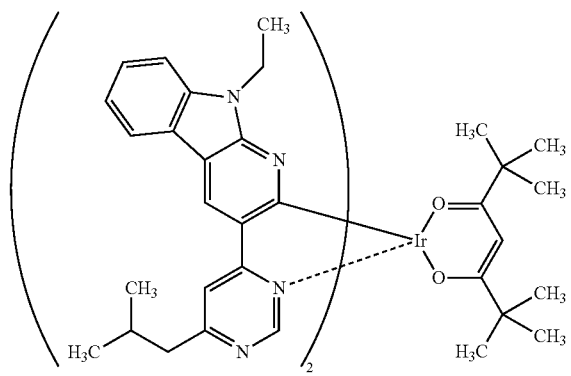

(100)

Step 1: Synthesis of 3-(4,4,5,5-tetramethyl-1,3,2-dioxaborolan-2-yl)-9H-pyrido[2,3-b]indole First, in a 200 mL three-neck flask were put 2.01 g of 3-chloro-9H-pyrido[2,3-b]indole, 3.02 g of bis(pinacolato)diboron, 1.52 g of potassium acetate, and 99 mL of dry acetonitrile, and the air in the flask was replaced with nitrogen.

The mixture in the flask was degassed by being stirred under reduced pressure, 1.4 mL of tricyclohexylphosphine (abbreviation: P(C$_6$H$_{11}$)$_3$) (a 0.6M toluene solution) and 0.37 g of tris(dibenzylideneacetone)dipalladium(0) (abbreviation: Pd$_2$(dba)$_3$) were added to the mixture, and stirring was performed at 85° C. for 12 hours. Furthermore, 0.7 mL of P(C$_6$H$_{11}$)$_3$ and 0.19 g of Pd$_2$(dba)$_3$ were added thereto, and the mixture was stirred at 85° C. for seven hours. Then, 0.7 mL of P(C$_6$H$_{11}$)$_3$ and 0.19 g of Pd$_2$(dba)$_3$ were added thereto, and the mixture was stirred at 85° C. for seven hours.

After that, water was added to this solution, and an organic layer was extracted with ethyl acetate. The extracted solution was washed with saturated saline, and magnesium sulfate was added for drying. The solution obtained by the drying was filtrated. The solvent of this solution was distilled off, and then the obtained residue was purified by silica gel column chromatography using hexane and ethyl acetate as a developing solvent in a volume ratio of 2:1 to give a target white powder in a yield of 41%. The synthesis scheme of Step 1 is shown in (a-1).

[Chemical formula 23]

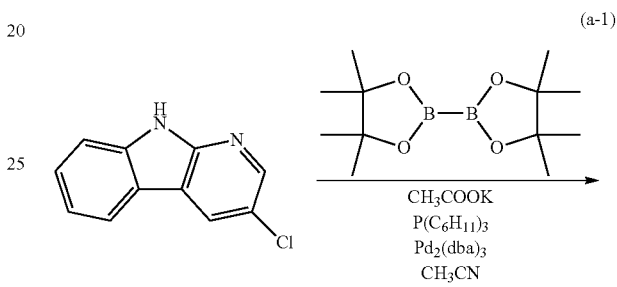

(a-1)

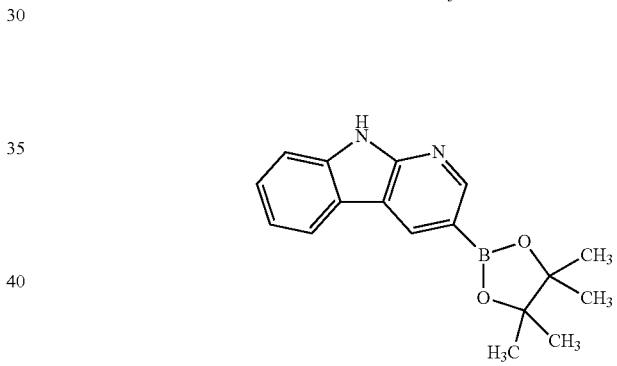

Step 2: Synthesis of 3-[6-(2-methylpropyl)-4-pyrimidinyl]-9H-pyrido[2,3-b]indole Next, in a 100-mL round-bottom flask equipped with a reflux pipe were put 1.82 g of 3-(4,4,5,5-tetramethyl-1,3,2-dioxaborolan-2-yl)-9H-pyrido[2,3-b]indole obtained in Step 1, 0.87 g of 4-chloro-6-(2-methylpropyl)pyrimidine, 7.7 mL of a 1 M aqueous solution of potassium acetate, 7.7 mL of a 1 M aqueous solution of sodium carbonate, and 16 mL of acetonitrile, and the air in the flask was replaced with argon. To this mixture, 0.35 g of tetrakis(triphenylphosphine)palladium(0) was added, and the reaction container was heated by irradiation with microwaves (2.45 GHz, 400 W) for an hour. Then, the precipitated solid was subjected to suction filtration and washed with water and ethanol. The obtained solid was purified by silica gel column chromatography using dichloromethane and ethyl acetate as a developing solvent in a volume ratio of 2:1 to give a target white powder in a yield of 91%. The synthesis scheme of Step 2 is shown in (a-2).

[Chemical formula 24]

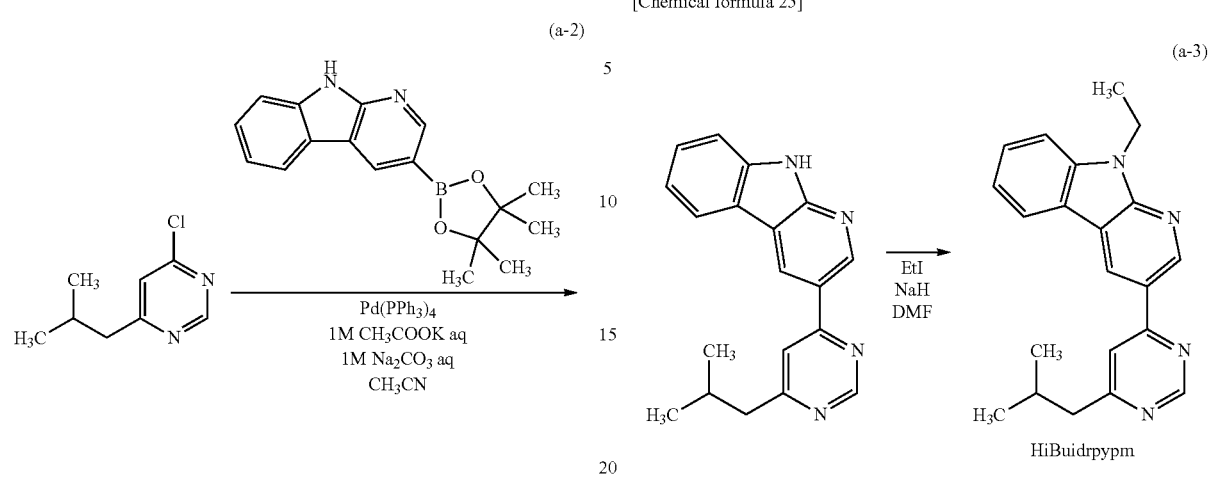

Step 3: Synthesis of 9-ethyl-3-[6-(2-methylpropyl)-4-pyrimidinyl]-9H-pyrido[2,3-b]indole Next, in a 100 mL three-neck flask were put 1.71 g of 3-[6-(2-methylpropyl)-4-pyrimidinyl]-9H-pyrido[2,3-b]indole obtained in Step 2 and 50 mL of dry DMF, and the air in the flask was replaced with nitrogen. Then, 0.68 g of sodium hydride (60% in mineral oil) was added to this mixture, and stirring was performed at room temperature for an hour. After that, 0.96 mL of iodoethane was added dropwise, and the mixture was stirred at room temperature for 20 and a half hours. The obtained reaction solution was poured into 150 mL of water, and an organic layer was extracted with dichloromethane. The extracted solution was washed with saturated saline, and magnesium sulfate was added for drying. The solution obtained by the drying was filtrated. The solvent of this solution was distilled off, and then the obtained residue was purified by silica gel column chromatography using hexane and ethyl acetate as a developing solvent in a volume ratio of 5:1 to give yellow oil of the target pyrimidine derivative HiBuidrpypm (abbreviation) in a yield of 86%. The synthesis scheme of Step 3 is shown in (a-3).

[Chemical formula 25]

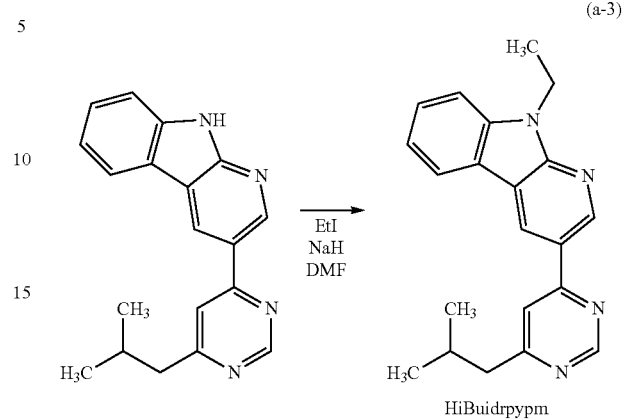

Step 4: Synthesis of di-µ-chloro-tetrakis{9-ethyl-3-[6-(2-methylpropyl)-4-pyrimidinyl-κN3]-9H-pyrido[2,3-b]indol-2-yl-κC}diiridium(III) (abbreviation: [Ir(iBuidrpypm)$_2$Cl]$_2$)

Next, in a recovery flask equipped with a reflux pipe were put 15 mL of 2-ethoxyethanol, 5 mL of water, 1.60 g of HiBuidrpypm (abbreviation) obtained in Step 3, and 0.69 g of iridium chloride hydrate (IrCl$_3$.nH$_2$O) (produced by Furuya Metal Co., Ltd.), and the air in the flask was replaced with argon. After that, microwave irradiation (2.45 GHz, 100 W) was performed for an hour to cause a reaction. The solvent was distilled off, and then the obtained residue was subjected to suction filtration and washed with methanol to give a yellow-brown powder of a dinuclear complex [Ir(iBuidrpypm)$_2$Cl]$_2$ (abbreviation) in a yield of 83%. Note that the microwave irradiation was performed using a microwave synthesis system (Discover, manufactured by CEM Corporation). The synthesis scheme of Step 4 is shown in (a-4).

[Chemical formula 26]

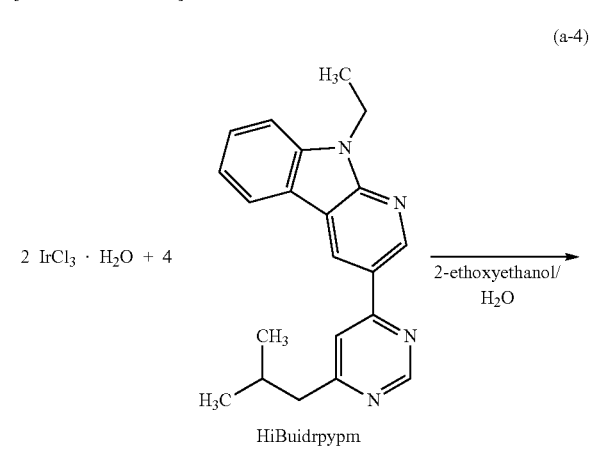

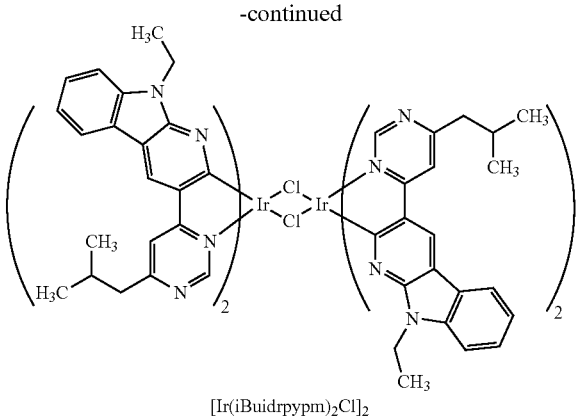

[Ir(iBuidrpypm)₂Cl]₂

Step 5: Synthesis of bis{9-ethyl-3-[6-(2-methylpropyl)-4-pyrimidinyl-κN3]-9H-pyrido[2,3-b]indol-2-yl-κC}(2,4-pentanedionato-κ²O,O')iridium(III) (abbreviation: [Ir(iBuidrpypm)₂(acac)])

In a recovery flask equipped with a reflux pipe were put 20 mL of 2-ethoxyethanol, 1.28 g of the dinuclear complex [Ir(iBuidrpypm)₂Cl]₂ (abbreviation) obtained in Step 4, 0.22 g of acetylacetone (abbreviation: Hacac), and 0.77 g of sodium carbonate, and the air in the flask was replaced with argon. After that, the mixture was heated by irradiation with microwaves (2.45 GHz, 120 W) for 60 minutes. The obtained reaction solution was subjected to suction filtration and the filtrate was concentrated, so that a yellow solid was obtained. The obtained solid was used for reaction. In a recovery flask equipped with a reflux pipe were put 0.94 g of the yellow solid, 0.16 g of Hacac, 0.56 g of sodium carbonate, and 20 mL of 2-ethoxyethanol, and the air in the flask was replaced with argon. After that, the mixture was heated by irradiation with microwaves (2.45 GHz, 120 W) for two hours. Here, 0.16 g of Hacac was further added, and the mixture was heated by irradiation with microwaves (2.45 GHz, 120 W) for two hours. The obtained reaction solution was subjected to suction filtration and washed with dichloromethane. The filtrate was concentrated, the obtained residue was purified by silica gel column chromatography using dichloromethane and ethyl acetate as a developing solvent in a volume ratio of 10:1, and recrystallization was performed with a mixed solvent of dichloromethane and ethanol. Thus, [Ir(iBuidrpypm)₂(acac)] (abbreviation), which is the organometallic complex of the present invention, was obtained as a yellow powder in a yield of 19%. By a train sublimation method, 0.27 g of the obtained yellow powder solid was purified. In the sublimation purification, the solid was heated at 310° C. under a pressure of 2.6 Pa with an argon gas flow rate of 5 mL/min. After the sublimation purification, a target yellow solid was obtained in a yield of 78%. A synthetic scheme of Step 5 is shown in (a-5).

[Chemical formula 27]

(a-5)

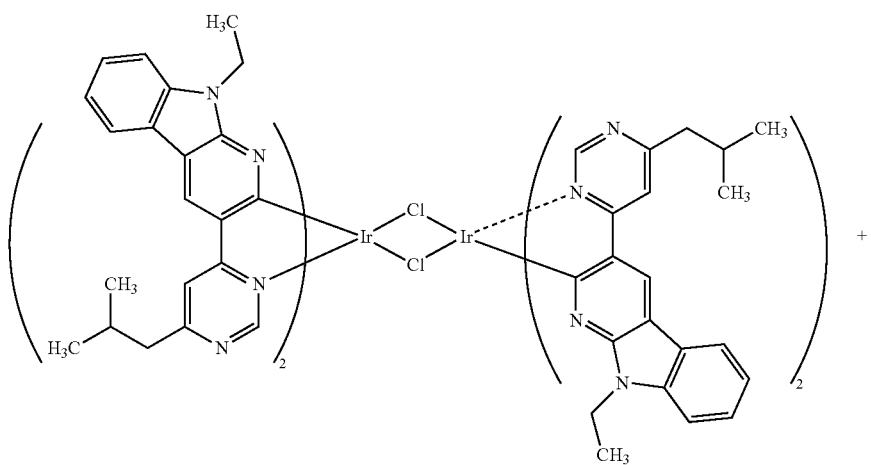

[Ir(iBuidrpypm)₂Cl]₂

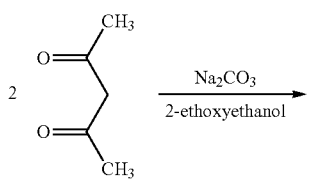

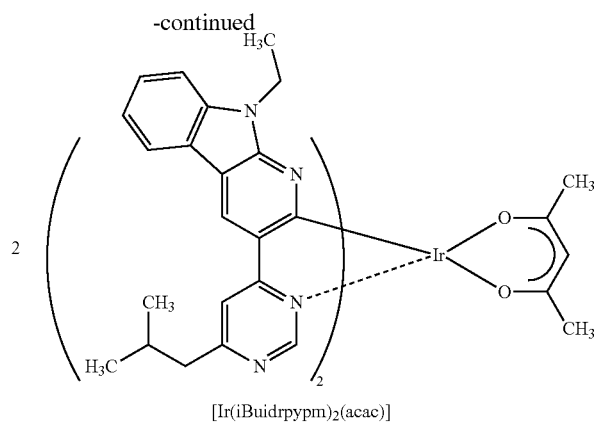

[Ir(iBuidrpypm)₂(acac)]

Figure 18:
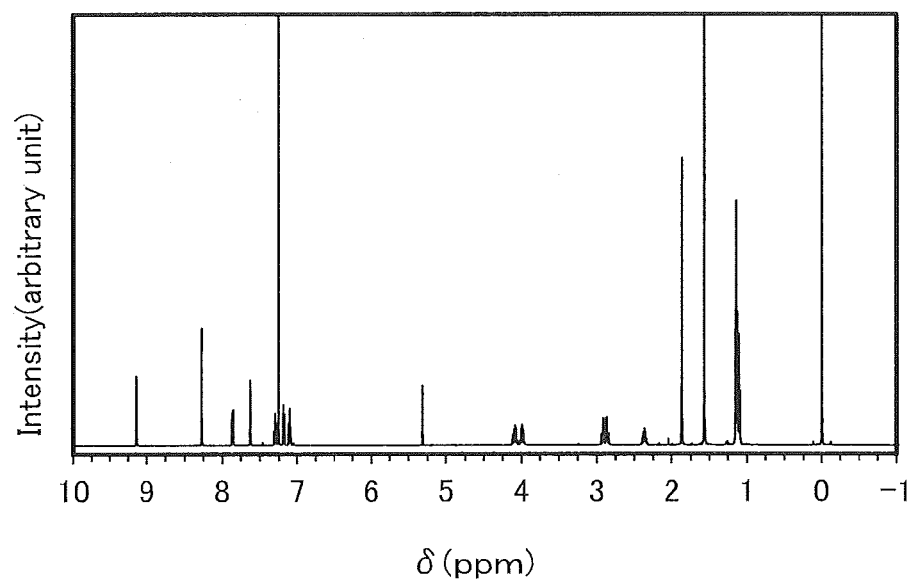
FIG. 18 is a $^1$H-NMR chart of an organometallic complex represented by the structural formula (100)

Analysis results by nuclear magnetic resonance spectrometry (¹H-NMR) of the compound obtained in Step 5 are shown below. The ¹H-NMR chart is shown in FIG. 18. The results demonstrate that the organometallic complex [Ir(iBuidrpypm)₂(acac)] represented by the above structural formula (100) was obtained in this synthesis example.

¹H-NMR. δ(CDCl₃): 1.11-1.16 (m, 18H), 1.87 (s, 6H), 2.35-2.40 (m, 2H), 2.85-2.95 (m, 4H), 3.97-4.03 (m, 2H), 4.06-4.12 (m, 2H), 5.32 (s, 1H), 7.11 (t, 2H), 7.19 (d, 2H), 7.31 (t, 2H), 7.63 (s, 2H), 7.87 (d, 2H), 8.28 (s, 2H), 9.15 (s, 2H).

Figure 19:
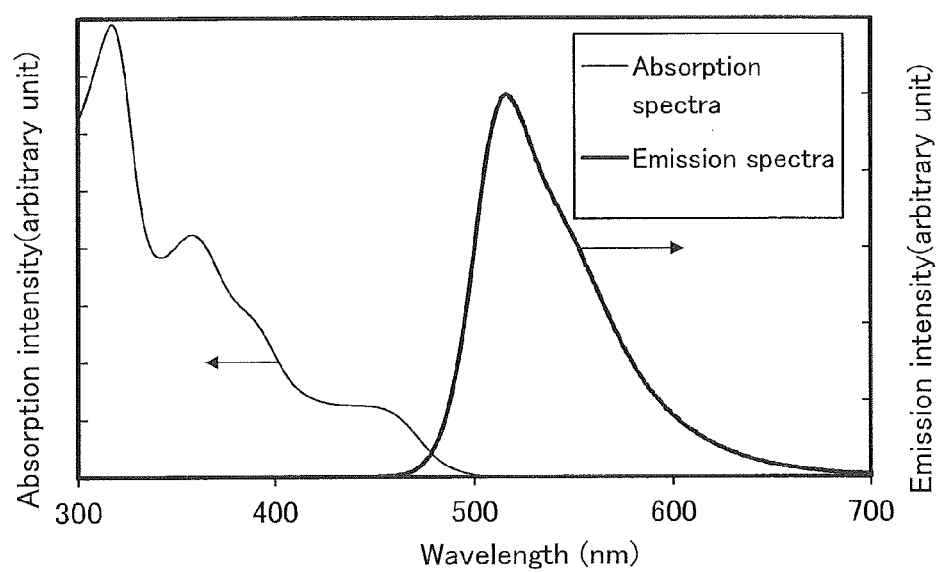
FIG. 19 shows the ultraviolet-visible absorption spectrum and the emission spectrum of the organometallic complex represented by the structural formula (100)

Next, an ultraviolet-visible absorption spectrum (hereinafter, simply referred to as an "absorption spectrum") and an emission spectrum of a dichloromethane solution of [Ir(iBuidrpypm)₂(acac)] were measured. The measurement of the absorption spectrum was conducted at room temperature, for which an ultraviolet-visible light spectrophotometer (V550 type manufactured by JASCO Corporation) was used and the dichloromethane solution (0.011 mmol/L) was put in a quartz cell. In addition, the measurement of the emission spectrum was performed at room temperature in such a manner that an absolute PL quantum yield measurement system (C11347-01 manufactured by Hamamatsu Photonics K. K.) was used and the deoxidized dichloromethane solution (0.011 mmol/L) was sealed in a quartz cell under a nitrogen atmosphere in a glove box (LABstar M13 (1250/780) manufactured by Bright Co., Ltd.). Analysis results of the obtained absorption and emission spectra are shown in FIG. 19, in which the horizontal axis represents wavelength and the vertical axes represent absorption intensity and emission intensity. In FIG. 19, two solid lines are shown; a thin line represents the absorption spectrum, and a thick line represents the emission spectrum. Note that the absorption spectrum in FIG. 19 is the results obtained in such a way that the absorption spectrum measured by putting only dichloromethane in a quartz cell was subtracted from the absorption spectrum measured by putting the dichloromethane solution (0.011 mmol/L) in a quartz cell.

As shown in FIG. 19, the organometallic complex [Ir(iBuidrpypm)₂(acac)] has an emission peak at 516 nm, and green light emission was observed from the dichloromethane solution.

Example 2

Synthesis Example 2

This example shows a method for synthesizing an organometallic complex tris{9-ethyl-3-[6-(2-methylpropyl)-4-pyrimidinyl-κN3]-9H-pyrido[2,3-b]indol-2-yl-κC}iridium (III) (abbreviation: [Ir(iBuidrpypm)₃]), which is one embodiment of the present invention and represented by the structural formula (112) in Embodiment 1. A structure of [Ir(iBuidrpypm)₃] is shown below.

[Chemical formula 28]

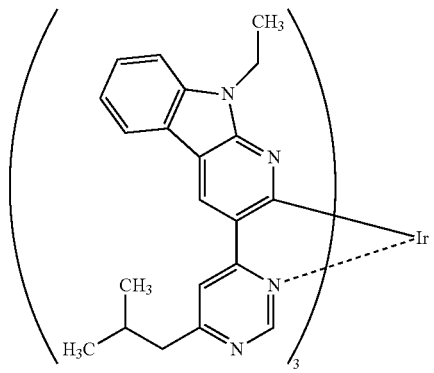

(112)

Synthesis of [Ir(iBuidrpypm)₃]

First, in a 200 mL three-neck flask equipped with a reflux pipe were put 0.43 g of a dinuclear complex [Ir(iBuidrpypm)₂Cl]) (abbreviation), 0.33 g of potassium carbonate, 0.39 g of HiBuidrpypm (abbreviation), and 4 g of phenol, and the air in the flask was replaced with nitrogen. Then, heating was performed at 195° C. for eight hours. After that, the obtained residue was irradiated with ultrasonic waves, subjected to suction filtration in methanol, and washed with water and methanol. The obtained solid was purified by silica gel column chromatography using dichloromethane and ethyl acetate as a developing solvent in a volume ratio of 1:2, and recrystallization was performed with a mixed solvent of toluene and hexane. Thus, a yellow powder of [Ir(iBuidrpypm)₃] (abbreviation) which is the organometallic complex of the present invention was obtained in a yield of 21%. The synthesis scheme is shown in (b-1).

[Chemical formula 29]

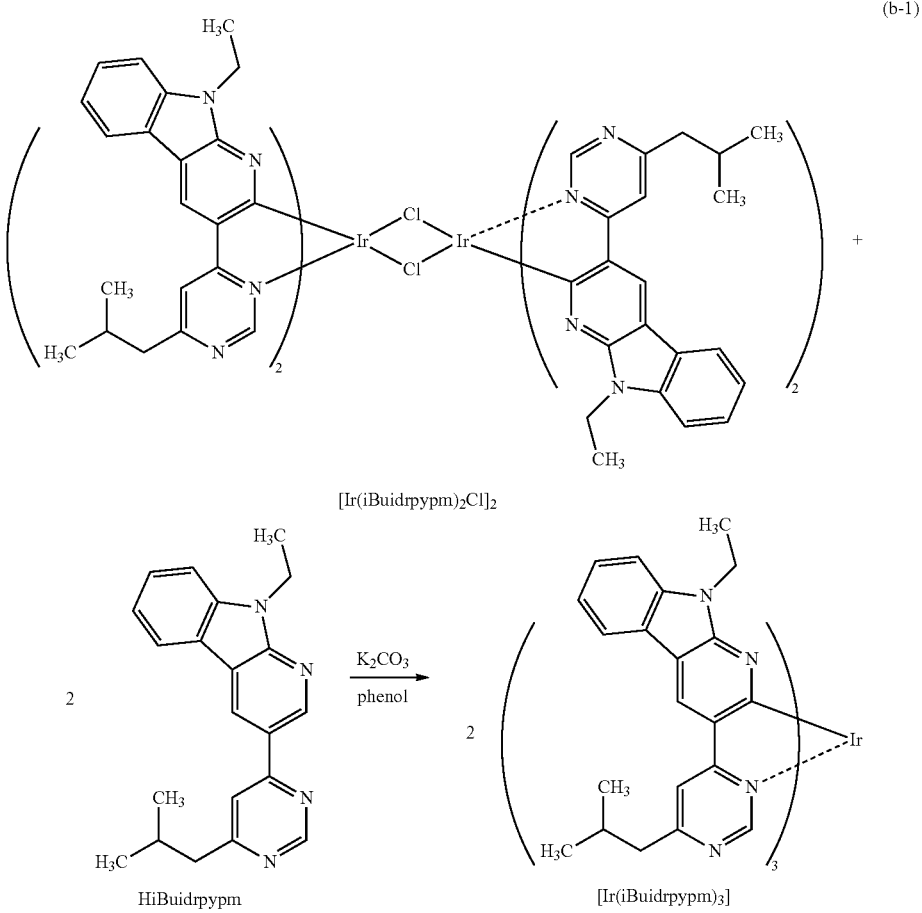

Figure 20:
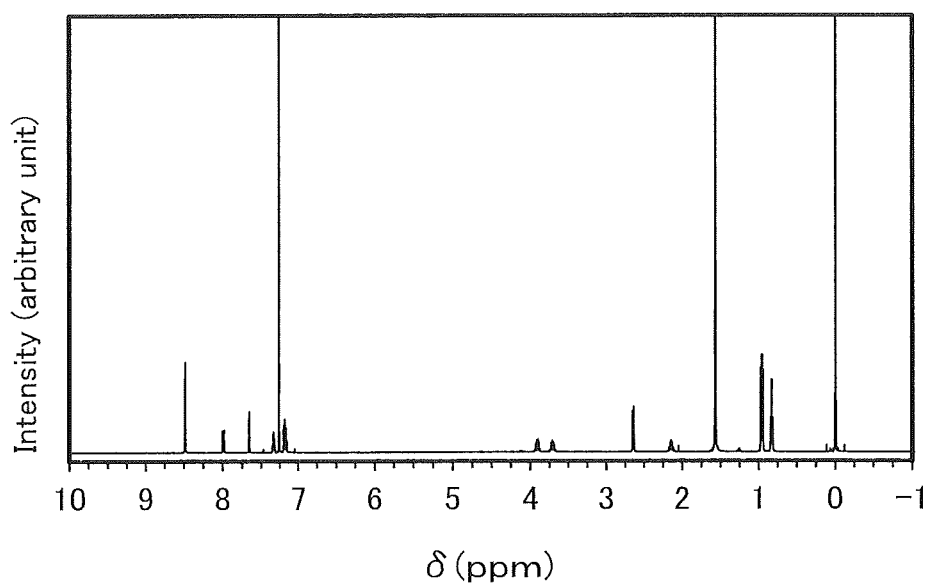
FIG. 20 is a $^1$H-NMR chart of an organometallic complex represented by the structural formula (112)

Analysis results by nuclear magnetic resonance spectrometry ($^1$H-NMR) of the obtained yellow powder are shown below. The $^1$H-NMR chart is shown in FIG. 20. The results demonstrate that the organometallic complex [Ir(iBuidrpypm)$_3$] represented by the above structural formula (112) was obtained in this synthesis example.

$^1$H NMR. δ(CDCl$_3$): 0.82-0.85 (m, 9H), 0.89-0.95 (m, 18H), 2.12-2.18 (m, 3H), 2.65 (d, 6H), 3.68-3.75 (m, 3H), 3.88-3.94 (m, 3H), 7.16-7.20 (m, 6H), 7.34 (t, 3H), 7.66 (s, 3H), 8.00 (d, 3H), 8.49 (s, 6H).

Next, an ultraviolet-visible absorption spectrum (hereinafter, simply referred to as an "absorption spectrum") and an emission spectrum of a dichloromethane solution of [Ir(iBuidrpypm)$_3$] were measured. The measurement of the absorption spectrum was conducted at room temperature, for which an ultraviolet-visible light spectrophotometer (V550 type manufactured by JASCO Corporation) was used and the dichloromethane solution (9.7 μmol/L) was put in a quartz cell. In addition, the measurement of the emission spectrum was performed at room temperature in such a manner that an absolute PL quantum yield measurement system (C11347-01 manufactured by Hamamatsu Photonics K. K.) was used and the deoxidized dichloromethane solution (9.7 μmol/L) was sealed in a quartz cell under a nitrogen atmosphere in a glove box (LABstar M13 (1250/780) manufactured by Bright Co., Ltd.).

Figure 21:
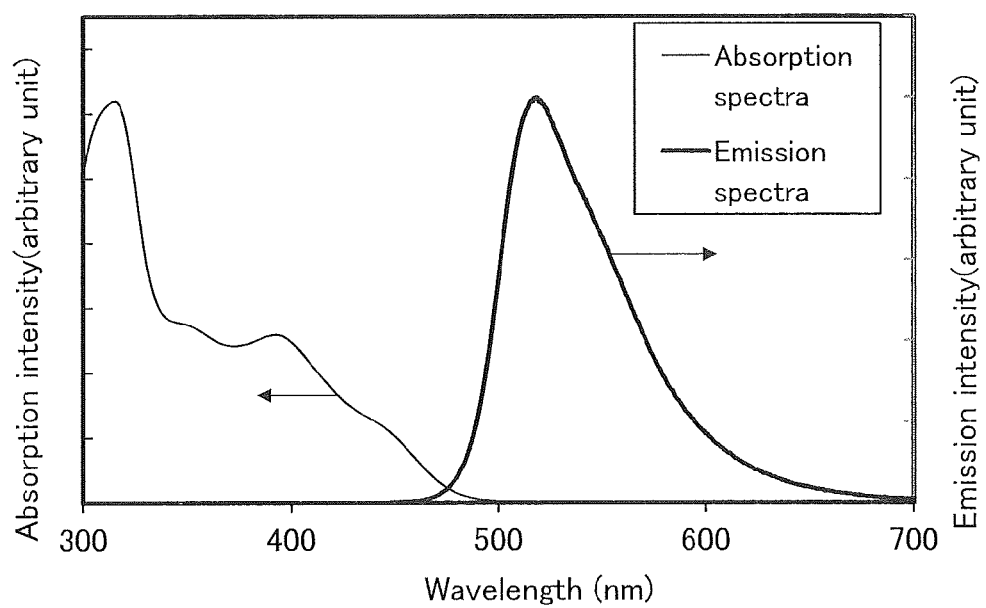
FIG. 21 shows the ultraviolet-visible absorption spectrum and the emission spectrum of the organometallic complex represented by the structural formula (112)

Analysis results of the obtained absorption and emission spectra are shown in FIG. 21, in which the horizontal axis represents wavelength and the vertical axes represent absorption intensity and emission intensity. In FIG. 21, two solid lines are shown; a thin line represents the absorption spectrum, and a thick line represents the emission spectrum. Note that the absorption spectrum in FIG. 21 is the results obtained in such a way that the absorption spectrum measured by putting only dichloromethane in a quartz cell was subtracted from the absorption spectrum measured by putting the dichloromethane solution (9.7 μmol/L) in a quartz cell.

As shown in FIG. 21, the organometallic complex [Ir(iBuidrpypm)$_3$] has an emission peak at 519 nm, and green light emission was observed from the dichloromethane solution.

Example 3

Figure 22:
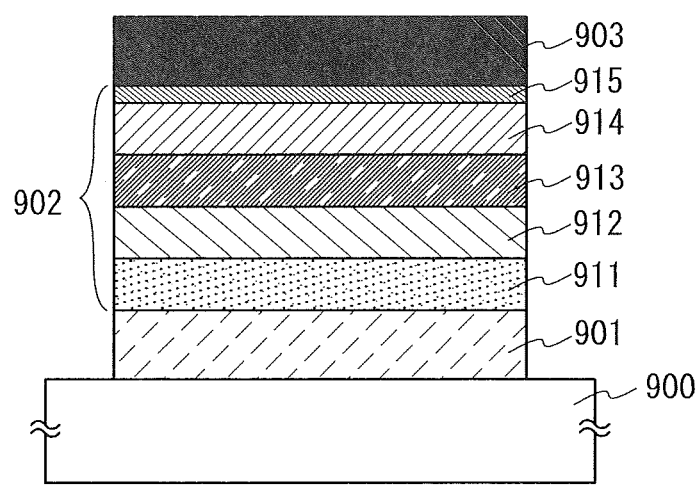
FIG. 22 illustrates a light-emitting element.

In this example, a light-emitting element 1 including [Ir(iBuidrpypm)$_2$(acac)] (structural formula (100)) which is the organometallic complex of one embodiment of the present invention, and a light-emitting element 2 including [Ir(iBuidrpypm)$_3$] (structural formula (112)) which is the organometallic complex of one embodiment of the present invention were fabricated. Note that the fabrication of the light-emitting elements 1 and 2 is described with reference to FIG. 22. Chemical formulae of materials used in this example are shown below.

[Chemical formulae 30]

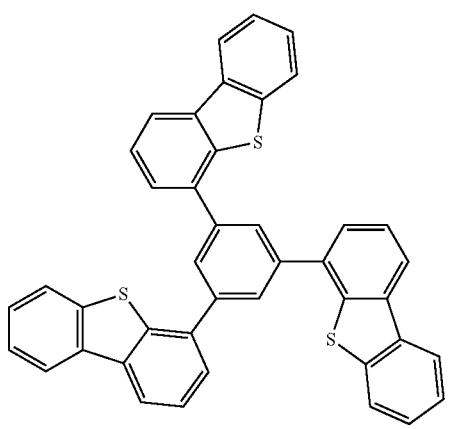

DBT3P-II

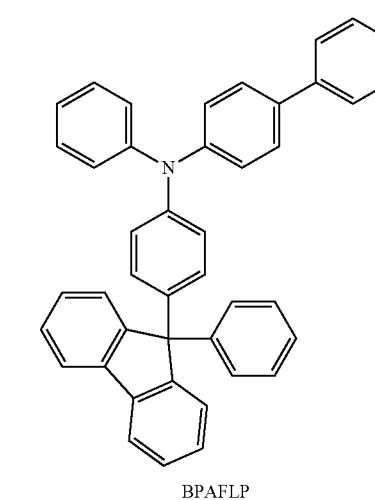

BPAFLP

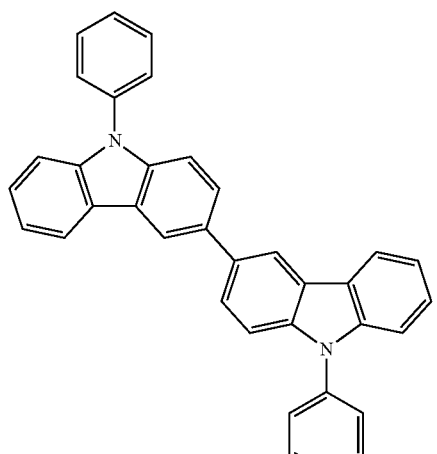

PCCP

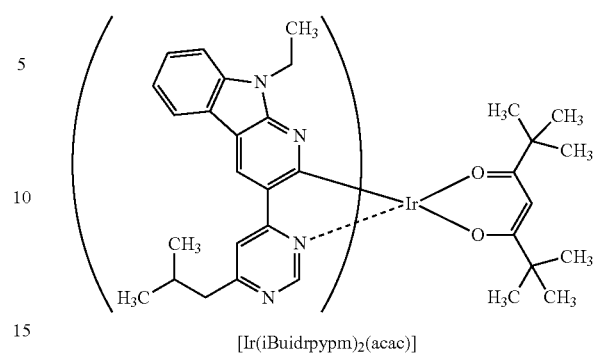

[Ir(iBuidrpypm)$_2$(acac)]        (100)

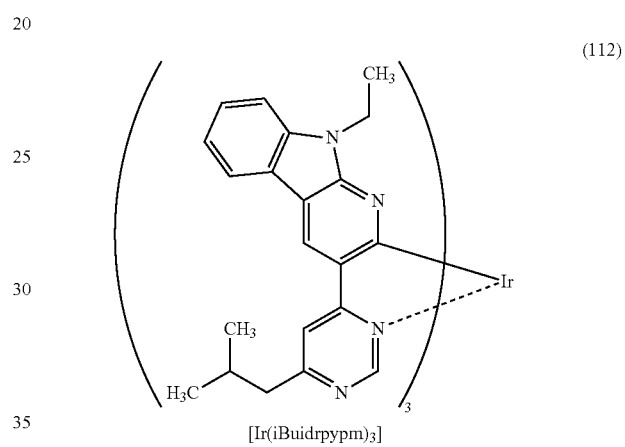

[Ir(iBuidrpypm)$_3$]        (112)

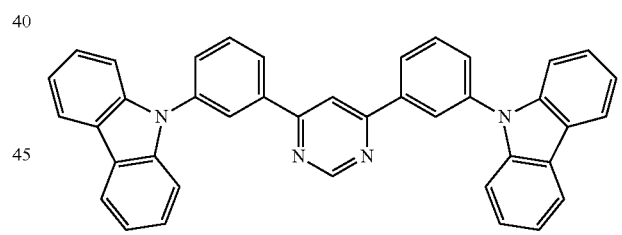

4,6mCzP2Pm

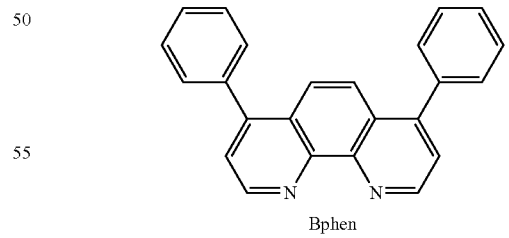

Bphen

<<Fabrication of Light-Emitting Elements 1 and 2>>

First, indium tin oxide (ITO) containing silicon oxide was deposited over a glass substrate 900 by a sputtering method, whereby a first electrode 901 functioning as an anode was formed. Note that the thickness was set to 110 nm and the electrode area was set to 2 mm×2 mm.

Next, as pretreatment for forming the light-emitting element over the substrate 900, UV ozone treatment was performed for 370 seconds after washing of a surface of the substrate with water and baking that was performed at 200° C. for an hour.

After that, the substrate 900 was transferred into a vacuum evaporation apparatus where the pressure had been reduced to approximately 1×10$^{-4}$ Pa, and was subjected to vacuum baking at 170° C. for 30 minutes in a heating chamber of the vacuum evaporation apparatus. Then, the substrate 900 was cooled down for approximately 30 minutes.

Next, the substrate 900 was fixed to a holder provided in the vacuum evaporation apparatus so that a surface of the substrate over which the first electrode 901 was formed faced downward. In this example, a case is described in which a hole-injection layer 911, a hole-transport layer 912, a light-emitting layer 913, an electron-transport layer 914, and an electron-injection layer 915, which are included in an EL layer 902, are sequentially formed by a vacuum evaporation method.

After reducing the pressure of the vacuum evaporation apparatus to 1×10$^{-4}$ Pa, 1,3,5-tri(dibenzothiophen-4-yl)benzene (abbreviation: DBT3P-II) and molybdenum oxide were co-evaporated at a mass ratio of 4:2 (DBT3P-II: molybdenum oxide), whereby the hole-injection layer 911 was formed over the first electrode 901. The thickness of the hole-injection layer 911 was 60 nm. Note that co-evaporation is an evaporation method in which a plurality of different substances are concurrently vaporized from different evaporation sources.

Then, 9-phenyl-9H-3-(9-phenyl-9H-carbazol-3-yl)carbazole (abbreviation: PCCP) was deposited by evaporation to a thickness of 20 nm, whereby the hole-transport layer 912 was formed.

Next, the light-emitting layer 913 was formed over the hole-transport layer 912.

In the case of the light-emitting element 1, 9,9'-(pyrimidine-4,6-diyldi-3,1-phenylene)bis(9H-carbazole) (abbreviation: 4,6mCzP2Pm), PCCP, and [Ir(iBuidrpypm)$_2$(acac)] were co-evaporated with a mass ratio of 4,6mCzP2Pm to PCCP and [Ir(iBuidrpypm)$_2$(acac)] being 0.7:0.3:0.05, whereby the light-emitting layer 913 with a thickness of 40 nm was formed.

In the case of the light-emitting element 2, 4,6mCzP2Pm, PCCP, and [Ir(iBuidrpypm)$_3$] were co-evaporated with a mass ratio of 4,6mCzP2Pm to PCCP and [Ir(iBuidrpypm)$_3$] being 0.7:0.3:0.05, whereby the light-emitting layer 913 with a thickness of 40 nm was formed.

Next, over the light-emitting layer 913 of each of the light-emitting elements 1 and 2, 4,6mCzP2Pm was deposited by evaporation to a thickness of 20 nm, and then Bphen was deposited by evaporation to a thickness of 10 nm, whereby the electron-transport layer 914 was formed.

Furthermore, lithium fluoride was evaporated to a thickness of 1 nm over the electron-transport layer 914, whereby the electron-injection layer 915 was formed.

Finally, aluminum was deposited to a thickness of 200 nm over the electron-injection layer 915, whereby a second electrode 903 functioning as a cathode was formed. Thus, the light-emitting elements 1 and 2 were fabricated. Note that in all the above evaporation steps, evaporation was performed by a resistance-heating method.

Table 1 shows element structures of the light-emitting elements 1 and 2 fabricated as described above.

TABLE 1

| | First electrode | Hole-injection layer | Hole-transport layer | Light-emitting layer | Electron-transport layer | Electron-injection layer | Second electrode |
|---|---|---|---|---|---|---|---|
| Light-emitting element 1 | ITO (110 nm) | DBT3P-II:MoO$_x$ (4:260 nm) | PCCP (20 nm) | * | 4,6mCzP2Pm (20 nm) Bphen (10 nm) | LiF (1 nm) | Al (200 nm) |
| Light-emitting element 2 | ITO (110 nm) | DBT3P-II:MoO$_x$ (4:260 nm) | PCCP (20 nm) | ** | 4,6mCzP2Pm (20 nm) Bphen (10 nm) | LiF (1 nm) | Al (200 nm) |

\* 4,6mCzP2Pm:PCCP:[Ir(iBuidrpypm)$_2$(acac)] (0.7:0.3:0.05 40 nm)

\*\* 4,6mCzP2Pm:PCCP:[Ir(iBuidrpypm)$_3$] (0.7:0.3:0.05 40 nm)

The fabricated light-emitting elements 1 and 2 were each sealed in a glove box containing a nitrogen atmosphere so as not to be exposed to the air (specifically, a sealant was applied to surround the elements, and at the time of sealing, UV treatment was performed first and then heat treatment was performed at 80° C. for an hour).

<<Operation Characteristics of Light-Emitting Elements 1 and 2>>

Measurement of the fabricated light-emitting elements 1 and 2 was performed. The measurement was carried out at room temperature (under an atmosphere where a temperature was maintained at 25° C.).

Figure 23:
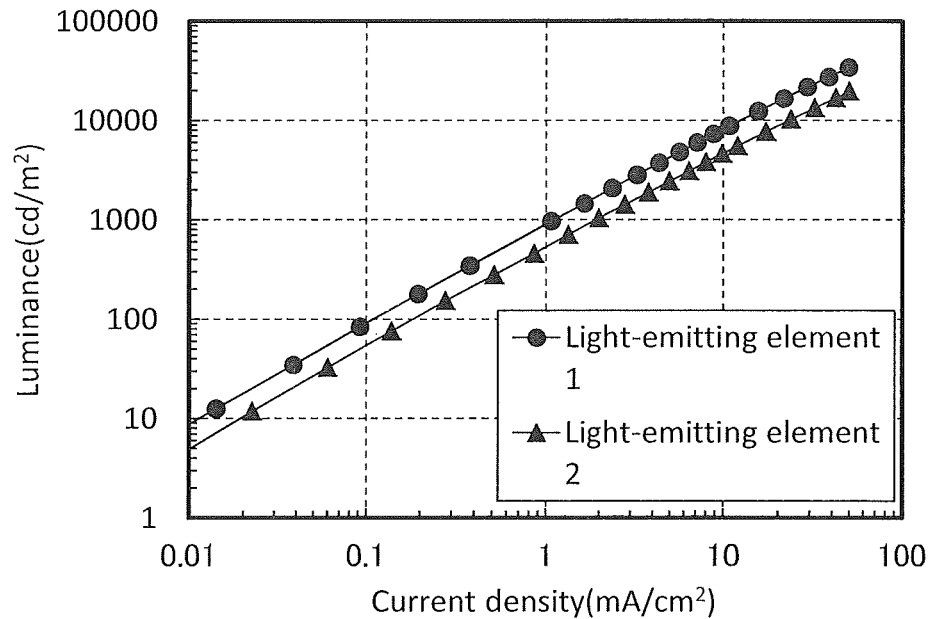
FIG. 23 shows the current density-luminance characteristics of a light-emitting element 1 and a light-emitting element 2.
Figure 24:
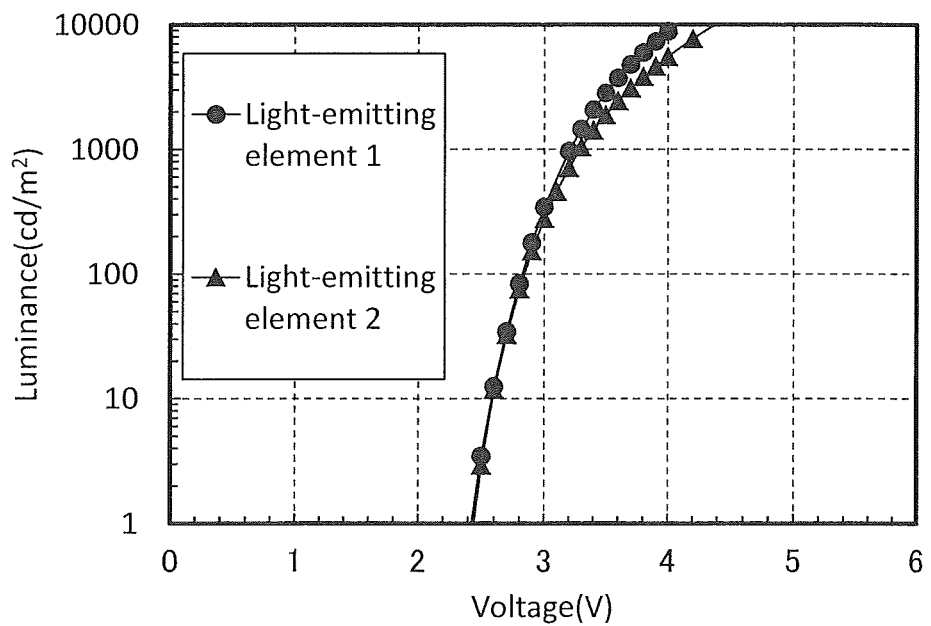
FIG. 24 shows the voltage-luminance characteristics of the light-emitting element 1 and the light-emitting element 2.
Figure 25:
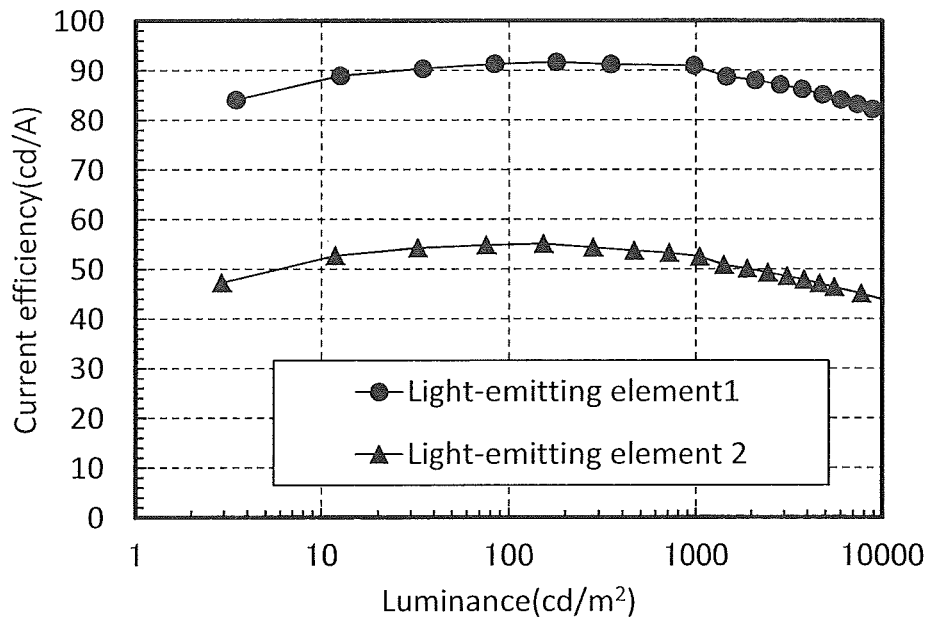
FIG. 25 shows the luminance-current efficiency characteristics of the light-emitting element 1 and the light-emitting element 2.
Figure 26:
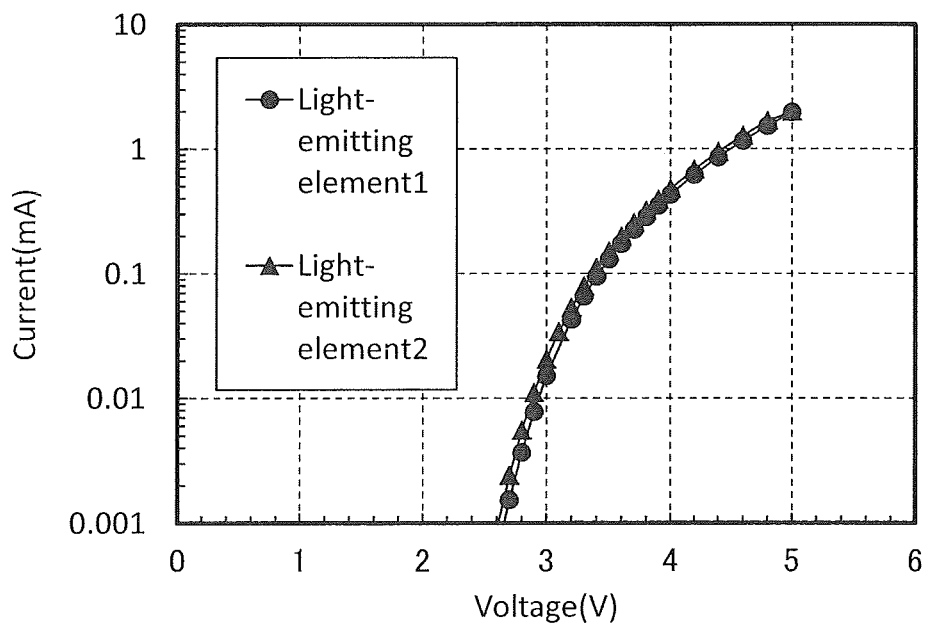
FIG. 26 shows the voltage-current characteristics of the light-emitting element 1 and the light-emitting element 2.

FIG. 23 shows the current density-luminance characteristics of the light-emitting elements 1 and 2; FIG. 24 shows the voltage-luminance characteristics thereof; FIG. 25 shows the luminance-current efficiency characteristics thereof and FIG. 26 shows the voltage-current characteristics thereof.

Table 2 shows initial values of main characteristics of the light-emitting elements 1 and 2 at a luminance of about 1000 cd/m$^2$.

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.2 | 0.043 | 1.1 | (0.30, 0.64) | 980 | 91 | 89 | 25 |
| Light-emitting element 2 | 3.3 | 0.080 | 2.0 | (0.31, 0.64) | 1000 | 53 | 50 | 14 |

Figure 27:
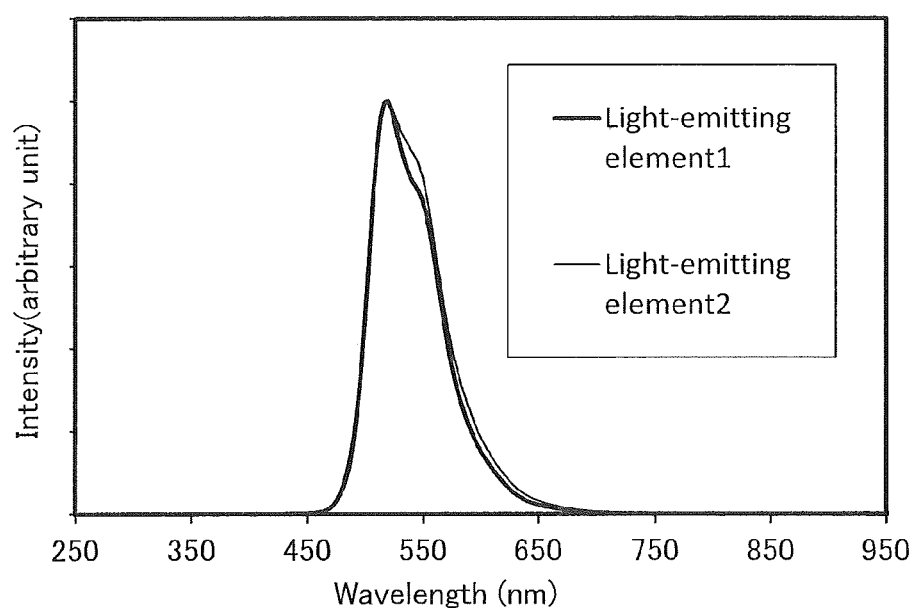
FIG. 27 shows emission spectra of the light-emitting element 1 and the light-emitting element 2.

FIG. 27 shows emission spectra of the light-emitting elements 1 and 2 to which current was applied at a current density of 25 mA/cm$^2$. As shown in FIG. 27, each of the emission spectra of the light-emitting elements 1 and 2 has a peak at around 520 nm, which indicates that the peaks are derived from green light emission of [Ir(iBuidrpypm)$_2$(acac)] and [Ir(iBuidrpypm)$_3$] each of which is the organometallic complex of one embodiment of the present invention.

This application is based on Japanese Patent Application serial no. 2015-212831 filed with Japan Patent Office on Oct. 29, 2015, the entire contents of which are hereby incorporated by reference.

What is claimed is:

1. An organometallic complex comprising:
   iridium; and
   a first ligand,
   wherein the first ligand comprises a pyrido[2,3-b]indole skeleton and a pyrimidine skeleton bonded to a 3-position of the pyrido[2,3-b]indole skeleton, and
   wherein a 2-position of the pyrido[2,3-b]indole skeleton and the pyrimidine skeleton are each bonded to the iridium.

2. The organometallic complex according to claim 1, further comprising a second ligand,
   wherein the first ligand and the second ligand are bonded to the iridium, and
   wherein the second ligand is a monoanionic bidentate chelate ligand having a β-diketone structure, a monoanionic bidentate chelate ligand having a carboxyl group, a monoanionic bidentate chelate ligand having a phenolic hydroxyl group, a monoanionic bidentate chelate ligand in which two ligand elements are both nitrogen, or an aromatic heterocyclic bidentate ligand which can form a metal-carbon bonding with iridium by cyclometalation.

3. The organometallic complex according to claim 1, wherein a 3-position of the pyrimidine skeleton is bonded to the iridium.

4. A light-emitting element comprising the organometallic complex according to claim 1.

5. A light-emitting device comprising the light-emitting element according to claim 4.

6. An electronic device comprising the light-emitting device according to claim 5.

7. A lighting device comprising the light-emitting device according to claim 5.

8. An organometallic complex comprising a structure represented by a general formula (G1):

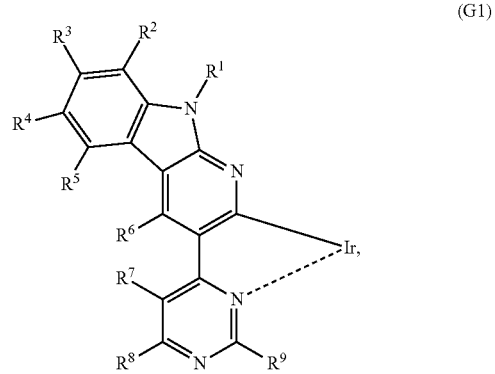

(G1)

wherein R$^1$ to R$^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

9. A light-emitting element comprising the organometallic complex according to claim 8.

10. A light-emitting device comprising the light-emitting element according to claim 9.

11. An electronic device comprising the light-emitting device according to claim 10.

12. A lighting device comprising the light-emitting device according to claim 10.

13. An organometallic complex represented by a general formula (G2):

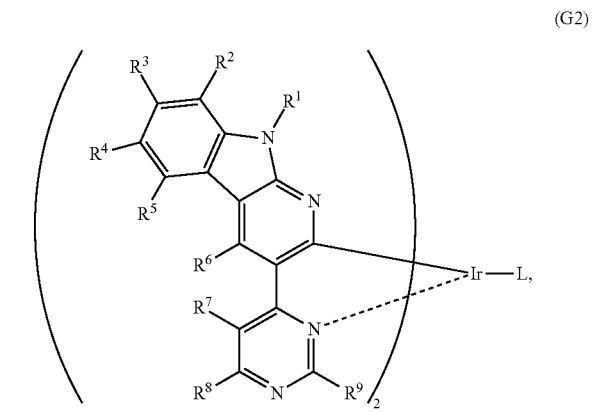

(G2)

wherein R$^1$ to R$^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms, and wherein L represents a monoanionic ligand.

14. The organometallic complex according to claim 13, wherein the monoanionic ligand is a monoanionic bidentate chelate ligand having a β-diketone structure, a monoanionic bidentate chelate ligand having a carboxyl group, a monoanionic bidentate chelate ligand having a phenolic hydroxyl group, a monoanionic bidentate chelate ligand in which two ligand elements are both nitrogen, or an aromatic heterocyclic bidentate ligand which can form a metal-carbon bonding with iridium by cyclometalation.

15. The organometallic complex according to claim 13, wherein the monoanionic ligand is represented by any one of general formulae (L1) to (L7), (L1)
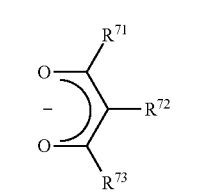

(L2)
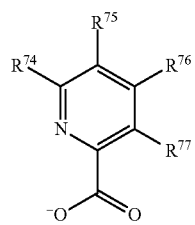

(L3)
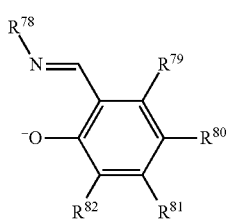

(L4)
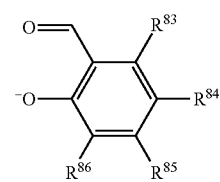

(L5)
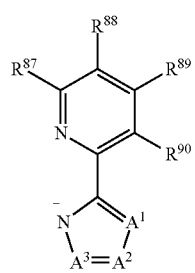

(L6)
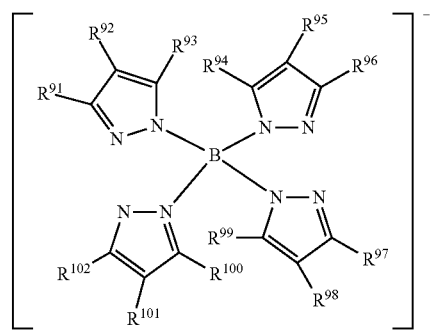

(L7)
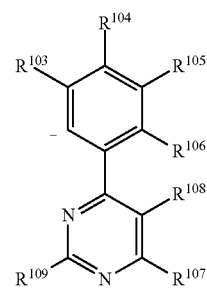

wherein $R^{71}$ to $R^{109}$ each independently represent any of hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms, wherein each of $A^1$ to $A^3$ independently represents nitrogen, $sp^2$ hybridized carbon bonded to hydrogen, or $sp^2$ hybridized carbon having a substituent, and wherein the substituent is an alkyl group having 1 to 6 carbon atoms, a halogen group, a haloalkyl group having 1 to 6 carbon atoms, or a phenyl group.

16. A light-emitting element comprising the organometallic complex according to claim 13.

17. A light-emitting device comprising the light-emitting element according to claim 16.

18. An electronic device comprising the light-emitting device according to claim 17.

19. A lighting device comprising the light-emitting device according to claim 17.

20. An organometallic complex represented by a general formula (G3):

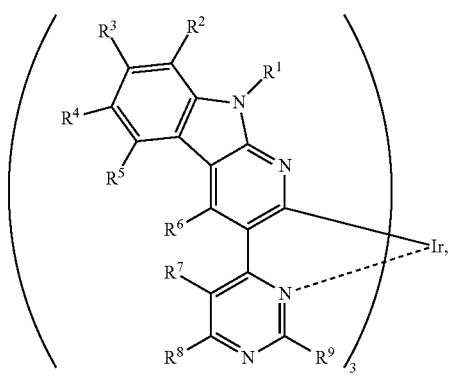

(G3)

wherein $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

21. The organometallic complex according to claim 20, wherein the organometallic complex is represented by a structural formula (112):

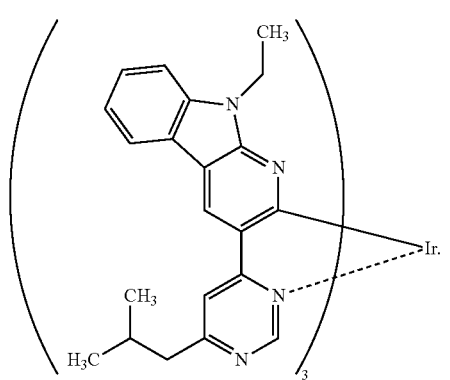

(112)

22. A light-emitting element comprising the organometallic complex according to claim 20.

23. An organometallic complex represented by a general formula (G4):

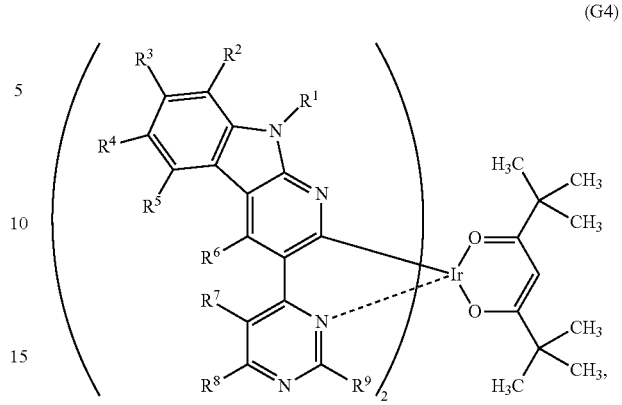

(G4)

wherein $R^1$ to $R^9$ each independently represent any of hydrogen, a substituted or unsubstituted alkyl group having 1 to 6 carbon atoms, a substituted or unsubstituted aryl group having 6 to 13 carbon atoms, and a substituted or unsubstituted heteroaryl group having 3 to 12 carbon atoms.

24. The organometallic complex according to claim 23, wherein the organometallic complex is represented by a structural formula (100):

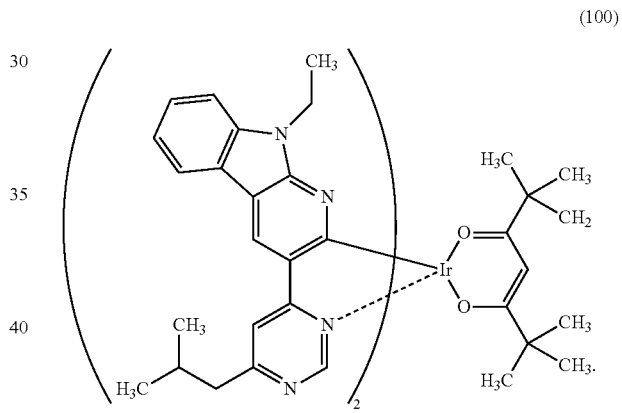

(100)

25. A light-emitting element comprising the organometallic complex according to claim 23.

* * * * *

UNITED STATES PATENT AND TRADEMARK OFFICE
CERTIFICATE OF CORRECTION

PATENT NO. : 9,843,002 B2
APPLICATION NO. : 15/332309
DATED : December 12, 2017
INVENTOR(S) : Yamaguchi et al.

It is certified that error appears in the above-identified patent and that said Letters Patent is hereby corrected as shown below:

Column 78, Lines 27 thru 44, Claim 24:

Change " 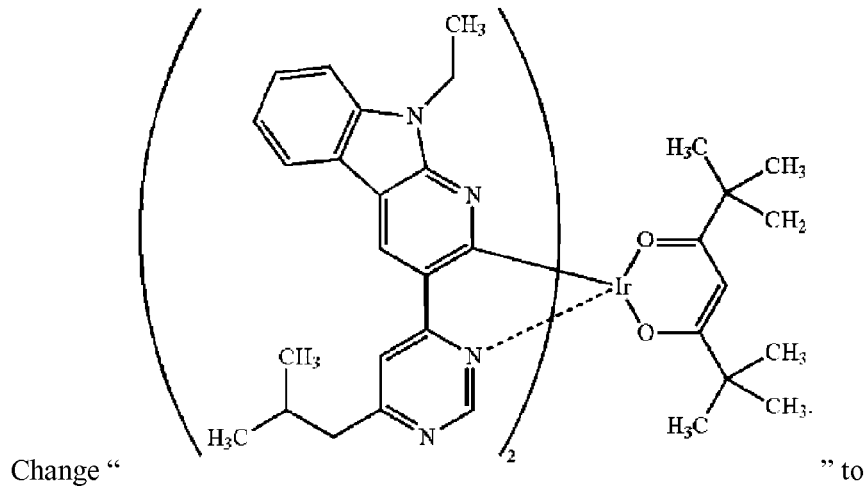 " to

-- 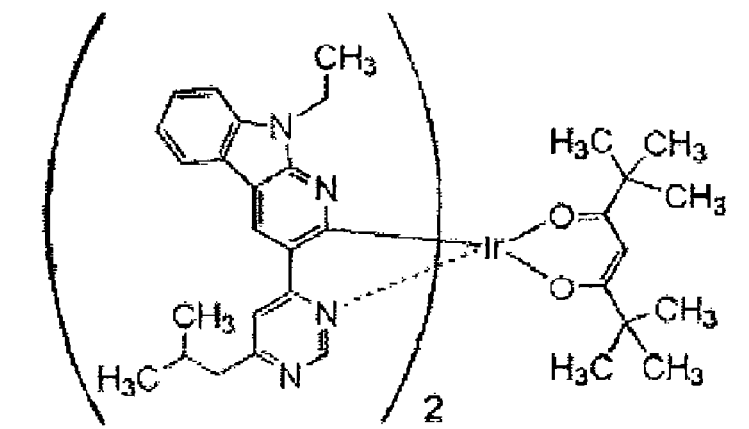 --

Signed and Sealed this
Thirteenth Day of March, 2018

Andrei Iancu
*Director of the United States Patent and Trademark Office*